US010980877B2

(12) United States Patent
Swartz et al.

(10) Patent No.: US 10,980,877 B2
(45) Date of Patent: Apr. 20, 2021

(54) METHOD FOR TREATING MELANOMA USING LYMPHANGIOGENESIS INDUCERS AND A MELANOMA-SPECIFIC ANTIGEN

(71) Applicant: The University of Chicago, Chicago, IL (US)

(72) Inventors: Melody A. Swartz, Chicago, IL (US); Jeffrey A. Hubbell, Chicago, IL (US); Shann Yu, Chicago, IL (US); Efthymia Vokali, Chicago, IL (US); Manuel Fankhauser, Chicago, IL (US); Sachiko Hirosue, Chicago, IL (US); Priscilla S. Briquez, Chicago, IL (US); Maria Broggi, Chicago, IL (US); Lambert Potin, Chicago, IL (US); Maria Stella Sasso, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 16/096,990

(22) PCT Filed: Apr. 28, 2017

(86) PCT No.: PCT/US2017/030242
§ 371 (c)(1),
(2) Date: Oct. 26, 2018

(87) PCT Pub. No.: WO2017/190074
PCT Pub. Date: Nov. 2, 2017

(65) Prior Publication Data
US 2019/0099485 A1    Apr. 4, 2019

Related U.S. Application Data

(60) Provisional application No. 62/329,133, filed on Apr. 28, 2016.

(51) Int. Cl.
| | | |
|---|---|---|
| *A61K 39/39* | (2006.01) | |
| *A61K 38/18* | (2006.01) | |
| *A61P 35/00* | (2006.01) | |
| *A61K 39/00* | (2006.01) | |
| *A61K 38/19* | (2006.01) | |
| *A61K 47/42* | (2017.01) | |
| *C07K 14/49* | (2006.01) | |
| *C07K 16/28* | (2006.01) | |
| *G01N 33/574* | (2006.01) | |
| *C12N 9/10* | (2006.01) | |
| *A61P 37/04* | (2006.01) | |
| *A61P 35/04* | (2006.01) | |
| *A61K 9/06* | (2006.01) | |
| *A61K 45/06* | (2006.01) | |

(52) U.S. Cl.
CPC ............ *A61K 39/39* (2013.01); *A61K 9/06* (2013.01); *A61K 38/1866* (2013.01); *A61K 38/195* (2013.01); *A61K 39/00* (2013.01); *A61K 39/0011* (2013.01); *A61K 39/00119* (2018.08); *A61K 39/001156* (2018.08); *A61K 39/001192* (2018.08); *A61K 45/06* (2013.01); *A61K 47/42* (2013.01); *A61P 35/00* (2018.01); *A61P 35/04* (2018.01); *A61P 37/04* (2018.01); *C07K 14/49* (2013.01); *C07K 16/2863* (2013.01); *C07K 16/2866* (2013.01); *C12N 9/1044* (2013.01); *G01N 33/574* (2013.01); *A61K 2039/505* (2013.01); *A61K 2039/507* (2013.01); *A61K 2039/5154* (2013.01); *A61K 2039/5158* (2013.01); *A61K 2039/545* (2013.01); *A61K 2039/55* (2013.01); *A61K 2039/55516* (2013.01); *A61K 2039/55561* (2013.01); *A61K 2039/575* (2013.01); *A61K 2039/876* (2018.08); *C07K 16/2818* (2013.01); *C07K 2317/76* (2013.01); *C07K 2319/50* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 2002/0151489 | A1 | 10/2002 | Gravereaux et al. |
| 2004/0086489 | A1 | 5/2004 | Schall et al. |
| 2013/0251752 | A1 | 9/2013 | Antonia et al. |
| 2014/0127193 | A1 | 5/2014 | Nixon et al. |

FOREIGN PATENT DOCUMENTS

| | | | | |
|---|---|---|---|---|
| WO | WO 2002/058723 | * | 8/2002 | ............ A61K 38/19 |
| WO | WO 2015/168379 | | 11/2015 | |
| WO | WO 2016/102374 | | 6/2016 | |

OTHER PUBLICATIONS

Kim et al. Extracorporeal shock wave therapy combined with Vascular Endothelial Growth Factor-C Hydrogel for lymphangiogenesis, J. Vasc. Res. 50, 124-133, 2013. (Year: 2013).*
Ehrbar et al. Cell-demanded liberation of VEGF from fibrin implants induces local and controlled blood vessel Growth. Circ. Res. 94, 1124-1132, 2004. (Year: 2004).*
((https://en.wikipedia.org/wiki/List_of_cancer_types—accessed May 22, 2020. (Year: 2020).*
https://www.cancer.gov/about-cancer/understanding/what-is-cancer accessed May 22, 2020. (Year: 2020).*
Hirosue et al., "Steady Antigen Scavenging, Cross-Presentation, and CD8+ T Cell Priming: A New Role for Lymphatic Endothelial Cells" *Journal of Immunology*, 2014, 192:5002-5011.

(Continued)

*Primary Examiner* — Elly-Gerald Stoica
(74) *Attorney, Agent, or Firm* — Norton Rose Fulbright US LLP

(57) ABSTRACT

The present invention concerns methods and compositions for evoking protective immune responses against pathogen infection or cancer. In certain embodiments, the methods and compositions comprise a lymphangiogenesis inducer and an antigen.

12 Claims, 32 Drawing Sheets
Specification includes a Sequence Listing.

(56) References Cited

OTHER PUBLICATIONS

Hubbell et al., "Materials engineering for immunomodulation," *Nature*, 2009, 462:449-460.
Moon et al., "Engineering nano- and microparticles to tune immunity," *Advanced Materials*, 2012, 24:3724-3746.
Zisch et al., "Covalently conjugated VEGF-fibrin matrices for endothelialization," *Journal of Controlled Release*, 2001, 72:101-113.
Card, et al.,"Emerging Roles of Lymphatic Endothelium in Regulating Adaptive Immunity," *The Journal of Clinical Investigation*, 124; 943-952, 2014.
International Search Report Issued in Corresponding PCT Application No. PCT/US2017/030242, dated Jul. 13, 2017.
Lund, et al., "VEGF-C Promotes Immune Tolerance in B16 Melanomas and Cross Presentation of Tumor Antigen by Lymph Node Lymphatics," *Cell Reports*, 1(3); 191-199, 2012.
Martino, et al., "Growth Factors Engineered for Super-Affinity to the Extracellular Matrix Enhance Tissue Healing," *Science*, 343(6173); 885-888, 2014.
Martino, et al., "Heparin-Binding Domain of Fibrin(ogen) Binds Growth Factors and Promotes Tissue Repair When Incorporated Within a Synthetic Matrix," PNAS, 110; 4563-4568, 2013.
Cheng, et al. "Serum Vascular Endothelial Growth Factor (VEGF-C) as a Diagnostic and Prognostic Marker in Patients with Ovarian Cancer," *PLOS One*, 2013, 8(2):e55309.
Dadras, et al. "Tumor Lymphangiogenesis A Novel Prognostic Indicator for Cutaneous Melanoma Metastasis and Survival," *American Journal of Pathology*, 2003, 162(6):1951-1960.
Dobrzycka, et al. "Serum levels of VEGF and VEGF-C in patients with endometrial cancer," *Eur. Cytokine Netw*, 2011, 22(1):45-51.
Fankhauser, et al. "Tumor lymphangiogenesis promotes T cell infiltration and potentiates immunotherapy in melanoma," *Science Translational Medicine*, 2017, 9:eaal4712.
Jiang, et al. "Serum vascular endothelial growth factor-C levels predict lymph node metastasis and prognosis of patients with gallbladder cancer," *Oncology Letters*, 2018, 16:6065-6070.
Liang, et al. "Elevated VEGF concentrations in ascites and serum predict adverse prognosis in ovarian cancer," *Scandinavian Journal of Clinical and Laboratory Investigation*, 2013, 73:309-314.

\* cited by examiner

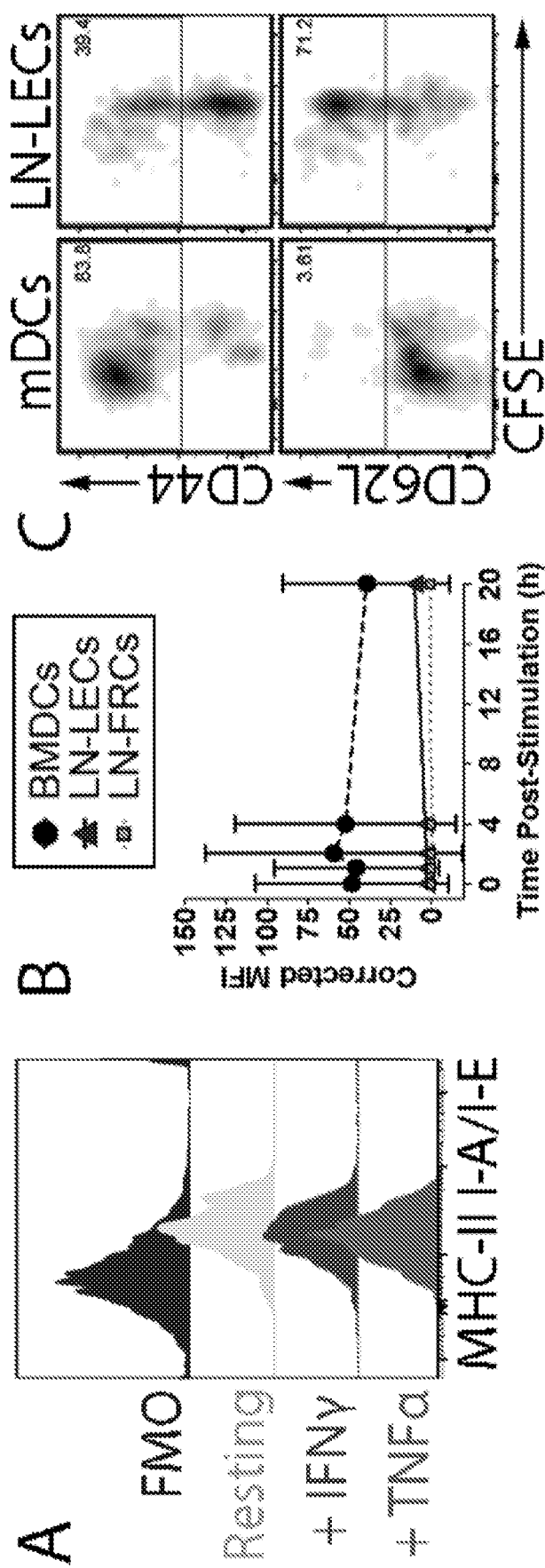
FIG. 1A-C

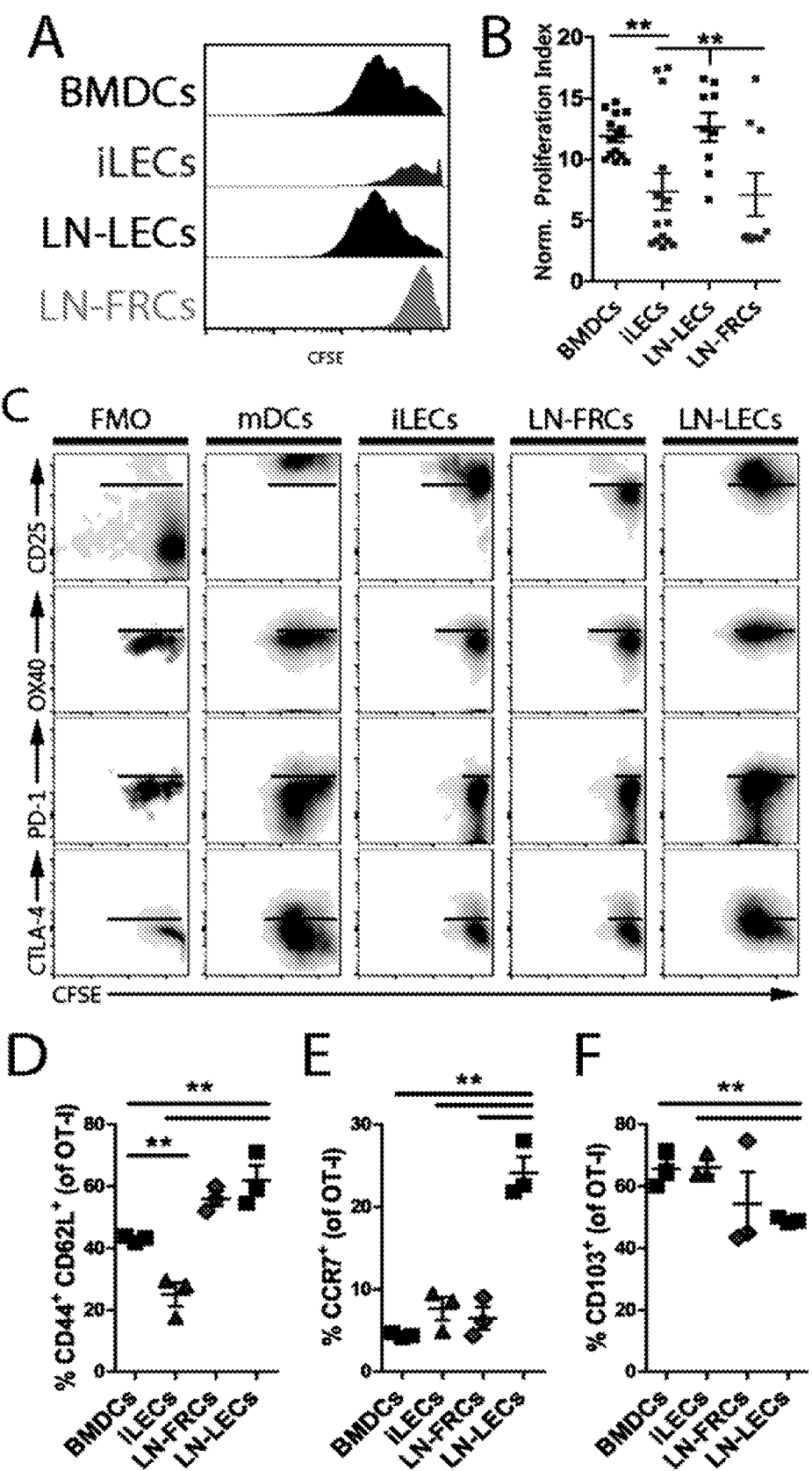
FIG. 2A-F

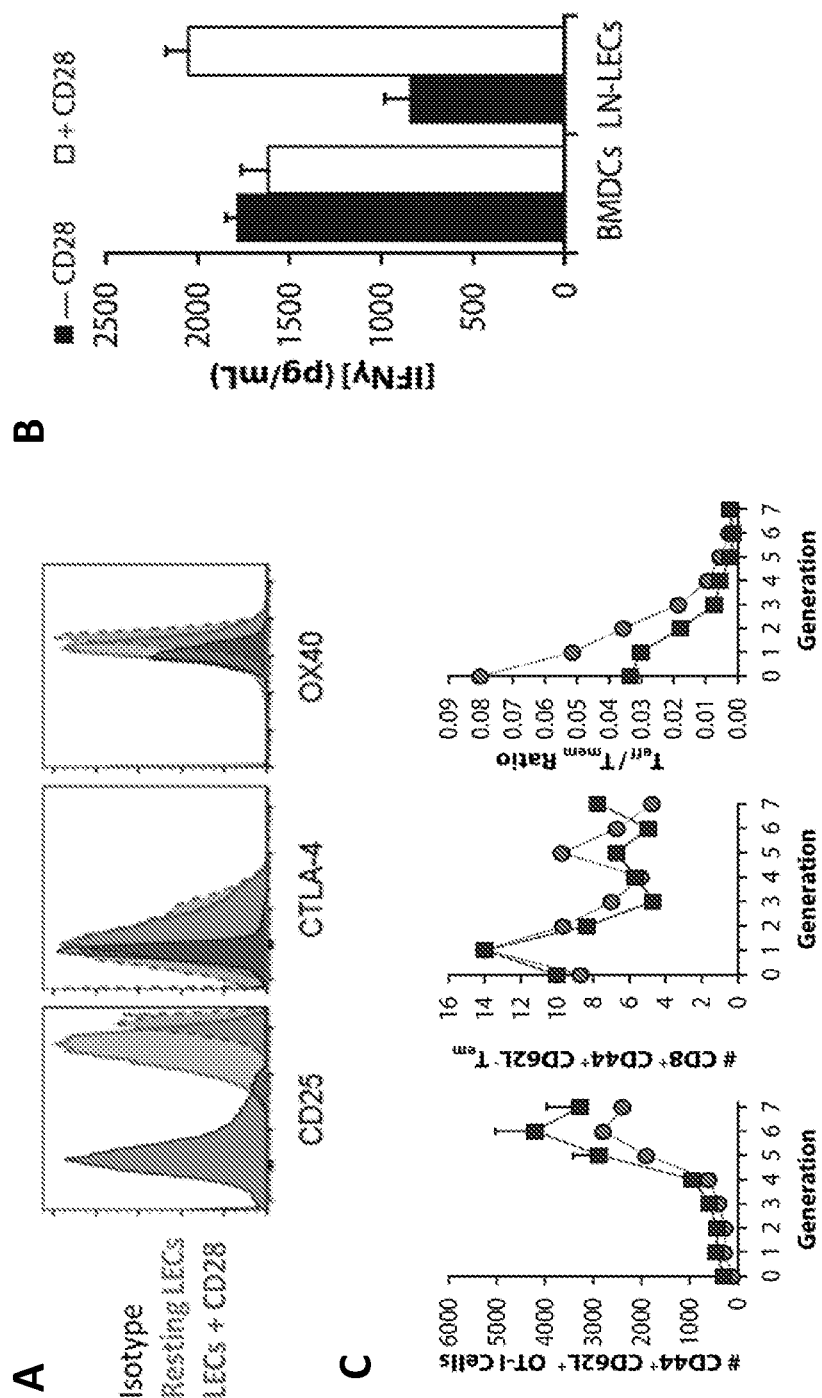
FIG. 3A-C

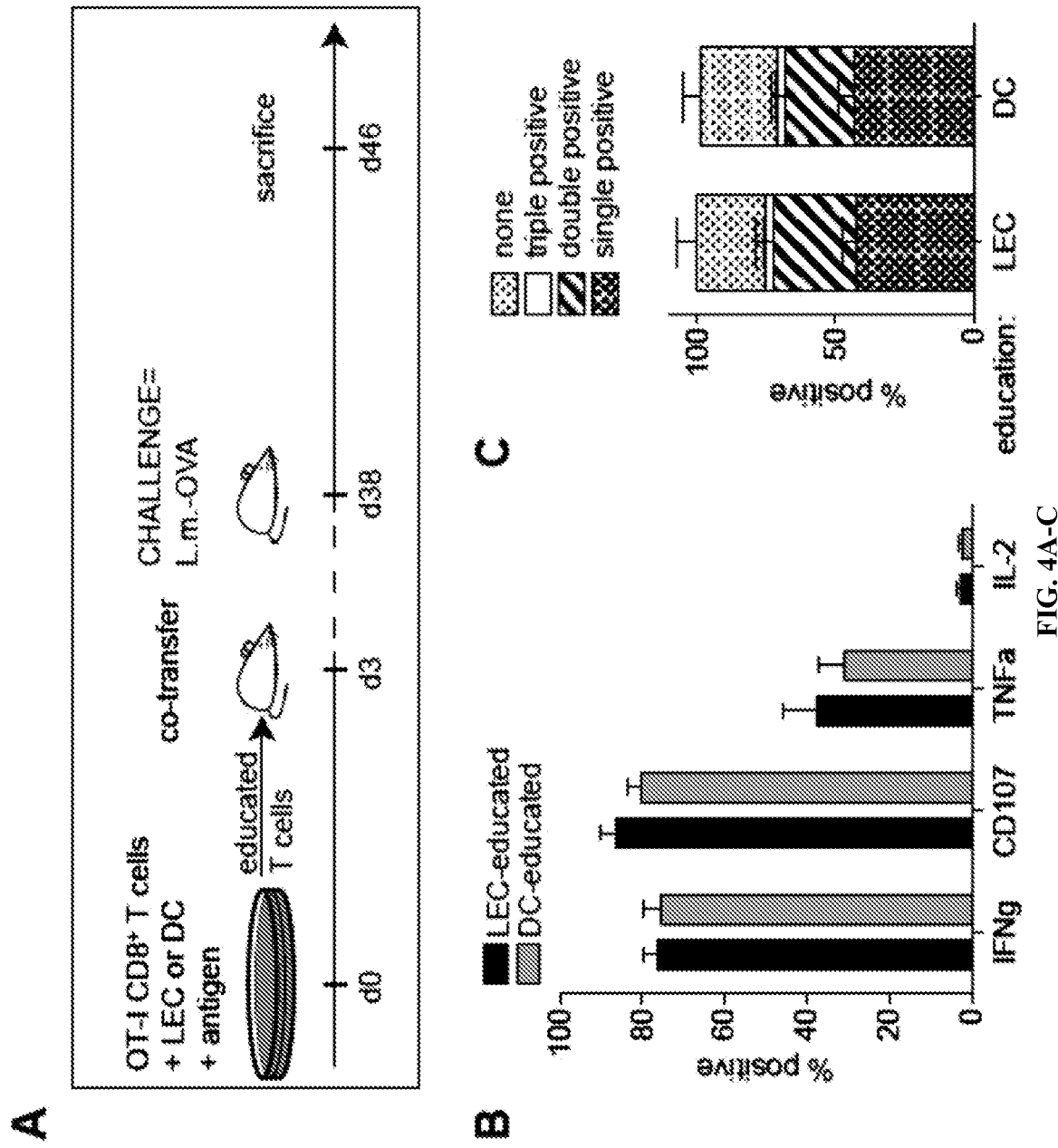
FIG. 4A-C

D
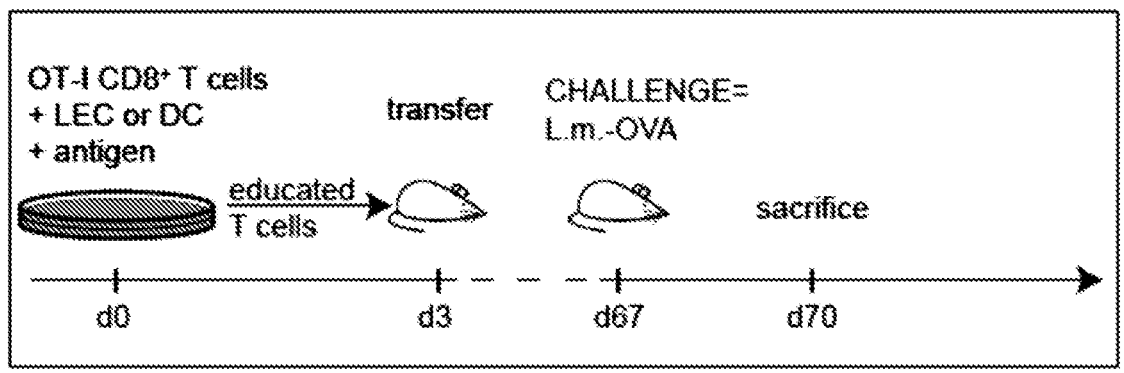
E
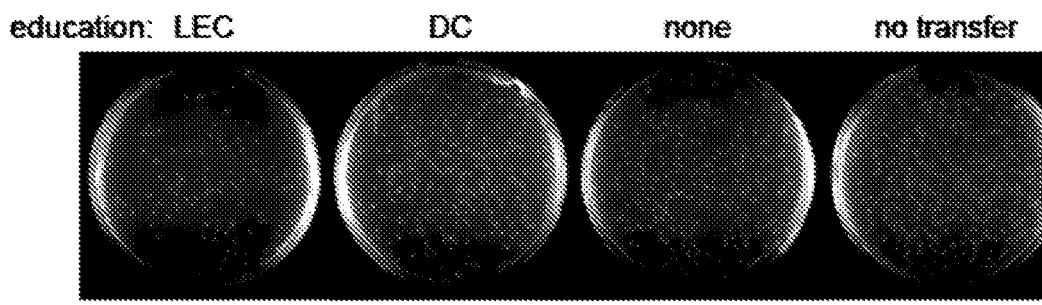
F
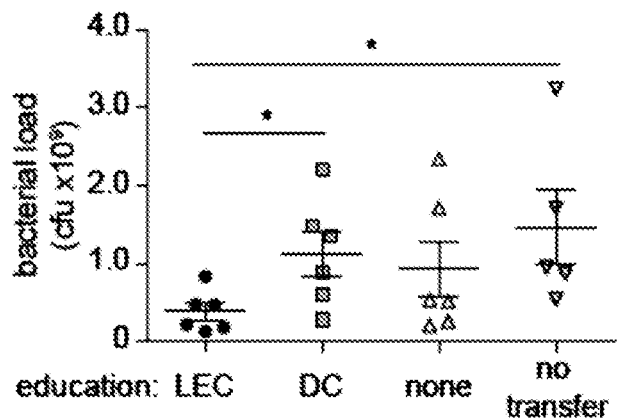
FIG. 4D-F

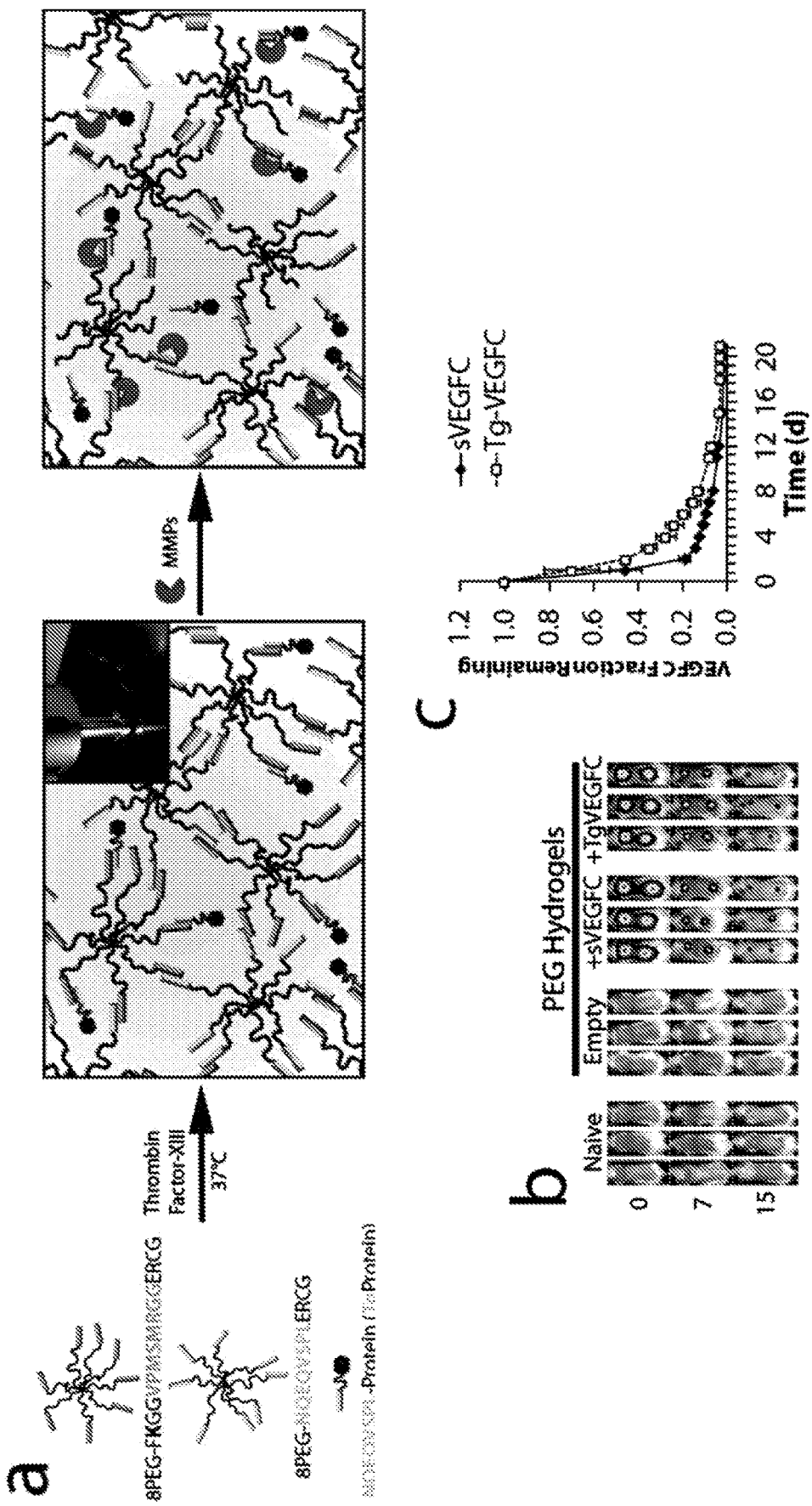
FIG. 5A-C

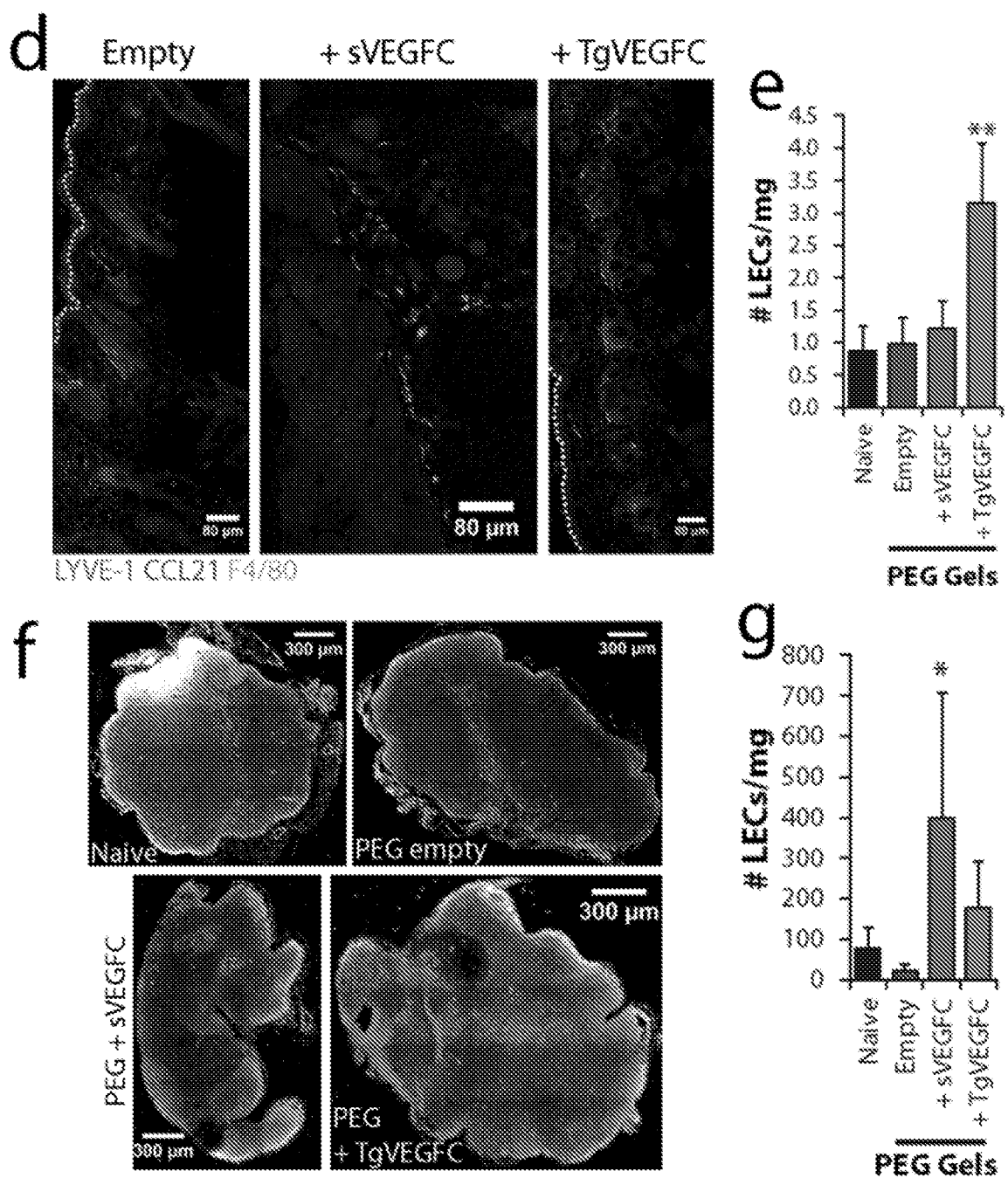
FIG. 5D-G

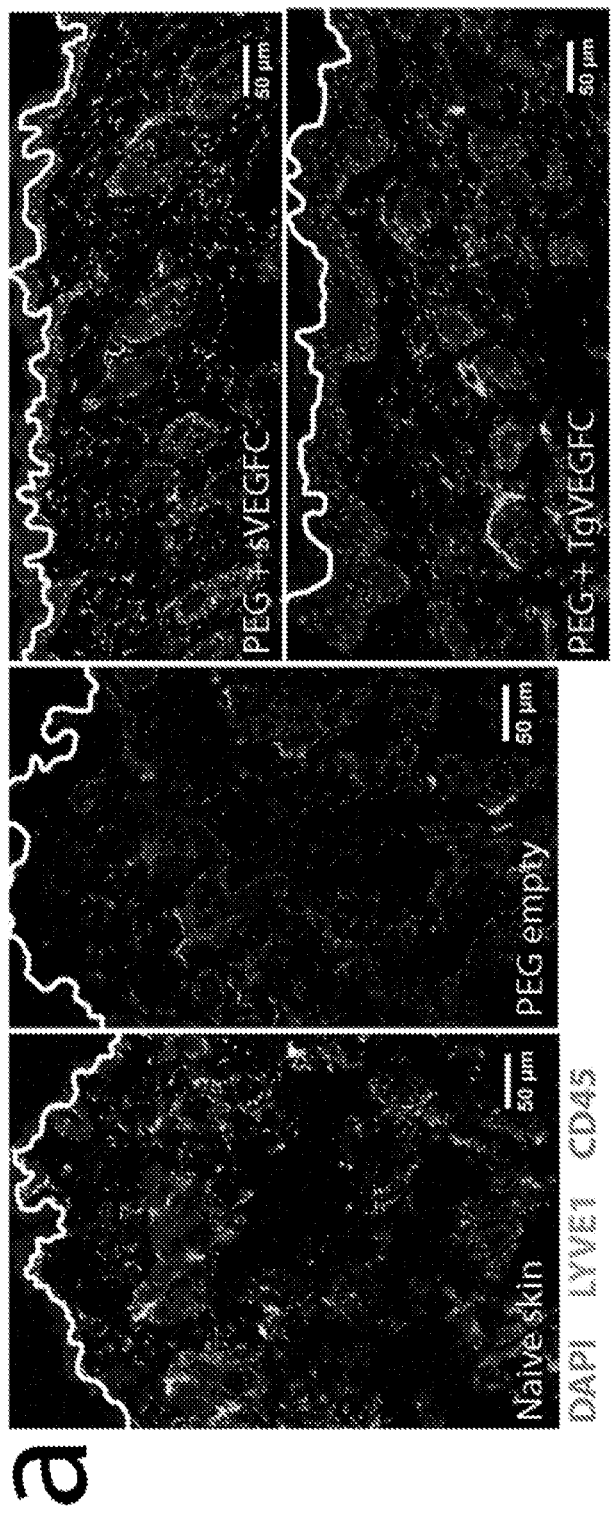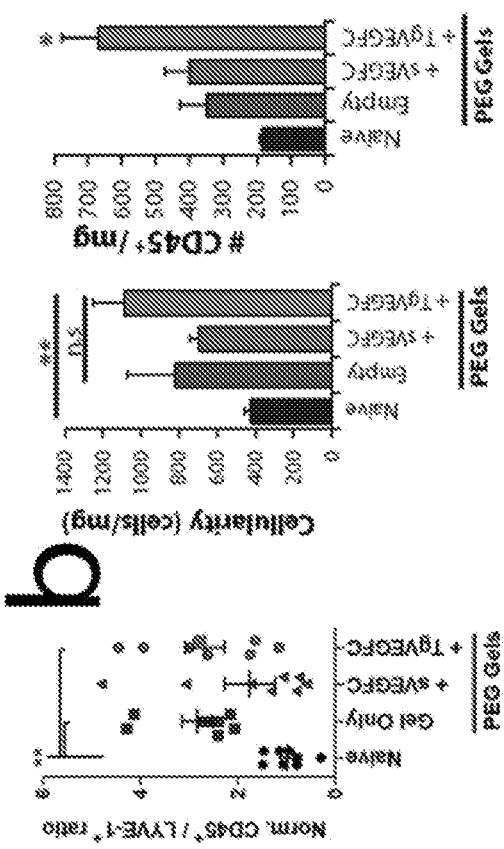
FIG. 6A-B

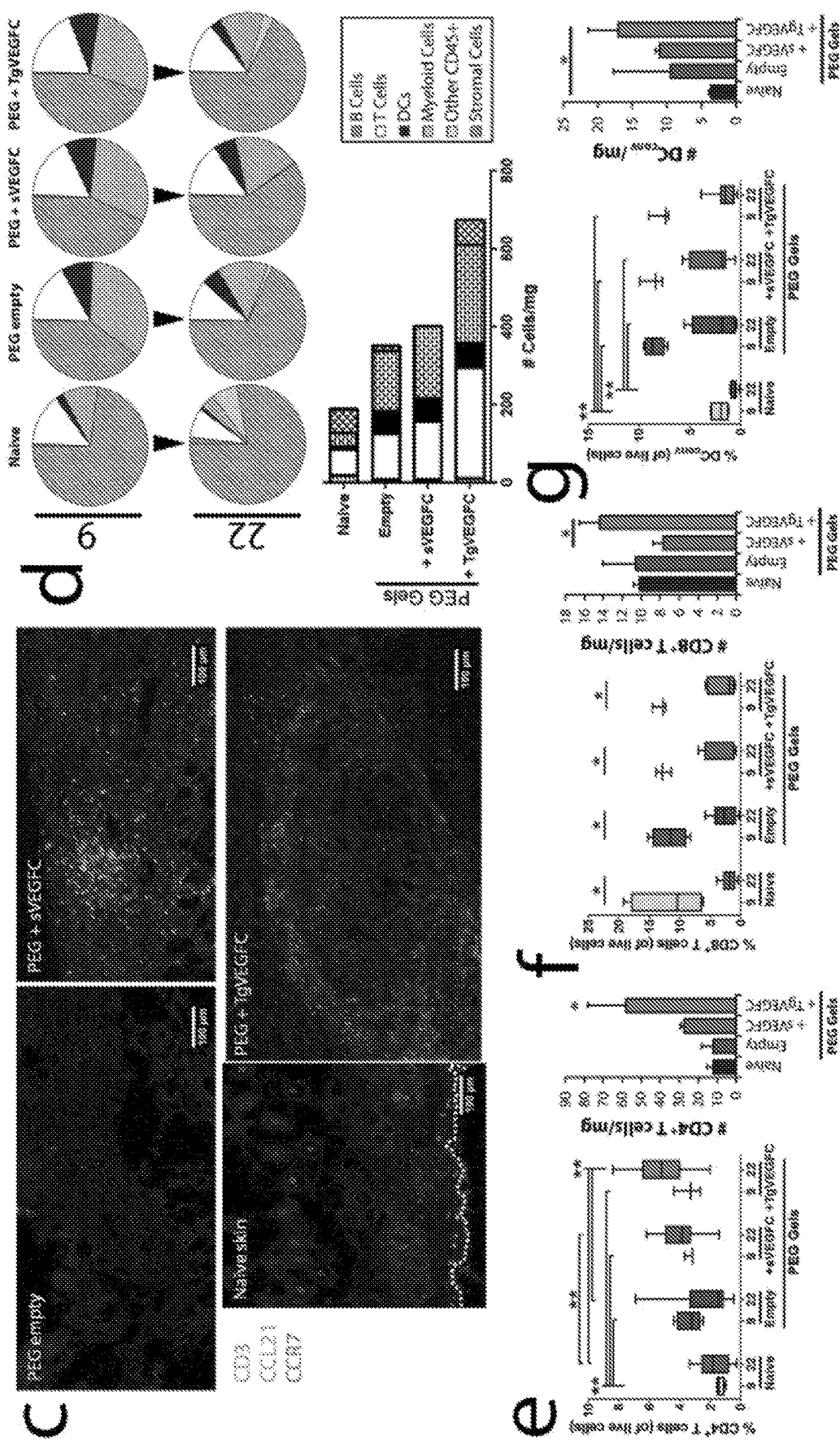
FIG. 6C-G

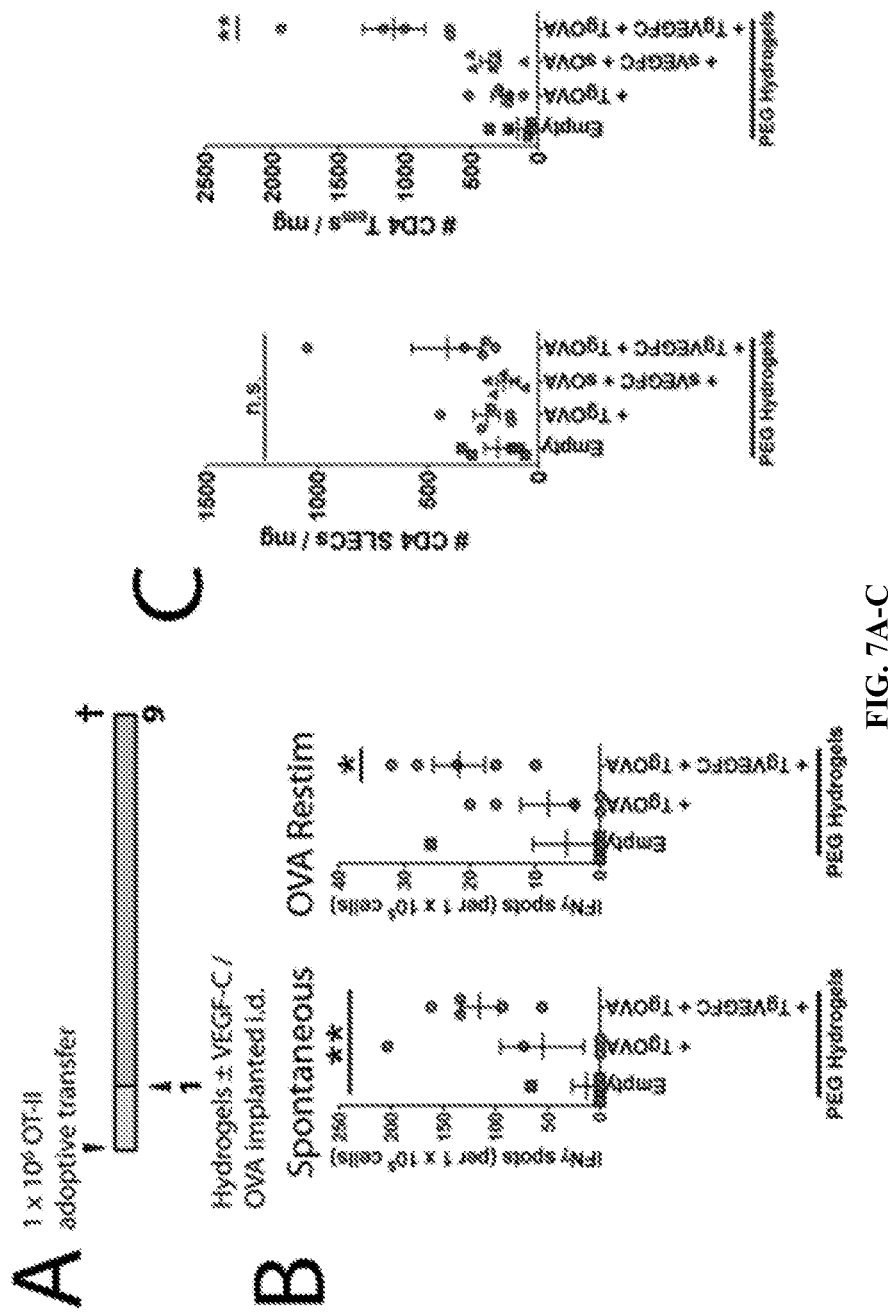
FIG. 7A-C

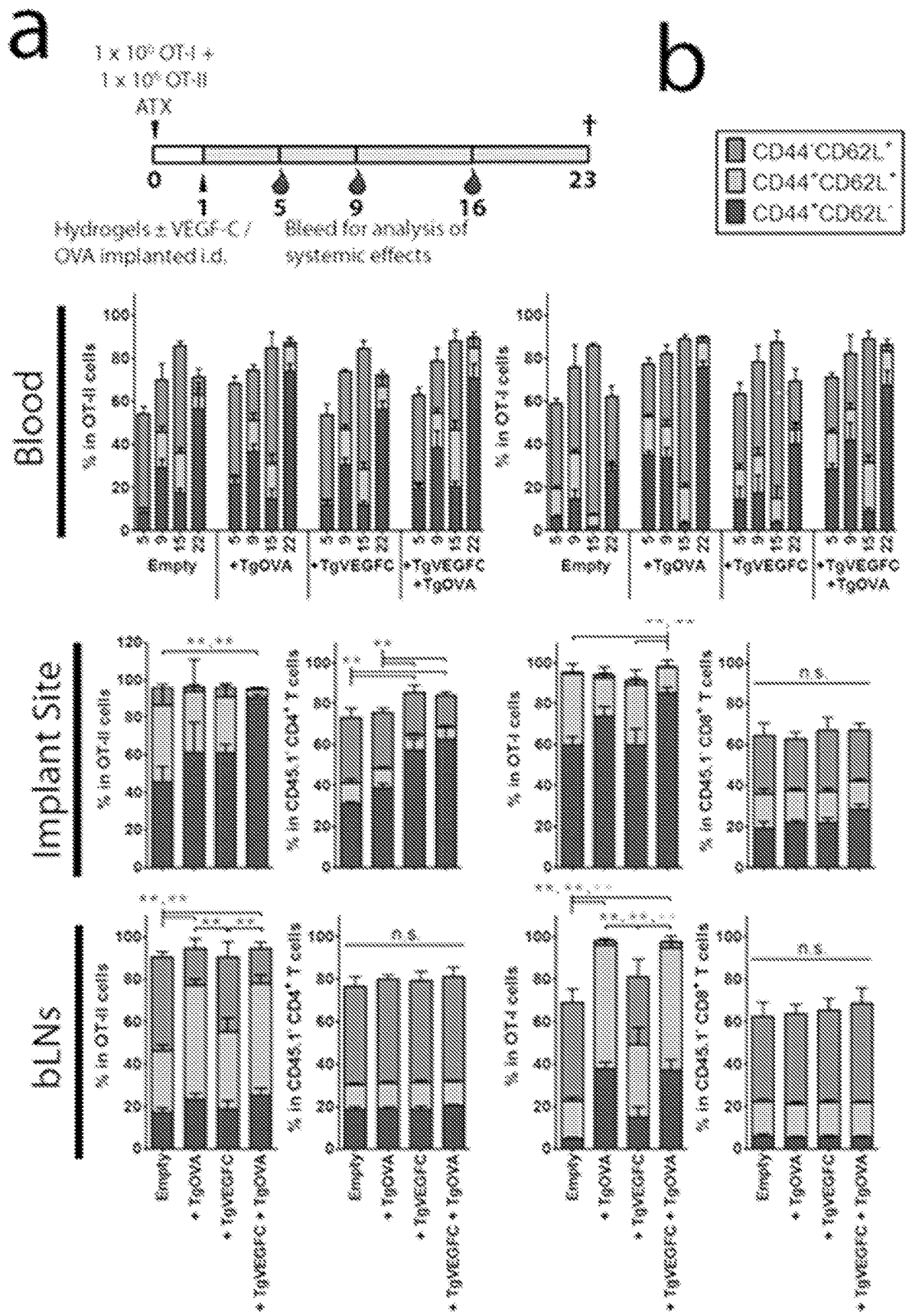
FIG. 8A-B

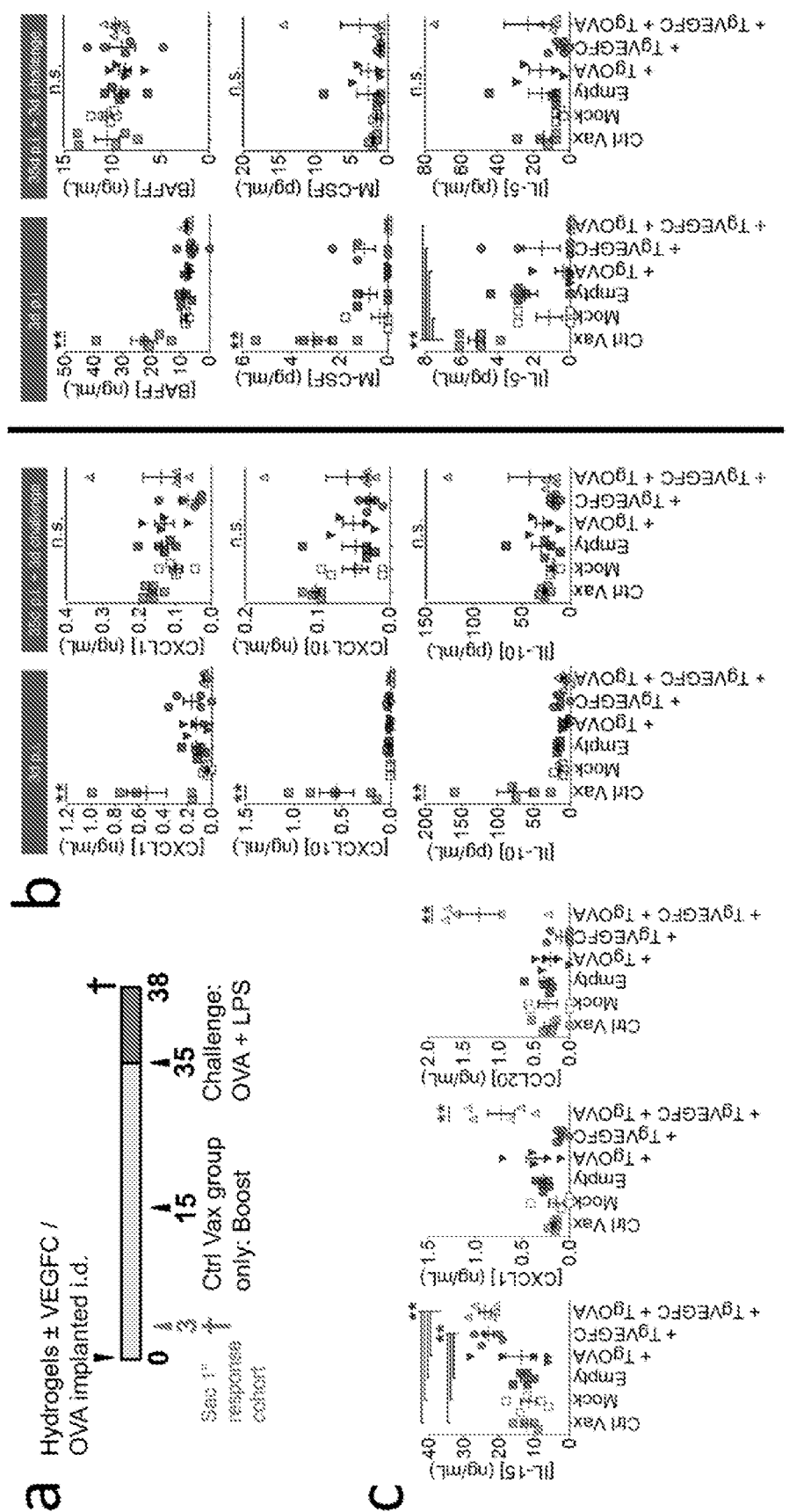
FIG. 9A-C

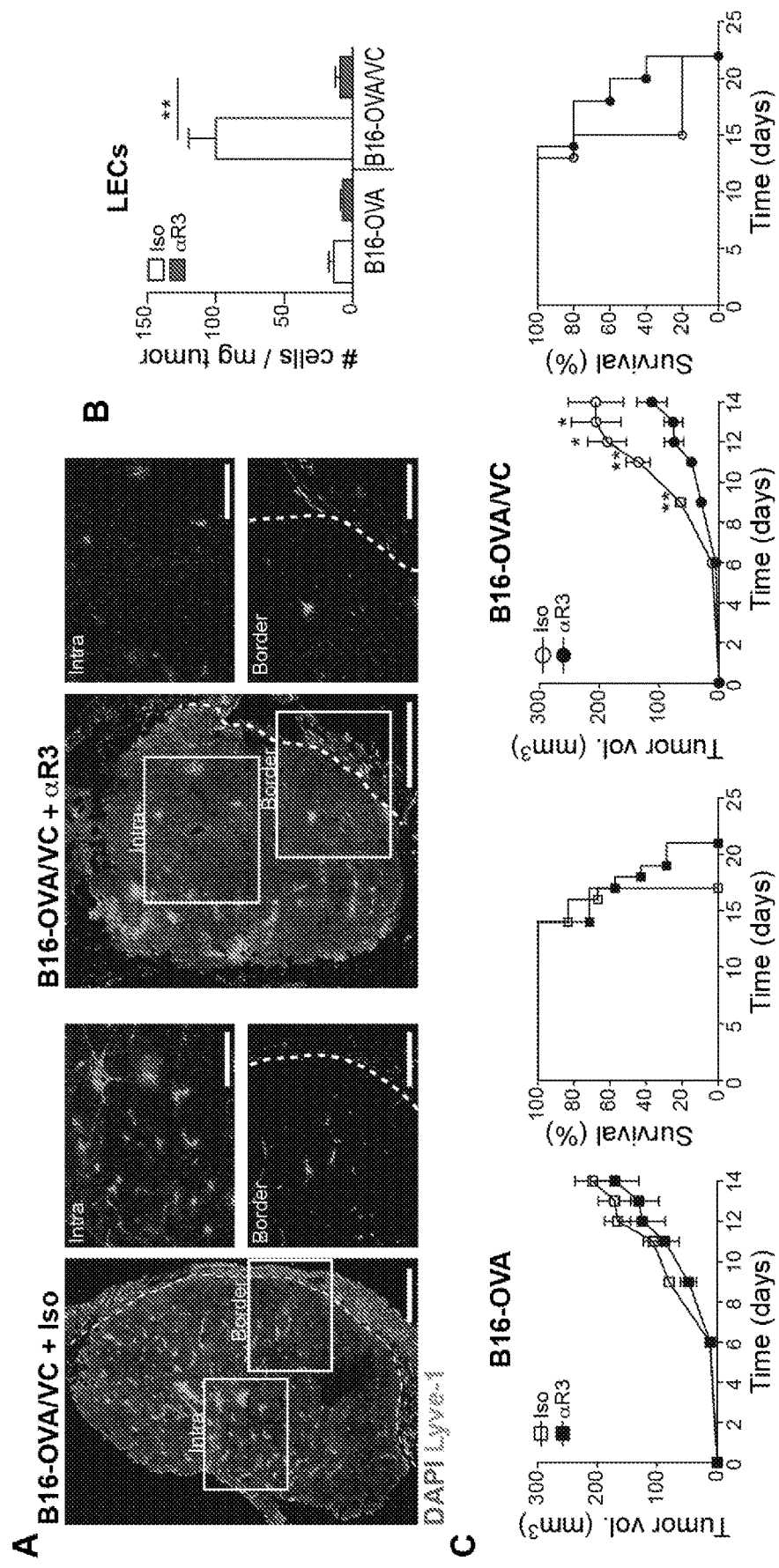
FIG. 10A-C

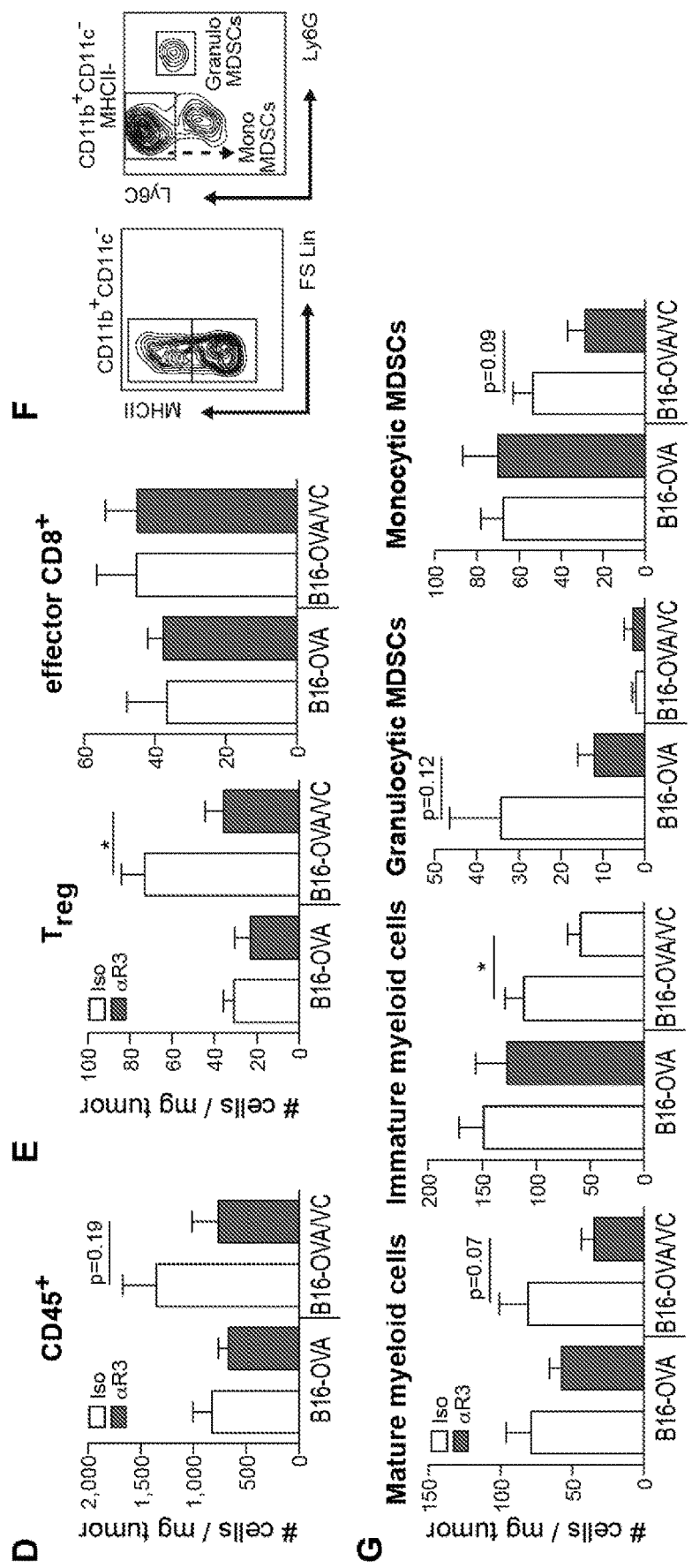
FIG. 10D-G

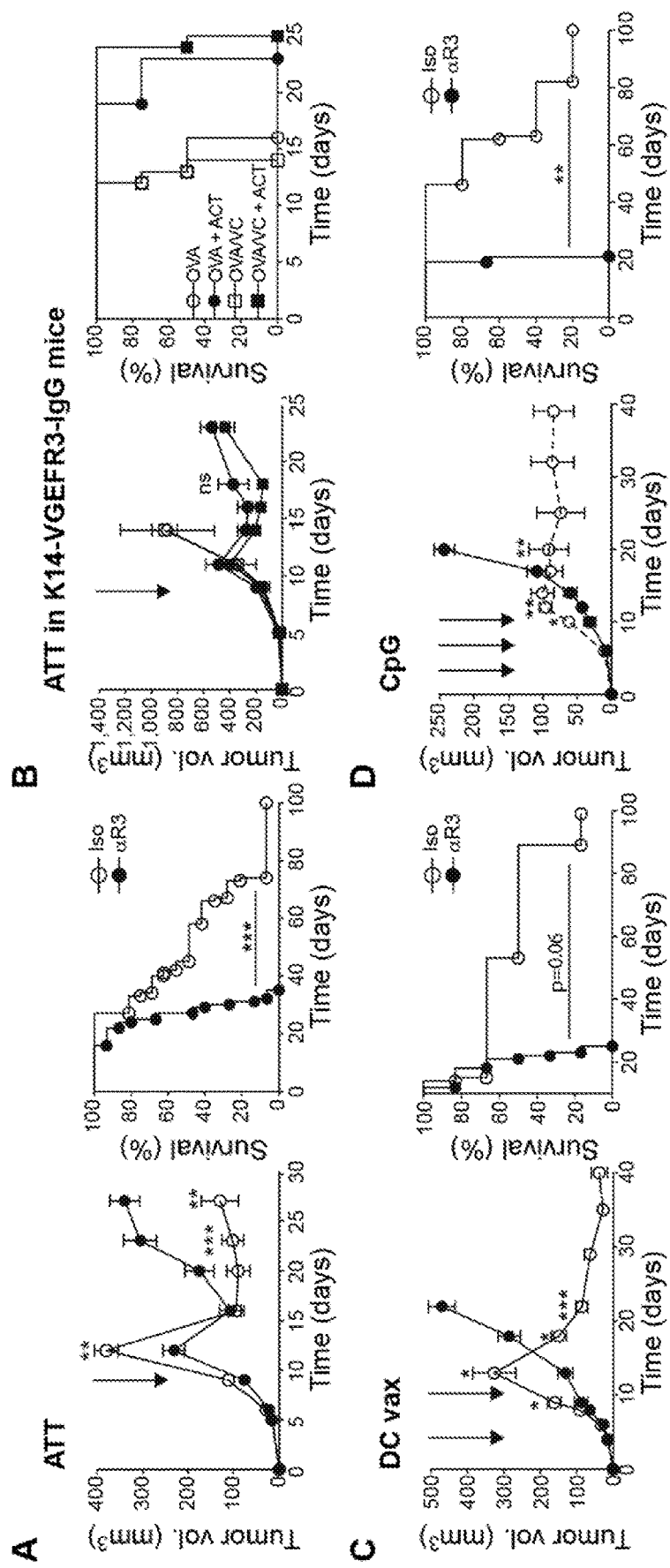
FIG. 11A-D

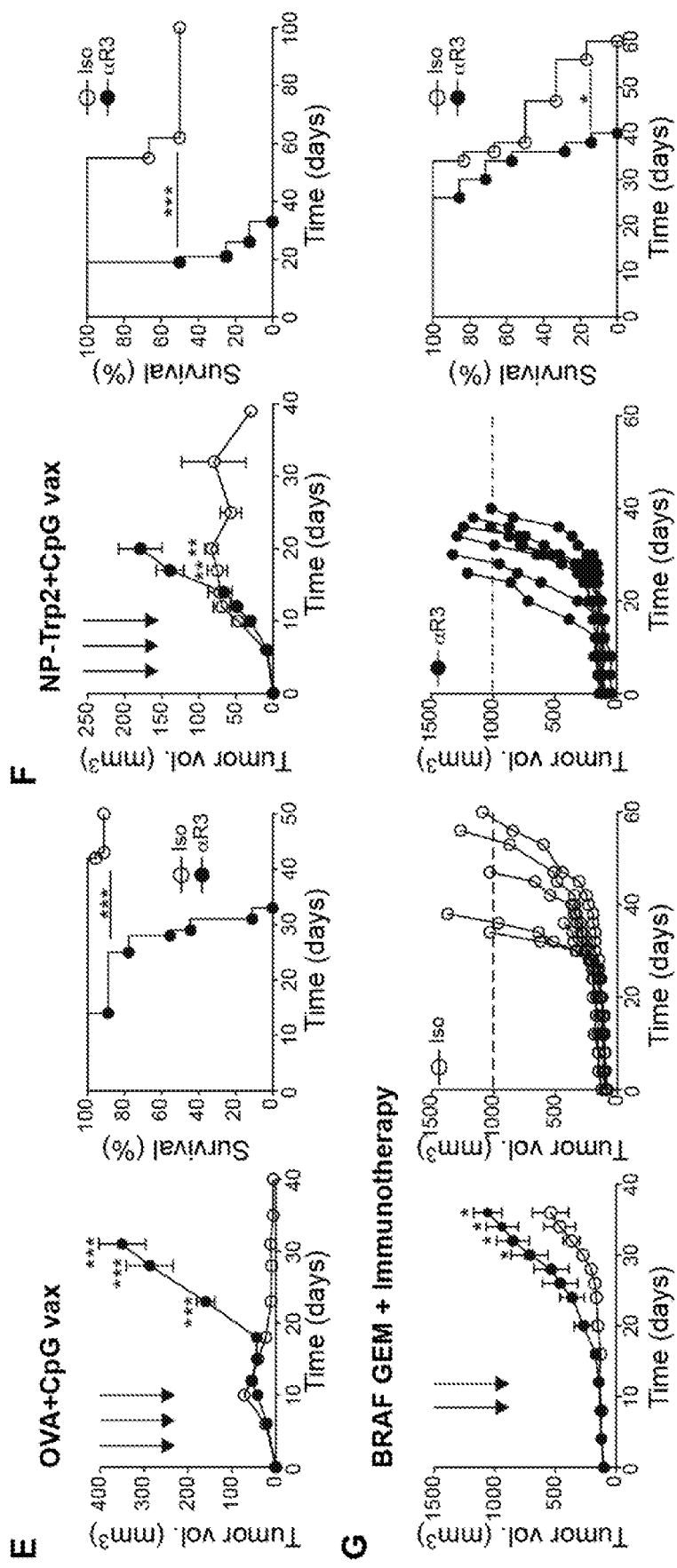
FIG. 11E-G

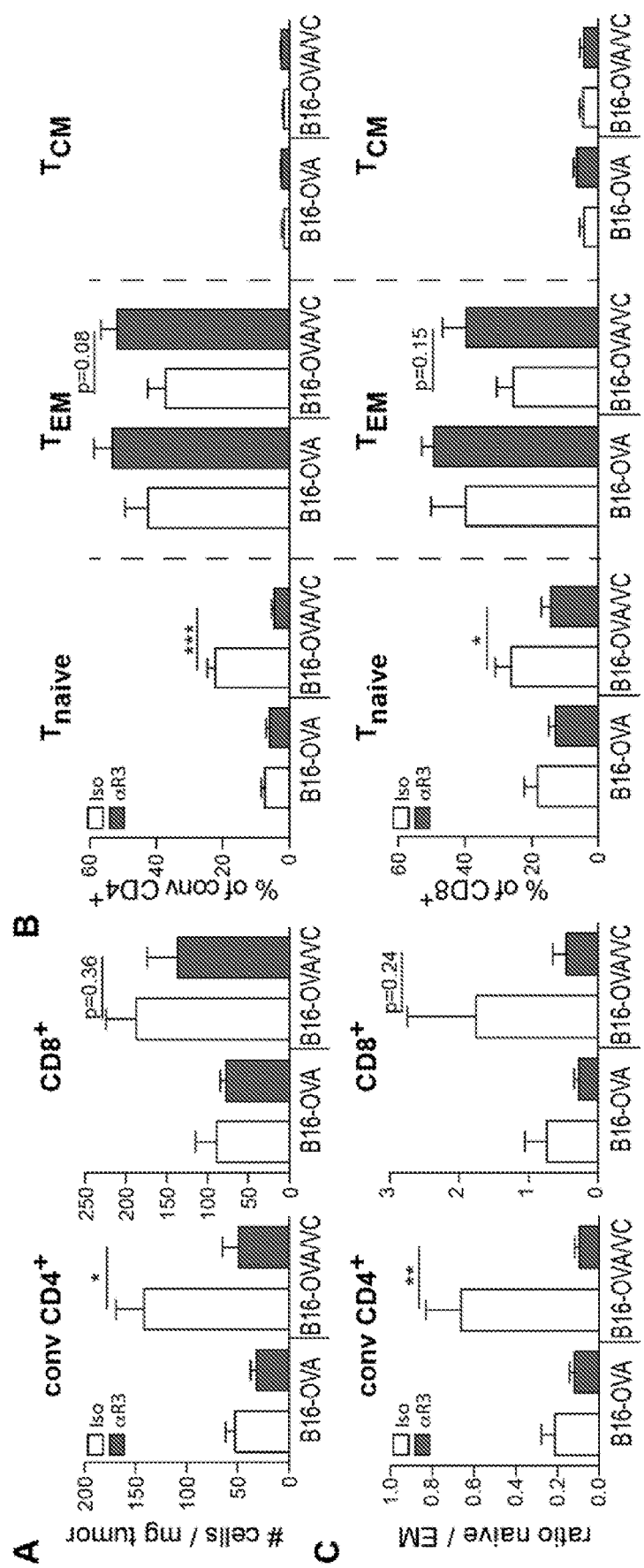
FIG. 12A-C

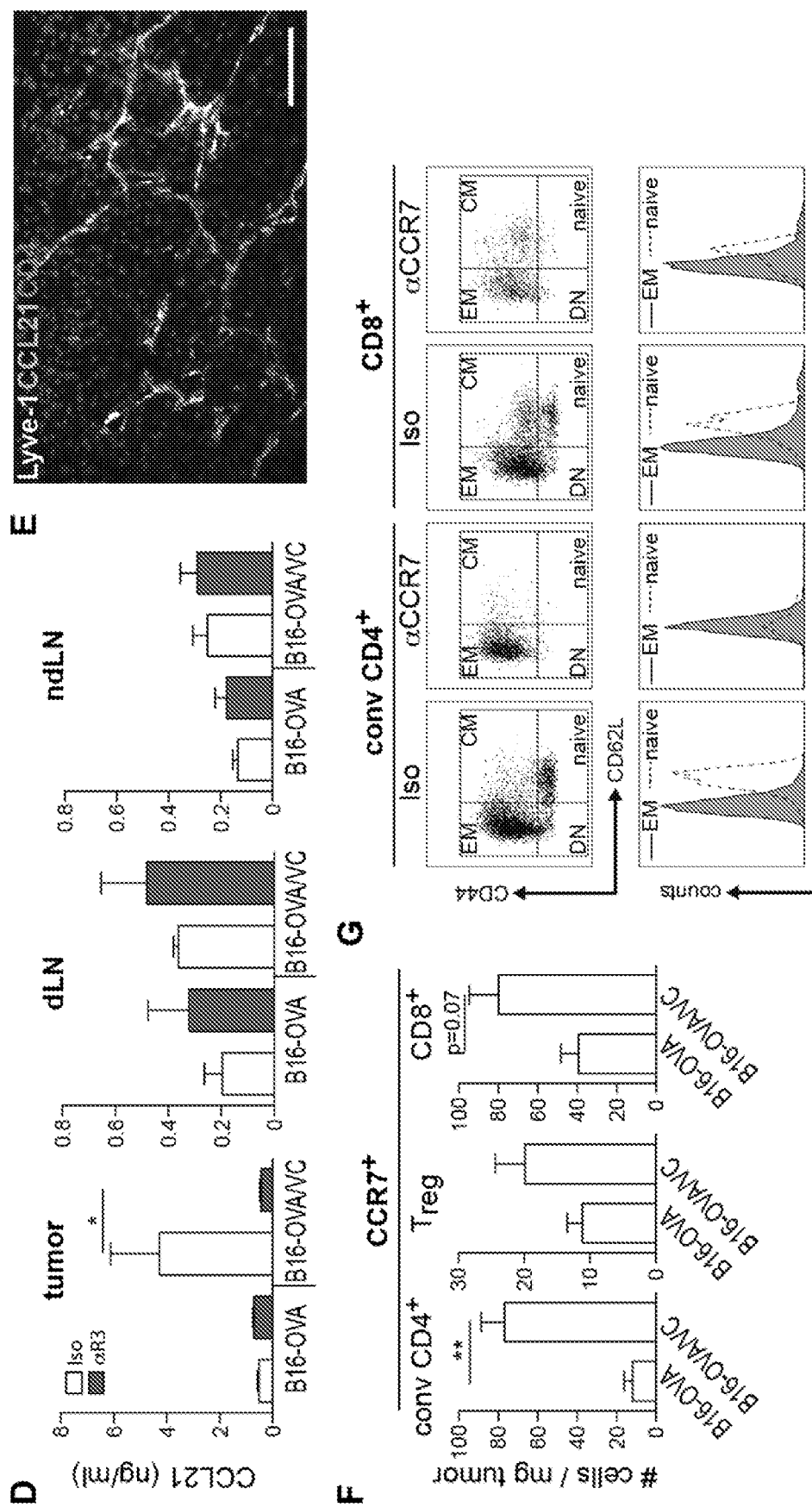
FIG. 12D-G

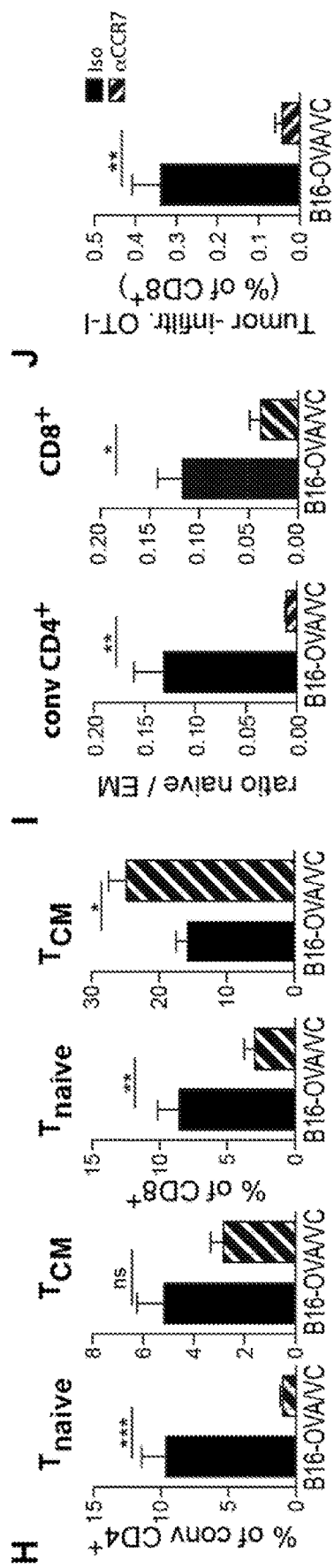
FIG. 12H-J

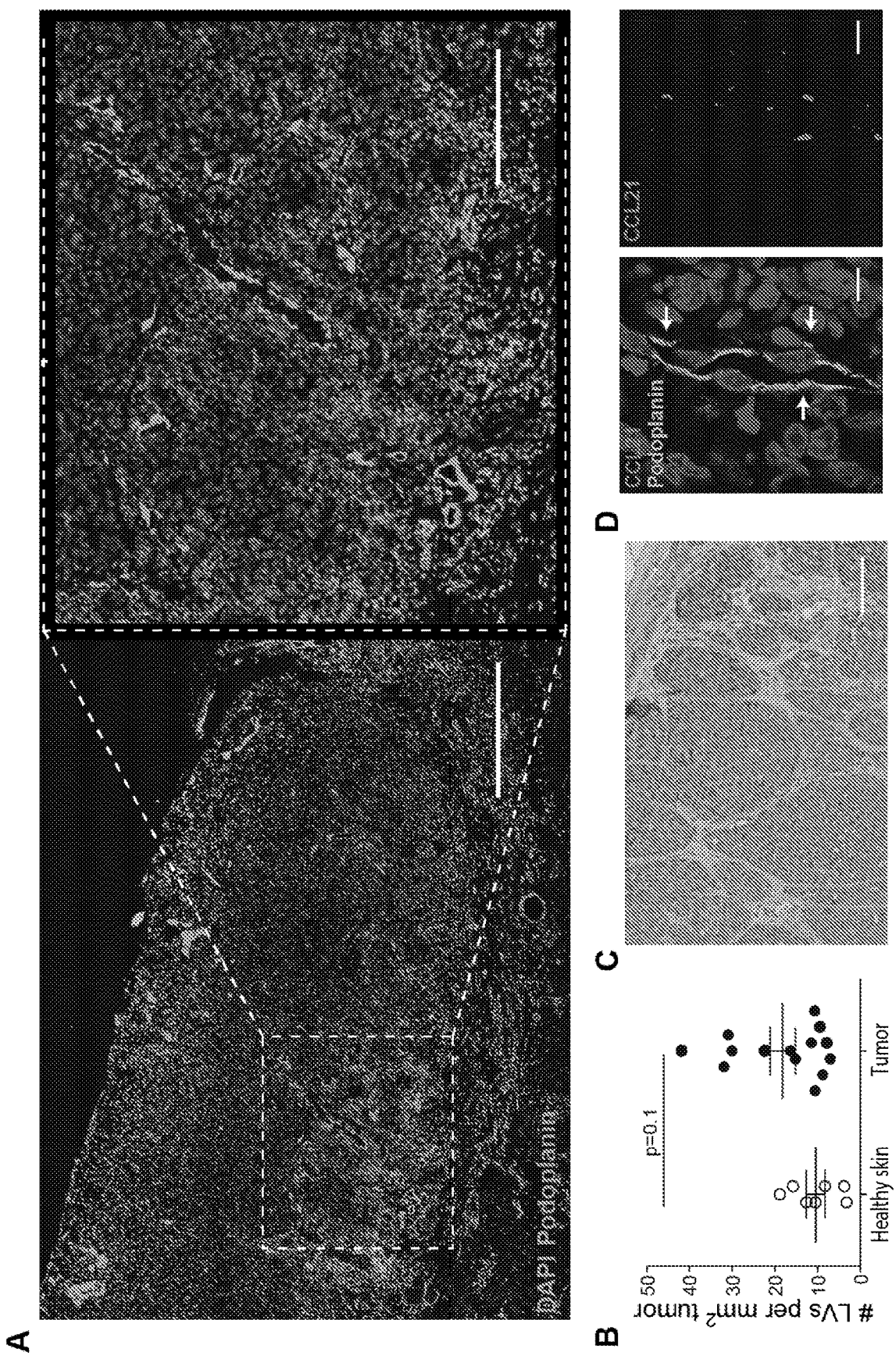
FIG. 13A-D

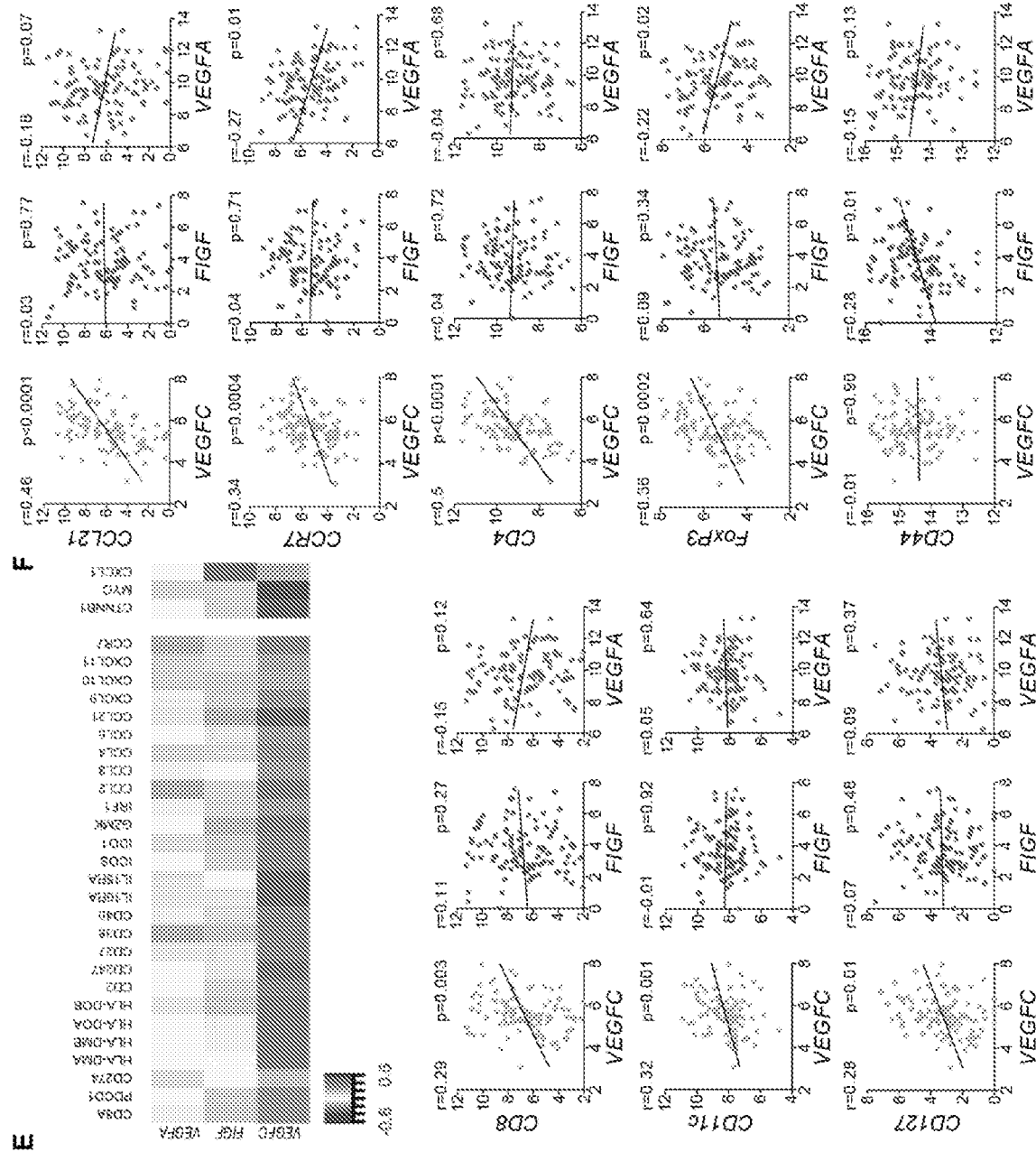
FIG. 13E-F

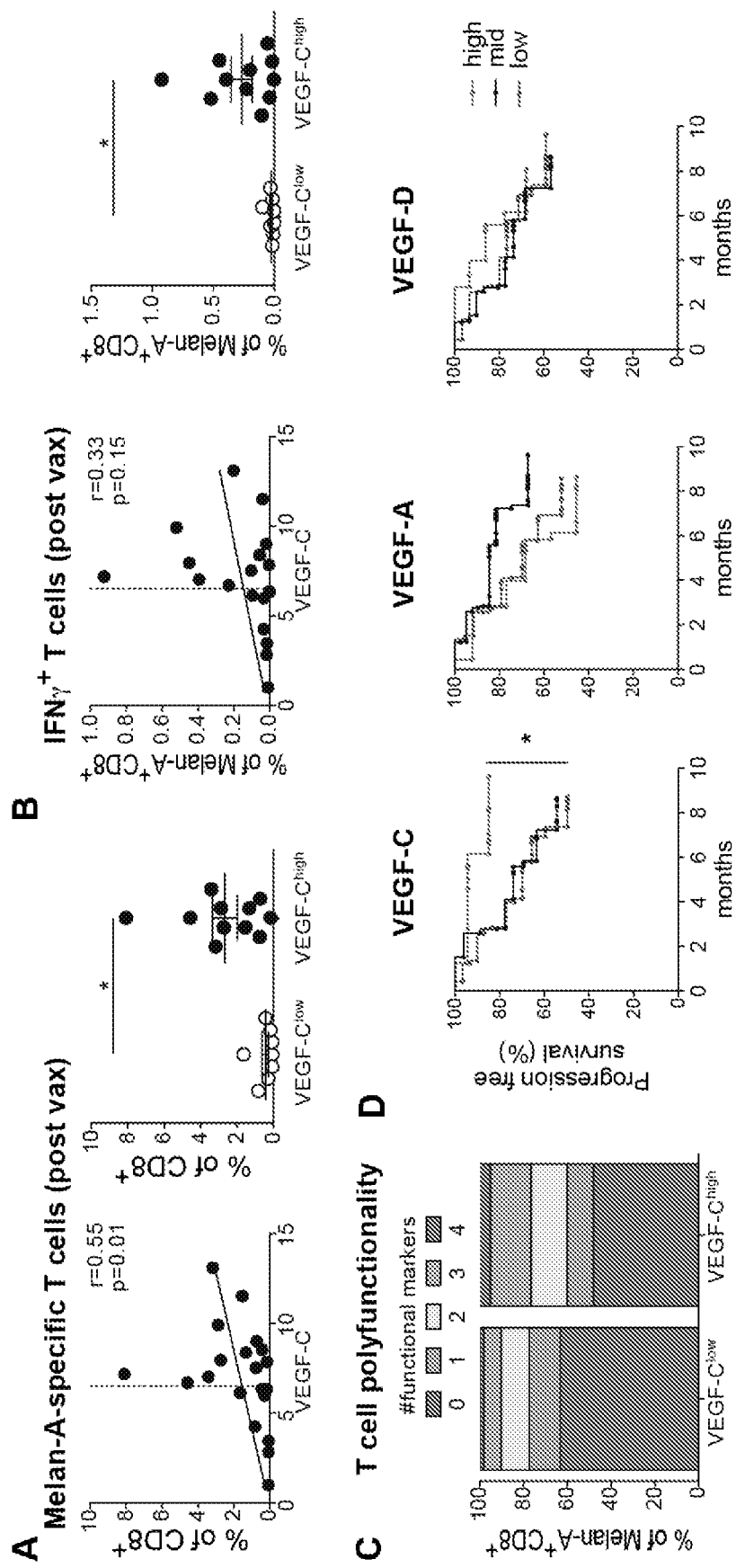
FIG. 14A-D

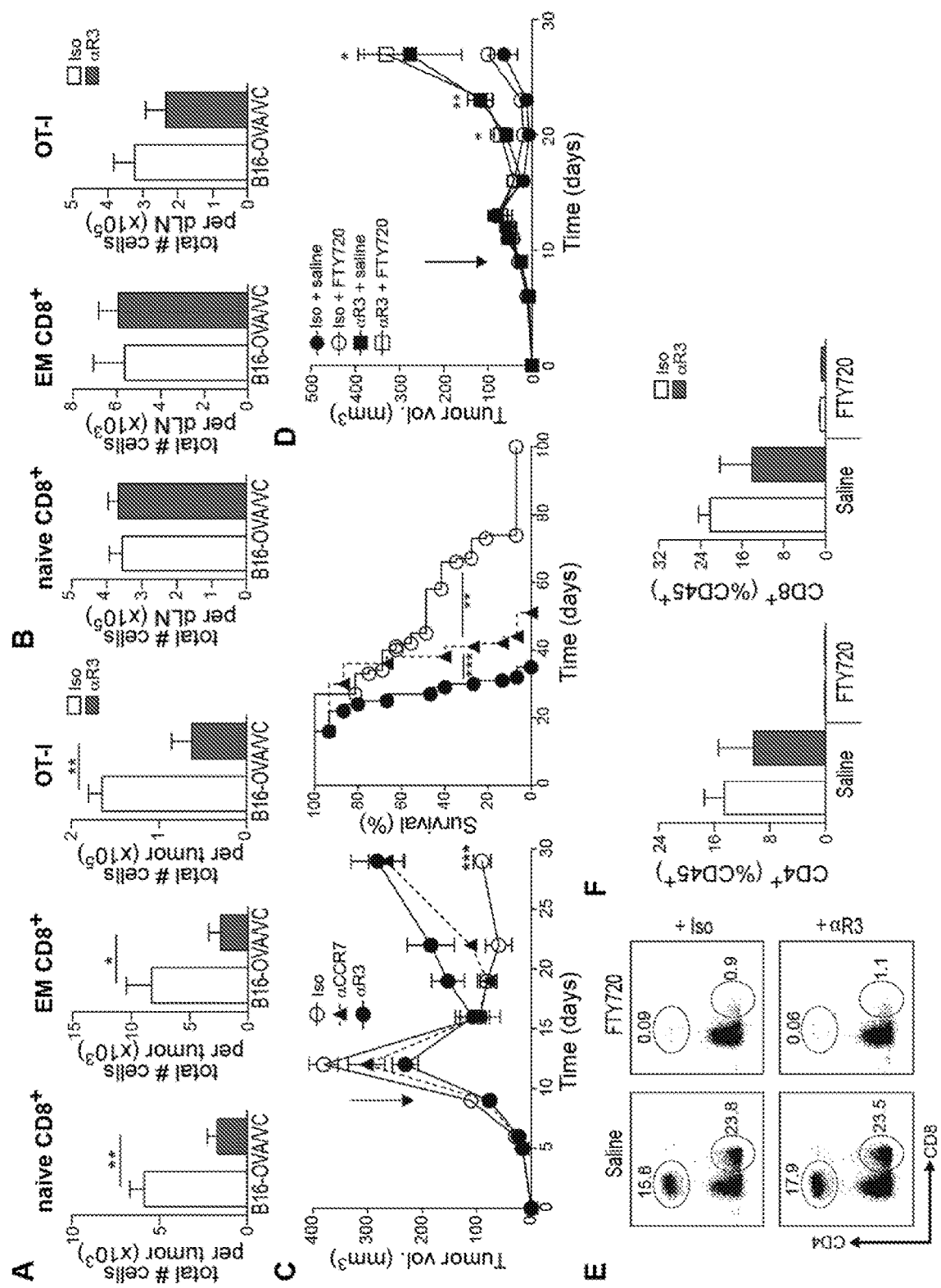
FIG. 15A-F

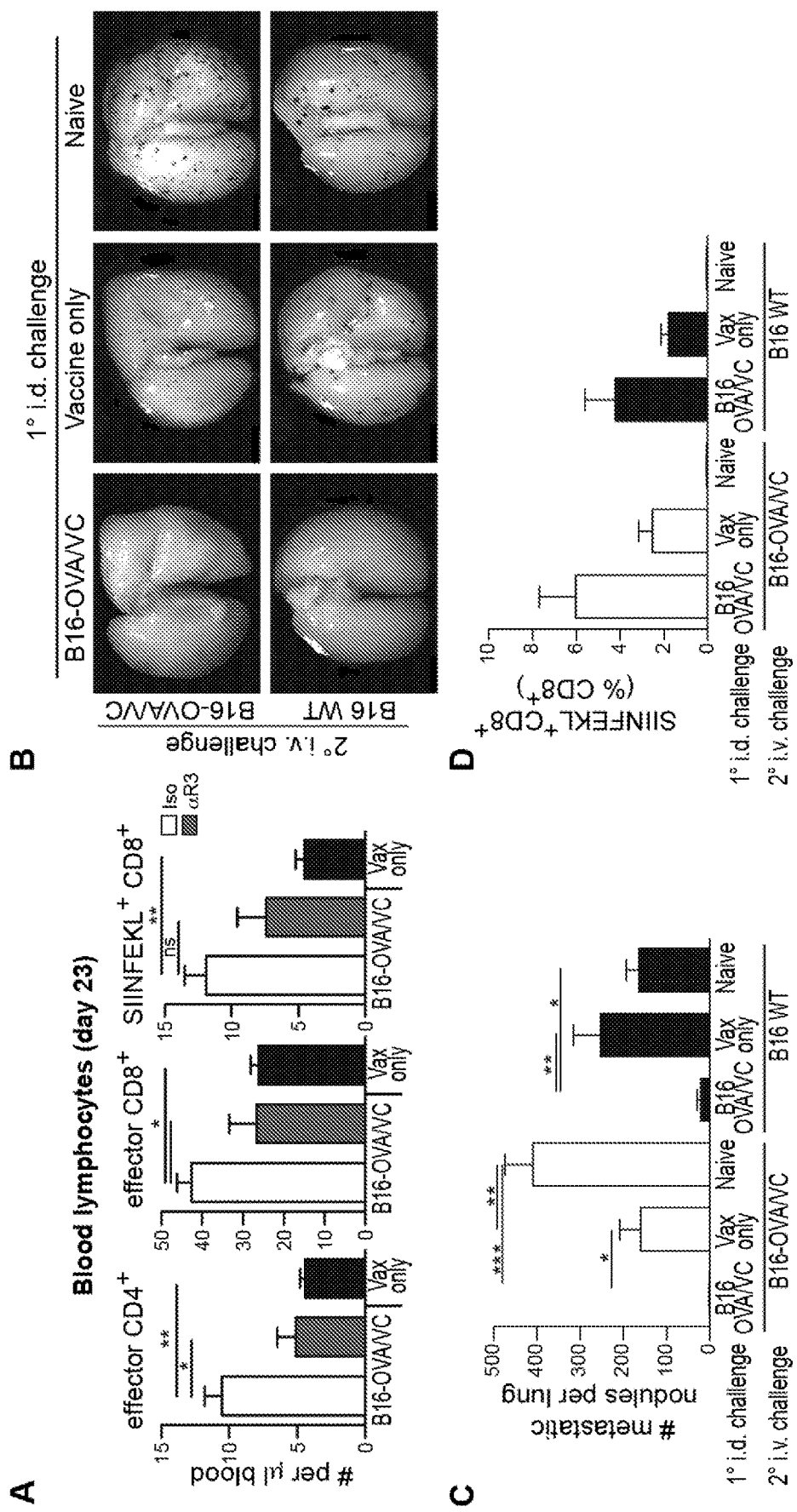
FIG. 16A-D

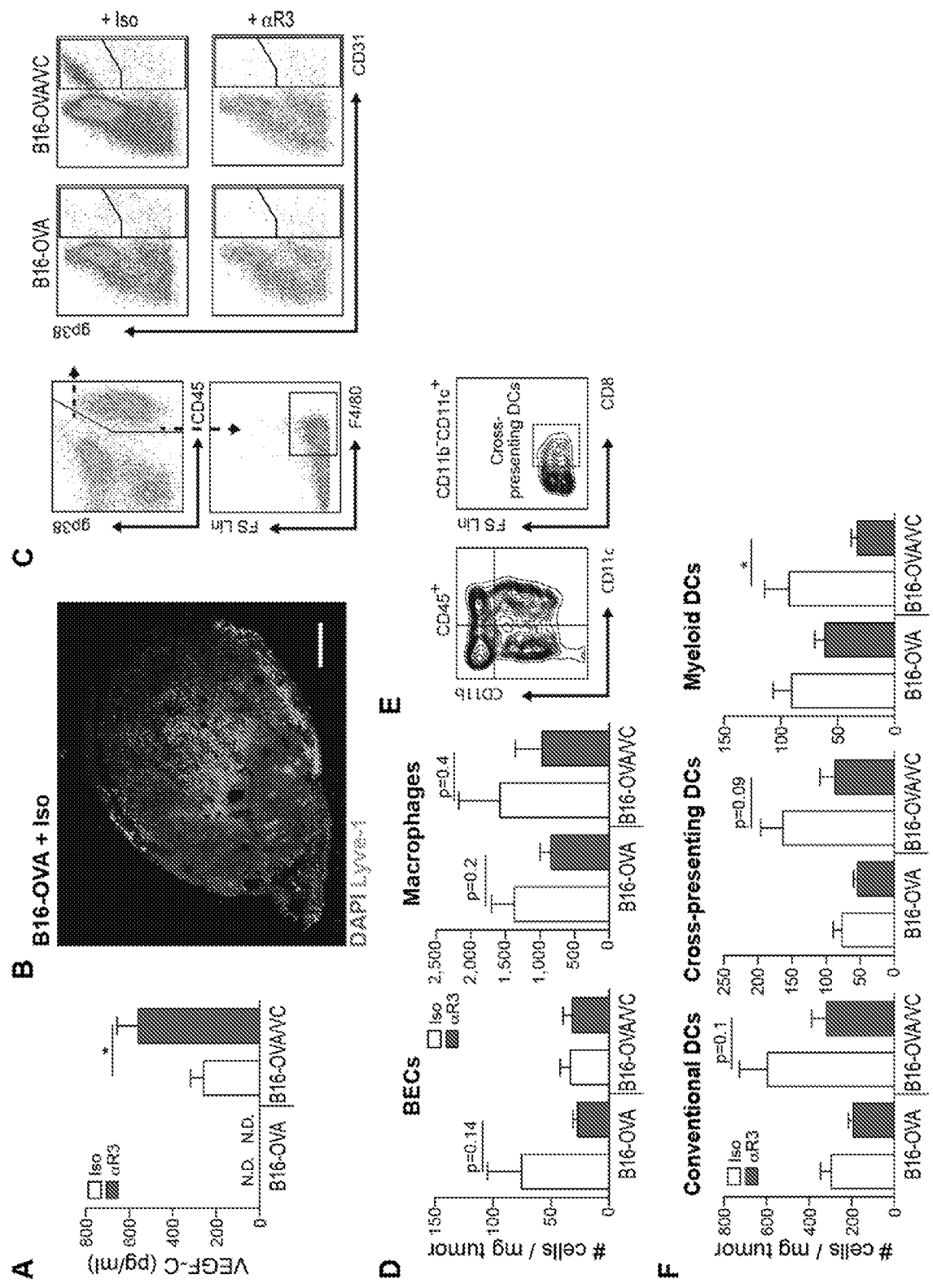
FIG. 17A-F

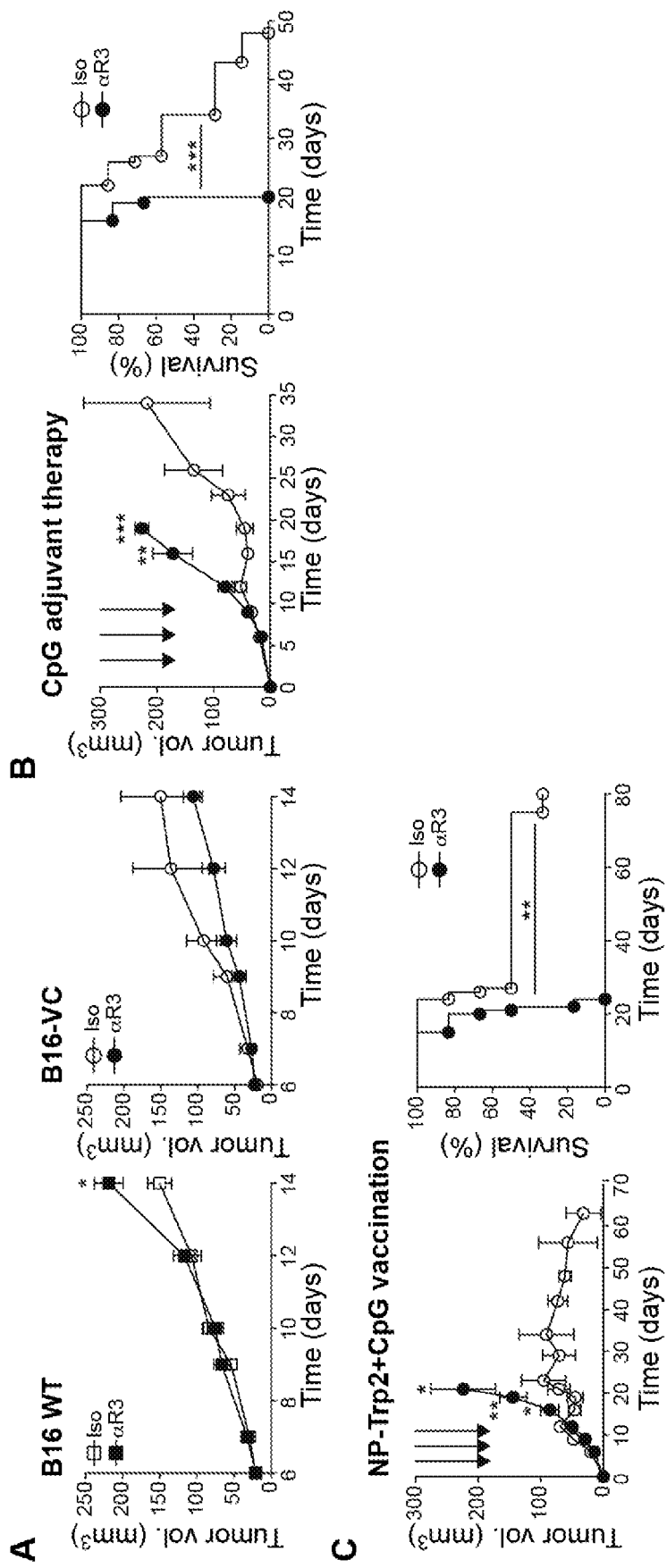
FIG. 18A-C

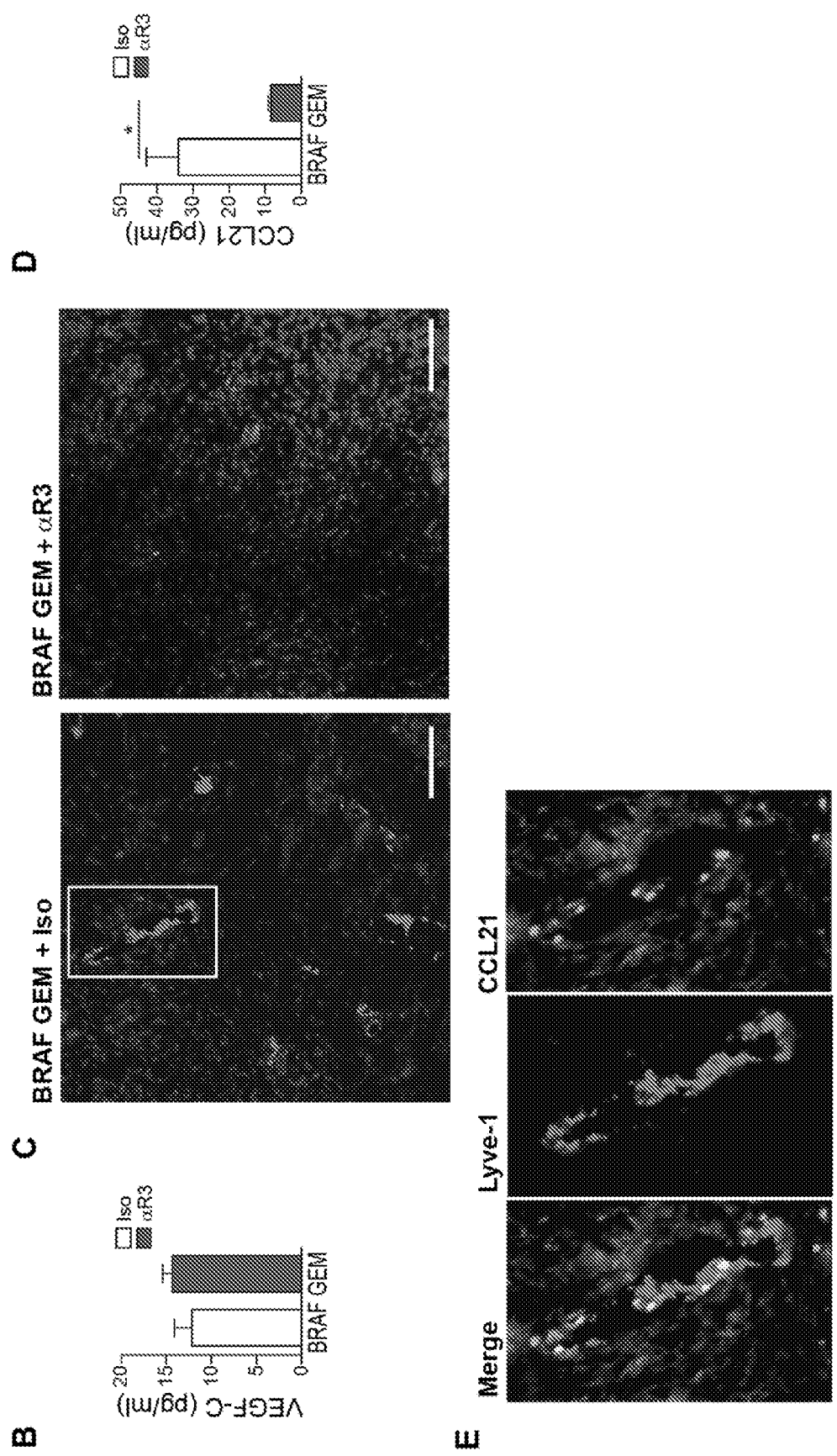
FIG. 19B-E

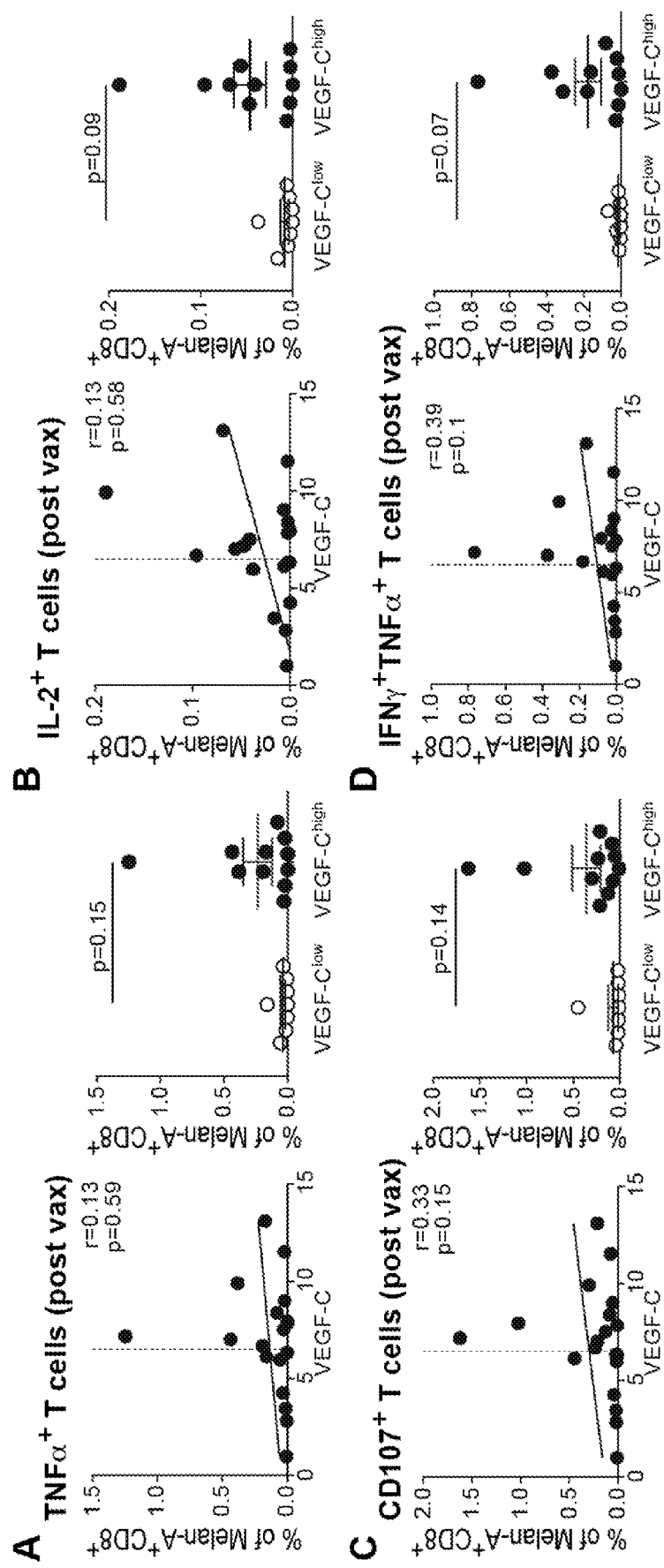
FIG. 21A-D

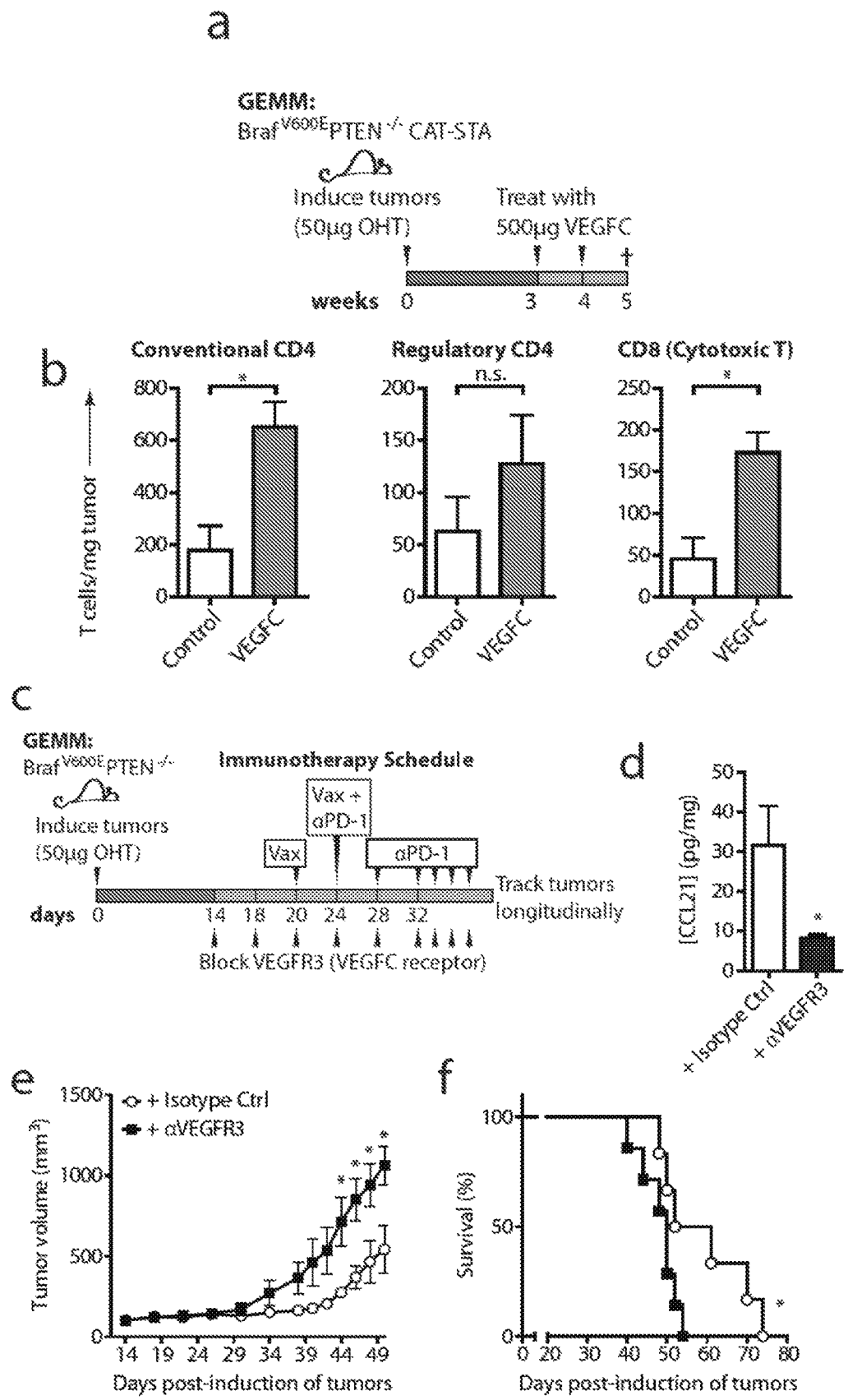
FIG. 22A-F

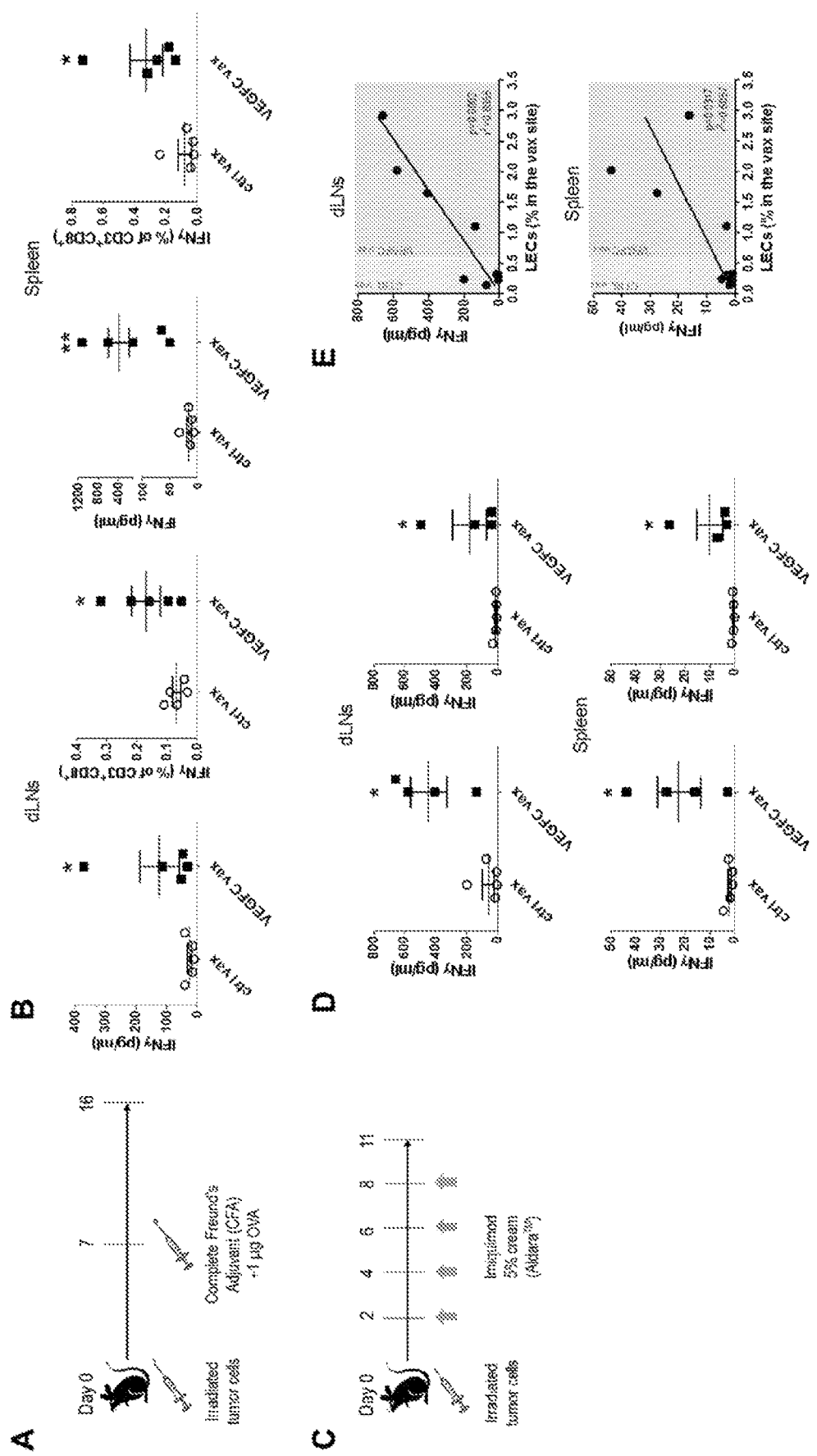
FIG. 23A-E

SEQUENCE LISTING

```
<160> NUMBER OF SEQ ID NOS: 20

<210> SEQ ID NO 1
<211> LENGTH: 419
<212> TYPE: PRT
<213> ORGANISM: Homo sapiens

<400> SEQUENCE: 1

Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
            20                  25                  30

Glu Ser Gly Leu Asp Leu Ser Asp Ala Glu Pro Asp Ala Gly Glu Ala
        35                  40                  45

Thr Ala Tyr Ala Ser Lys Asp Leu Glu Glu Gln Leu Arg Ser Val Ser
    50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
```

|  | | | | 115 | | | | 120 | | | | 125 | | |
|---|---|---|---|---|---|---|---|---|---|---|---|---|---|---|

Thr Gln Cys Met Pro Arg Glu Val Cys Ile Asp Val Gly Lys Glu Phe
130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
    210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
        275                 280                 285

Glu Thr Cys Gln Cys Val Cys Arg Ala Gly Leu Arg Pro Ala Ser Cys
    290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
        355                 360                 365

Cys Leu Leu Lys Gly Lys Lys Phe His His Gln Thr Cys Ser Cys Tyr
    370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser

<210> SEQ ID NO 2
<211> LENGTH: 415
<212> TYPE: PRT
<213> ORGANISM: Mus musculus

<400> SEQUENCE: 2

Met His Leu Leu Cys Phe Leu Ser Leu Ala Cys Ser Leu Leu Ala Ala
1               5                   10                  15

Ala Leu Ile Pro Ser Pro Arg Glu Ala Pro Ala Thr Val Ala Ala Phe
            20                  25                  30

Glu Ser Gly Leu Gly Phe Ser Ala Glu Pro Asp Gly Gly Glu Val
        35                  40                  45

Lys Ala Phe Glu Gly Lys Asp Leu Glu Glu Gln Leu Arg Ser Val Ser
    50                  55                  60

Ser Val Asp Glu Leu Met Ser Val Leu Tyr Pro Asp Tyr Trp Lys Met 65                  70                  75                  80

Tyr Lys Cys Gln Leu Arg Lys Gly Gly Trp Gln Gln Pro Thr Leu Asn
                85                  90                  95

Thr Arg Thr Gly Asp Ser Val Lys Phe Ala Ala His Tyr Asn Thr
            100                 105                 110

Glu Ile Leu Lys Ser Ile Asp Asn Glu Trp Arg Lys Thr Gln Cys Met
            115                 120                 125

Pro Arg Glu Val Cys Ile Asp Val Gly Lys Glu Phe Gly Ala Ala Thr
        130                 135                 140

Asn Thr Phe Phe Lys Pro Pro Cys Val Ser Val Tyr Arg Cys Gly Gly
145                 150                 155                 160

Cys Cys Asn Ser Glu Gly Leu Gln Cys Met Asn Thr Ser Thr Gly Tyr
                165                 170                 175

Leu Ser Lys Thr Leu Phe Glu Ile Thr Val Pro Leu Ser Gln Gly Pro
            180                 185                 190

Lys Pro Val Thr Ile Ser Phe Ala Asn His Thr Ser Cys Arg Cys Met
        195                 200                 205

Ser Lys Leu Asp Val Tyr Arg Gln Val His Ser Ile Ile Arg Arg Ser
    210                 215                 220

Leu Pro Ala Thr Leu Pro Gln Cys Gln Ala Ala Asn Lys Thr Cys Pro
225                 230                 235                 240

Thr Asn Tyr Val Trp Asn Asn Tyr Met Cys Arg Cys Leu Ala Gln Gln
                245                 250                 255

Asp Phe Ile Phe Tyr Ser Asn Val Glu Asp Asp Ser Thr Asn Gly Phe
            260                 265                 270

His Asp Val Cys Gly Pro Asn Lys Glu Leu Asp Glu Asp Thr Cys Gln
        275                 280                 285

Cys Val Cys Lys Gly Gly Leu Arg Pro Ser Ser Cys Gly Pro His Lys
    290                 295                 300

Glu Leu Asp Arg Asp Ser Cys Gln Cys Val Cys Lys Asn Lys Leu Phe
305                 310                 315                 320

Pro Asn Ser Cys Gly Ala Asn Arg Glu Phe Asp Glu Asn Thr Cys Gln
                325                 330                 335

Cys Val Cys Lys Arg Thr Cys Pro Arg Asn Gln Pro Leu Asn Pro Gly
            340                 345                 350

Lys Cys Ala Cys Glu Cys Thr Glu Asn Thr Gln Lys Cys Phe Leu Lys
        355                 360                 365

Gly Lys Lys Phe His His Gln Thr Cys Ser Cys Tyr Arg Arg Pro Cys
    370                 375                 380

Ala Asn Arg Leu Lys His Cys Asp Pro Gly Leu Ser Phe Ser Glu Glu
385                 390                 395                 400

Val Cys Arg Cys Val Pro Ser Tyr Trp Lys Arg Pro His Leu Asn
                405                 410                 415

<210> SEQ ID NO 3
<211> LENGTH: 354
<212> TYPE: PRT
<213> ORGANISM: Homo sapiens

<400> SEQUENCE: 3

Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

```
Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
 50                  55                  60

Trp Arg Cys Arg Leu Arg Leu Lys Ser Phe Thr Ser Met Asp Ser Arg
 65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
    130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
        275                 280                 285

Ser Cys Phe Glu Cys Lys Glu Ser Leu Glu Thr Cys Cys Gln Lys His
    290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
            340                 345                 350

Asn Pro

<210> SEQ ID NO 4
<211> LENGTH: 358
<212> TYPE: PRT
<213> ORGANISM: Mus musculus

<400> SEQUENCE: 4

Met Tyr Gly Glu Trp Gly Met Gly Asn Ile Leu Met Met Phe His Val
 1               5                  10                  15

Tyr Leu Val Gln Gly Phe Arg Ser Glu His Gly Pro Val Lys Asp Phe
                20                  25                  30

Ser Phe Glu Arg Ser Ser Arg Ser Met Leu Glu Arg Ser Glu Gln Gln
            35                  40                  45
```

```
Ile Arg Ala Ala Ser Ser Leu Glu Glu Leu Leu Gln Ile Ala His Ser
 50                  55                  60

Glu Asp Trp Lys Leu Trp Arg Cys Arg Leu Lys Leu Lys Ser Leu Ala
 65                  70                  75                  80

Ser Met Asp Ser Arg Ser Ala Ser His Arg Ser Thr Arg Phe Ala Ala
                 85                  90                  95

Thr Phe Tyr Asp Thr Glu Thr Leu Lys Val Ile Asp Glu Glu Trp Gln
            100                 105                 110

Arg Thr Gln Cys Ser Pro Arg Glu Thr Cys Val Glu Val Ala Ser Glu
        115                 120                 125

Leu Gly Lys Thr Thr Asn Thr Phe Phe Lys Pro Pro Cys Val Asn Val
130                 135                 140

Phe Arg Cys Gly Gly Cys Cys Asn Glu Glu Gly Val Met Cys Met Asn
145                 150                 155                 160

Thr Ser Thr Ser Tyr Ile Ser Lys Gln Leu Phe Glu Ile Ser Val Pro
                165                 170                 175

Leu Thr Ser Val Pro Glu Leu Val Pro Val Lys Ile Ala Asn His Thr
            180                 185                 190

Gly Cys Lys Cys Leu Pro Thr Gly Pro Arg His Pro Tyr Ser Ile Ile
        195                 200                 205

Arg Arg Ser Ile Gln Thr Pro Glu Glu Asp Glu Cys Pro His Ser Lys
210                 215                 220

Lys Leu Cys Pro Ile Asp Met Leu Trp Asp Asn Thr Lys Cys Lys Cys
225                 230                 235                 240

Val Leu Gln Asp Glu Thr Pro Leu Pro Gly Thr Glu Asp His Ser Tyr
                245                 250                 255

Leu Gln Glu Pro Thr Leu Cys Gly Pro His Met Thr Phe Asp Glu Asp
            260                 265                 270

Arg Cys Glu Cys Val Cys Lys Ala Pro Cys Pro Gly Asp Leu Ile Gln
        275                 280                 285

His Pro Glu Asn Cys Ser Cys Phe Glu Cys Lys Glu Ser Leu Glu Ser
290                 295                 300

Cys Cys Gln Lys His Lys Ile Phe His Pro Asp Thr Cys Ser Cys Glu
305                 310                 315                 320

Asp Arg Cys Pro Phe His Thr Arg Thr Cys Ala Ser Arg Lys Pro Ala
                325                 330                 335

Cys Gly Lys His Trp Arg Phe Pro Lys Glu Thr Arg Ala Gln Gly Leu
            340                 345                 350

Tyr Ser Gln Glu Asn Pro
        355

<210> SEQ ID NO 5
<211> LENGTH: 134
<212> TYPE: PRT
<213> ORGANISM: Artificial Sequence
<220> FEATURE:
<223> OTHER INFORMATION: Synthetic Peptide

<400> SEQUENCE: 5

Met Ala Gln Ser Leu Ala Leu Ser Leu Leu Ile Leu Val Leu Ala Phe
 1               5                  10                  15

Gly Ile Pro Arg Thr Gln Gly Ser Asp Gly Gly Ala Gln Asp Cys Cys
                 20                  25                  30

Leu Lys Tyr Ser Gln Arg Lys Ile Pro Ala Lys Val Val Arg Ser Tyr
            35                  40                  45
```

```
Arg Lys Gln Glu Pro Ser Leu Gly Cys Ser Ile Pro Ala Ile Leu Phe
 50                  55                  60

Leu Pro Arg Lys Arg Ser Gln Ala Glu Leu Cys Ala Asp Pro Lys Glu
 65                  70                  75                  80

Leu Trp Val Gln Gln Leu Met Gln His Leu Asp Lys Thr Pro Ser Pro
                 85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
            115                 120                 125

Gln Thr Pro Lys Gly Pro
    130
```

```
<210> SEQ ID NO 6
<211> LENGTH: 133
<212> TYPE: PRT
<213> ORGANISM: Artificial Sequence
<220> FEATURE:
<223> OTHER INFORMATION: Synthetic Peptide

<400> SEQUENCE: 6

Met Ala Gln Met Met Thr Leu Ser Leu Leu Ser Leu Val Leu Ala Leu
 1               5                  10                  15

Cys Ile Pro Trp Thr Gln Gly Ser Asp Gly Gly Gln Asp Cys Cys
                 20                  25                  30

Leu Lys Tyr Ser Gln Lys Lys Ile Pro Tyr Ser Ile Val Arg Gly Tyr
             35                  40                  45

Arg Lys Gln Glu Pro Ser Leu Gly Cys Pro Ile Pro Ala Ile Leu Phe
 50                  55                  60

Leu Pro Arg Lys His Ser Lys Pro Glu Leu Cys Ala Asn Pro Glu Glu
 65                  70                  75                  80

Gly Trp Val Gln Asn Leu Met Arg Arg Leu Asp Gln Pro Pro Ala Pro
                 85                  90                  95

Gly Lys Gln Ser Pro Gly Cys Arg Lys Asn Arg Gly Thr Ser Lys Ser
            100                 105                 110

Gly Lys Lys Gly Lys Gly Ser Lys Gly Cys Lys Arg Thr Glu Gln Thr
            115                 120                 125

Gln Pro Ser Arg Gly
    130
```

```
<210> SEQ ID NO 7
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 7

Met His Leu Leu Gly Phe Phe Ser Val Ala Cys Ser Leu Leu Ala Ala
 1               5                  10                  15

Ala Leu Leu Pro Gly Pro Arg Glu Ala Pro Ala Ala Ala Ala
             20                  25                  30
```

```
<210> SEQ ID NO 8
<211> LENGTH: 80
<212> TYPE: PRT
<213> ORGANISM: Artificial Sequence
<220> FEATURE:
<223> OTHER INFORMATION: Synthetic Peptide
```

<400> SEQUENCE: 8

Phe Glu Ser Gly Leu Asp Leu Ser Asp Ala Glu Pro Asp Ala Gly Glu
1               5                   10                  15

Ala Thr Ala Tyr Ala Ser Lys Asp Leu Glu Glu Gln Leu Arg Ser Val
            20                  25                  30

Ser Ser Val Asp Glu Leu Met Thr Val Leu Tyr Pro Glu Tyr Trp Lys
        35                  40                  45

Met Tyr Lys Cys Gln Leu Arg Lys Gly Gly Trp Gln His Asn Arg Glu
    50                  55                  60

Gln Ala Asn Leu Asn Ser Arg Thr Glu Glu Thr Ile Lys Phe Ala Ala
65                  70                  75                  80

<210> SEQ ID NO 9
<211> LENGTH: 192
<212> TYPE: PRT
<213> ORGANISM: Artificial Sequence
<220> FEATURE:
<223> OTHER INFORMATION: Synthetic Peptide

<400> SEQUENCE: 9

Ser Leu Pro Ala Thr Leu Pro Gln Cys Gln Ala Ala Asn Lys Thr Cys
1               5                   10                  15

Pro Thr Asn Tyr Met Trp Asn Asn His Ile Cys Arg Cys Leu Ala Gln
            20                  25                  30

Glu Asp Phe Met Phe Ser Ser Asp Ala Gly Asp Asp Ser Thr Asp Gly
        35                  40                  45

Phe His Asp Ile Cys Gly Pro Asn Lys Glu Leu Asp Glu Glu Thr Cys
    50                  55                  60

Gln Cys Val Cys Arg Ala Gly Leu Arg Pro Ala Ser Cys Gly Pro His
65                  70                  75                  80

Lys Glu Leu Asp Arg Asn Ser Cys Gln Cys Val Cys Lys Asn Lys Leu
                85                  90                  95

Phe Pro Ser Gln Cys Gly Ala Asn Arg Glu Phe Asp Glu Asn Thr Cys
            100                 105                 110

Gln Cys Val Cys Lys Arg Thr Cys Pro Arg Asn Gln Pro Leu Asn Pro
        115                 120                 125

Gly Lys Cys Ala Cys Glu Cys Thr Glu Ser Pro Gln Lys Cys Leu Leu
    130                 135                 140

Lys Gly Lys Lys Phe His His Gln Thr Cys Ser Cys Tyr Arg Arg Pro
145                 150                 155                 160

Cys Thr Asn Arg Gln Lys Ala Cys Glu Pro Gly Phe Ser Tyr Ser Glu
                165                 170                 175

Glu Val Cys Arg Cys Val Pro Ser Tyr Trp Lys Arg Pro Gln Met Ser
            180                 185                 190

<210> SEQ ID NO 10
<211> LENGTH: 140
<212> TYPE: PRT
<213> ORGANISM: Artificial Sequence
<220> FEATURE:
<223> OTHER INFORMATION: Synthetic Peptide

<400> SEQUENCE: 10

Cys Gly Pro Asn Lys Glu Leu Asp Glu Glu Thr Cys Gln Cys Val Cys
1               5                   10                  15

Arg Ala Gly Leu Arg Pro Ala Ser Cys Gly Pro His Lys Glu Leu Asp
            20                  25                  30

```
Arg Asn Ser Cys Gln Cys Val Cys Lys Asn Lys Leu Phe Pro Ser Gln
         35                  40                  45

Cys Gly Ala Asn Arg Glu Phe Asp Glu Asn Thr Cys Gln Cys Val Cys
 50                  55                  60

Lys Arg Thr Cys Pro Arg Asn Gln Pro Leu Asn Pro Gly Lys Cys Ala
 65                  70                  75                  80

Cys Glu Cys Thr Glu Ser Pro Gln Lys Cys Leu Leu Lys Gly Lys Lys
             85                  90                  95

Phe His His Gln Thr Cys Ser Cys Tyr Arg Arg Pro Cys Thr Asn Arg
                100                 105                 110

Gln Lys Ala Cys Glu Pro Gly Phe Ser Tyr Ser Glu Glu Val Cys Arg
             115                 120                 125

Cys Val Pro Ser Tyr Trp Lys Arg Pro Gln Met Ser
130                 135                 140

<210> SEQ ID NO 11
<211> LENGTH: 83
<212> TYPE: PRT
<213> ORGANISM: Artificial Sequence
<220> FEATURE:
<223> OTHER INFORMATION: Synthetic Peptide

<400> SEQUENCE: 11

Cys Gly Pro Asn Lys Glu Leu Asp Glu Thr Cys Gln Cys Val Cys
 1               5                  10                  15

Arg Ala Gly Leu Arg Pro Ala Ser Cys Gly Pro His Lys Glu Leu Asp
                 20                  25                  30

Arg Asn Ser Cys Gln Cys Val Cys Lys Asn Lys Leu Phe Pro Ser Gln
             35                  40                  45

Cys Gly Ala Asn Arg Glu Phe Asp Glu Asn Thr Cys Gln Cys Val Cys
 50                  55                  60

Lys Arg Thr Cys Pro Arg Asn Gln Pro Leu Asn Pro Gly Lys Cys Ala
 65                  70                  75                  80

Cys Glu Cys

<210> SEQ ID NO 12
<211> LENGTH: 116
<212> TYPE: PRT
<213> ORGANISM: Homo sapiens

<400> SEQUENCE: 12

Ala His Tyr Asn Thr Glu Ile Leu Lys Ser Ile Asp Asn Glu Trp Arg
 1               5                  10                  15

Lys Thr Gln Cys Met Pro Arg Glu Val Cys Ile Asp Val Gly Lys Glu
                 20                  25                  30

Phe Gly Val Ala Thr Asn Thr Phe Phe Lys Pro Pro Cys Val Ser Val
                 35                  40                  45

Tyr Arg Cys Gly Gly Cys Cys Asn Ser Glu Gly Leu Gln Cys Met Asn
 50                  55                  60

Thr Ser Thr Ser Tyr Leu Ser Lys Thr Leu Phe Glu Ile Thr Val Pro
 65                  70                  75                  80

Leu Ser Gln Gly Pro Lys Pro Val Thr Ile Ser Phe Ala Asn His Thr
                 85                  90                  95

Ser Cys Arg Cys Met Ser Lys Leu Asp Val Tyr Arg Gln Val His Ser
                100                 105                 110

Ile Ile Arg Arg
                115
```

```
<210> SEQ ID NO 13
<211> LENGTH: 109
<212> TYPE: PRT
<213> ORGANISM: Artificial Sequence
<220> FEATURE:
<223> OTHER INFORMATION: Synthetic Peptide

<400> SEQUENCE: 13

Ala His Tyr Asn Thr Glu Ile Leu Lys Ser Ile Asp Asn Glu Trp Arg
1               5                   10                  15

Lys Thr Gln Cys Met Pro Arg Glu Val Cys Ile Asp Val Gly Lys Glu
            20                  25                  30

Phe Gly Val Ala Thr Asn Thr Phe Phe Lys Pro Pro Cys Val Ser Val
        35                  40                  45

Tyr Arg Cys Gly Gly Cys Cys Asn Ser Glu Gly Leu Gln Cys Met Asn
    50                  55                  60

Thr Ser Thr Ser Tyr Leu Ser Lys Thr Leu Phe Glu Ile Thr Val Pro
65                  70                  75                  80

Leu Ser Gln Gly Pro Lys Pro Val Thr Ile Ser Phe Ala Asn His Thr
                85                  90                  95

Ser Cys Arg Cys Met Ser Lys Leu Asp Val Tyr Arg Gln
            100                 105

<210> SEQ ID NO 14
<211> LENGTH: 97
<212> TYPE: PRT
<213> ORGANISM: Artificial Sequence
<220> FEATURE:
<223> OTHER INFORMATION: Synthetic Peptide

<400> SEQUENCE: 14

Cys Pro Ile Asp Met Leu Trp Asp Ser Asn Lys Cys Lys Cys Val Leu
1               5                   10                  15

Gln Glu Glu Asn Pro Leu Ala Gly Thr Glu Asp His Ser His Leu Gln
            20                  25                  30

Glu Pro Ala Leu Cys Gly Pro His Met Met Phe Asp Glu Asp Arg Cys
        35                  40                  45

Glu Cys Val Cys Lys Thr Pro Cys Pro Lys Asp Leu Ile Gln His Pro
    50                  55                  60

Lys Asn Cys Ser Cys Phe Glu Cys Lys Glu Ser Leu Glu Thr Cys Cys
65                  70                  75                  80

Gln Lys His Lys Leu Phe His Pro Asp Thr Cys Ser Cys Glu Asp Arg
                85                  90                  95

Cys

<210> SEQ ID NO 15
<211> LENGTH: 117
<212> TYPE: PRT
<213> ORGANISM: Homo sapiens

<400> SEQUENCE: 15

Phe Ala Ala Thr Phe Tyr Asp Ile Glu Thr Leu Lys Val Ile Asp Glu
1               5                   10                  15

Glu Trp Gln Arg Thr Gln Cys Ser Pro Arg Glu Thr Cys Val Glu Val
            20                  25                  30

Ala Ser Glu Leu Gly Lys Ser Thr Asn Thr Phe Phe Lys Pro Pro Cys
        35                  40                  45
```

Val Asn Val Phe Arg Cys Gly Gly Cys Cys Asn Glu Glu Ser Leu Ile
 50                  55                  60

Cys Met Asn Thr Ser Thr Ser Tyr Ile Ser Lys Gln Leu Phe Glu Ile
 65                  70                  75                  80

Ser Val Pro Leu Thr Ser Val Pro Glu Leu Val Pro Val Lys Val Ala
                 85                  90                  95

Asn His Thr Gly Cys Lys Cys Leu Pro Thr Ala Pro Arg His Pro Tyr
             100                 105                 110

Ser Ile Ile Arg Arg
         115

<210> SEQ ID NO 16
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 16

Met Ala Gln Ser Leu Ala Leu Ser Leu Leu Ile Leu Val Leu Ala Phe
 1               5                  10                  15

Gly Ile Pro Arg Thr Gln Gly
             20

<210> SEQ ID NO 17
<211> LENGTH: 111
<212> TYPE: PRT
<213> ORGANISM: Artificial Sequence
<220> FEATURE:
<223> OTHER INFORMATION: Synthetic Peptide

<400> SEQUENCE: 17

Ser Asp Gly Gly Ala Gln Asp Cys Cys Leu Lys Tyr Ser Gln Arg Lys
 1               5                  10                  15

Ile Pro Ala Lys Val Val Arg Ser Tyr Arg Lys Gln Glu Pro Ser Leu
                 20                  25                  30

Gly Cys Ser Ile Pro Ala Ile Leu Phe Leu Pro Arg Lys Arg Ser Gln
             35                  40                  45

Ala Glu Leu Cys Ala Asp Pro Lys Glu Leu Trp Val Gln Gln Leu Met
 50                  55                  60

Gln His Leu Asp Lys Thr Pro Ser Pro Gln Lys Pro Ala Gln Gly Cys
 65                  70                  75                  80

Arg Lys Asp Arg Gly Ala Ser Lys Thr Gly Lys Lys Gly Lys Gly Ser
                 85                  90                  95

Lys Gly Cys Lys Arg Thr Glu Arg Ser Gln Thr Pro Lys Gly Pro
             100                 105                 110

<210> SEQ ID NO 18
<211> LENGTH: 134
<212> TYPE: PRT
<213> ORGANISM: Artificial Sequence
<220> FEATURE:
<223> OTHER INFORMATION: Synthetic Peptide

<400> SEQUENCE: 18

Met Ala Gln Ser Leu Ala Leu Ser Leu Leu Ile Leu Val Leu Ala Phe
 1               5                  10                  15

Gly Ile Pro Arg Thr Gln Gly Ser Asp Gly Gly Ala Gln Asp Cys Cys
                 20                  25                  30

Leu Lys Tyr Ser Gln Arg Lys Ile Pro Ala Lys Val Val Arg Ser Tyr

```
            35                  40                  45
Arg Lys Gln Glu Pro Ser Leu Gly Cys Ser Ile Pro Ala Ile Leu Phe
         50                  55                  60

Leu Pro Arg Lys Arg Ser Gln Ala Glu Leu Cys Ala Asp Pro Lys Glu
 65                  70                  75                  80

Leu Trp Val Gln Gln Leu Met Gln His Leu Asp Lys Thr Pro Ser Pro
                     85                  90                  95

Gln Lys Pro Ala Gln Gly Cys Arg Arg Arg Pro Lys Gly Arg Gly Lys
                100                 105                 110

Arg Arg Arg Glu Lys Gln Arg Lys Gly Cys Lys Arg Thr Glu Arg Ser
                115                 120                 125

Gln Thr Pro Lys Gly Pro
                130
```

```
<210> SEQ ID NO 19
<211> LENGTH: 156
<212> TYPE: PRT
<213> ORGANISM: Artificial Sequence
<220> FEATURE:
<223> OTHER INFORMATION: Synthetic Peptide

<400> SEQUENCE: 19

Met Ala Gln Ser Leu Ala Leu Ser Leu Leu Ile Leu Val Leu Ala Phe
  1               5                  10                  15

Gly Ile Pro Arg Thr Gln Gly Ser Asp Gly Gly Ala Gln Asp Cys Cys
                 20                  25                  30

Leu Lys Tyr Ser Gln Arg Lys Ile Pro Ala Lys Val Val Arg Ser Tyr
             35                  40                  45

Arg Lys Gln Glu Pro Ser Leu Gly Cys Ser Ile Pro Ala Ile Leu Phe
         50                  55                  60

Leu Pro Arg Lys Arg Ser Gln Ala Glu Leu Cys Ala Asp Pro Lys Glu
 65                  70                  75                  80

Leu Trp Val Gln Gln Leu Met Gln His Leu Asp Lys Thr Pro Ser Pro
                     85                  90                  95

Gln Lys Pro Ala Gln Gly Cys Arg Lys Asp Arg Gly Ala Ser Lys Thr
                100                 105                 110

Gly Lys Lys Gly Lys Gly Ser Lys Gly Cys Lys Arg Thr Glu Arg Ser
                115                 120                 125

Gln Thr Pro Lys Gly Pro Arg Arg Pro Lys Gly Arg Gly Lys Arg
                130                 135                 140

Arg Arg Glu Lys Gln Arg Pro Thr Asp Ala His Leu
145                 150                 155
```

```
<210> SEQ ID NO 20
<211> LENGTH: 133
<212> TYPE: PRT
<213> ORGANISM: Artificial Sequence
<220> FEATURE:
<223> OTHER INFORMATION: Synthetic Peptide

<400> SEQUENCE: 20

Met Ala Gln Met Met Thr Leu Ser Leu Leu Ser Leu Val Leu Ala Leu
  1               5                  10                  15

Cys Ile Pro Trp Thr Gln Gly Ser Asp Gly Gly Gly Gln Asp Cys Cys
                 20                  25                  30

Leu Lys Tyr Ser Gln Lys Lys Ile Pro Tyr Ser Ile Val Arg Gly Tyr
             35                  40                  45
```

-continued

```
Arg Lys Gln Glu Pro Ser Leu Gly Cys Pro Ile Pro Ala Ile Leu Phe
    50              55              60

Leu Pro Arg Lys His Ser Lys Pro Glu Leu Cys Ala Asn Pro Glu Glu
65              70              75              80

Gly Trp Val Gln Asn Leu Met Arg Arg Leu Asp Gln Pro Pro Ala Pro
            85              90              95

Gly Lys Gln Ser Pro Gly Cys Arg Lys Asn Arg Gly Thr Ser Lys Ser
            100             105             110

Gly Lys Lys Gly Lys Gly Ser Lys Gly Cys Lys Arg Thr Glu Gln Thr
        115             120             125

Gln Pro Ser Arg Gly
    130
```

METHOD FOR TREATING MELANOMA USING LYMPHANGIOGENESIS INDUCERS AND A MELANOMA-SPECIFIC ANTIGEN

CROSS-REFERENCE TO RELATED APPLICATIONS

This application is a national phase application under 35 U.S.C. § 371 of International Application No. PCT/US2017/030242 filed Apr. 28, 2017, which claims the benefit of priority of U.S. Provisional Patent Application No. 62/329,133 filed Apr. 28, 2016. The entire contents of each of the above-referenced disclosures are specifically incorporated herein by reference without disclaimer.

BACKGROUND OF THE INVENTION

1. Field of the Invention

The present invention relates generally to the field of immunology. More particularly, it concerns methods and compositions for evoking protective immune responses against pathogen infection or cancer comprising a lymphangiogenesis inducer and an antigen against which an immune response is desired.

2. Description of Related Art

Adaptive immune responses are induced in vivo by stimulation of T and B lymphocytes by antigen-presenting cells (APCs), most notably dendritic cells (DCs). Induction of antigen-specific immune responses is important in medical applications such as vaccination, where pathogen-derived antigens or recombinant or synthetic antigens are administered to the body in conjunction with adjuvant molecules to induce expansion of antigen-specific CD4 and CD8 T cells, expansion of antigen-specific B cells and differentiation into plasma cells, and production of antibodies (Bachmann, et al., 2010; Hubbell, et al., 2009; Moon, et al., 2012; Seder, et al., 2008). This is commonly accomplished by administering the antigen admixed with adjuvants such as alum, which is a non-specific immune activator, or with adjuvants such as biomolecular activators of Toll like receptors, such as monophosphoryl lipid A, gardiquimod, resiquimod, or CpG oligodeoxynucleotides, for example (Maisonneuve, et al., 2014; Scott et al., 2012). APCs such as DCs collect the antigens and present them to lymphocytes; under the influence of the adjuvant, the APCs present epitopes from the antigens with co-simulation, so as to induce an effector immune response (Banchereau & Steinman, 1998; Chen & Flies, 2013). In the effector phase, T and B lymphocytes expand, and in a memory phase, those cells populations contract and transition into memory T and B lymphocytes, capable of responding again rapidly upon re-exposure to the antigen (Sallusto, et al., 1999; Gerlach, et al., 2010; Wherry, et al., 2003; Kaech & Wherry, 2007; Dorner & Radbruch, 2007). Thus, in the classical understanding of adaptive immune responses, the DC plays a central role in coordinating response to antigens and inducing effector responses which then contract and mature into memory T and B cell responses.

Standard vaccination strategies target conventional APCs, such as DCs, and initiate an adaptive immune response through induction of an effector immune phase. Thus, the T cell populations that are antigen-specific expand, exhibiting activated and inflammatory behavior, and after some time, their populations contract, producing memory cells. Indeed, in prophylactic vaccination, the ultimate goal is to produce enough of these memory cells, since these are the cells that eventually respond to an antigenic challenge. In this sense, the initial effector response is not beneficial per se, but it is generally accepted that a strong effector phase response leads to a beneficial memory response, and the literature on vaccination judges strong effector phase responses as being harbingers of strong generation of memory cells (Kaech & Wherry, 2007; Sprent & Surh, 2001).

SUMMARY OF THE INVENTION

Methods and compositions are provided for treating cancer using VEGF-C and/or CCL21 in conjunction with an antigen against which an immune response is desired.

In certain embodiments a method of eliciting an immune response to an antigen in a subject comprising administering to the subject one or more lymphangiogenesis inducers and an effective amount of the antigen is provided. In some embodiments, one or more lymphangiogenesis inducers and/or antigens are administered. In specific embodiments, the lymphangiogenesis inducer is vascular endothelial growth factor C (VEGF-C) or vascular endothelial growth factor D (VEGF-D). In specific embodiments, the lymphangiogenesis inducers are vascular endothelial growth factor C (VEGF-C) and vascular endothelial growth factor D (VEGF-D). In certain embodiments VEGF-C is human VEGF-C. A human VEGF-C protein may comprise a sequence that is at least or at most 70%, 80%, 85%, 90%, 95%, 98%, 99% or 100% similar or identical to SEQ ID NO: 1 (or any range derivable therein) (UniProtKB #P49767; available on the world wide web at uniprot.org/uniprot/P49767. In other embodiments, VEGF-C is mouse VEGF-C A mouse VEGF-C protein may comprise a sequence that is at least or at most 70%, 80%, 85%, 90%, 95%, 98%, 99% or 100% similar or identical to SEQ ID NO: 2 (or any range derivable therein) (UniProtKB #P97953; available on the world wide web at uniprot.org/uniprot/P97953. In certain embodiments VEGF-D is human VEGF-D. A human VEGF-D protein may comprise a sequence that is at least or at most 70%, 80%, 85%, 90%, 95%, 98%, 99% or 100% similar or identical to SEQ ID NO: 3 (or any range derivable therein) (UniProtKB #O43915; available on the world wide web at uniprot.org/uniprot/O43915. In other embodiments, VEGF-D is mouse VEGF-D A mouse VEGF-D protein may comprise a sequence that is at least or at most 70%, 80%, 85%, 90%, 95%, 98%, 99% or 100% similar or identical to SEQ ID NO: 4 (or any range derivable therein) (UniProtKB #P97946; available on the world wide web at uniprot.org/uniprot/P97946.

In specific embodiments, the lymphangiogenesis inducer comprises CCL21. In specific embodiments, the lymphangiogenesis inducers are vascular endothelial growth factor C (VEGF-C) and CCL21. In some embodiments, the lymphangiogenesis inducer comprises VEGF-D and CCL21. In some embodiments, the lymphangiogensis inducer comprises VEGF-C, VEGF-D, and CCL21. In certain embodiments CCL21 is human CCL21. A human CCL21 protein may comprise a sequence that is at least or at most 70%, 80%, 85%, 90%, 95%, 98%, 99% or 100% similar or identical to SEQ ID NO: 5 (or any range derivable therein) (UniProtKB #O00585; available on the world wide web at uniprot.org/uniprot/O00585. In other embodiments, CCL21 is mouse CCL21. A mouse CCL21 protein may comprise a sequence that is at least or at most 70%, 80%, 85%, 90%, 95%, 98%, 99% or 100% similar or identical to SEQ ID NO: 6 (or any range derivable therein) (UniProtKB #P86792; available on the world wide web at uniprot.org/uniprot/P86792.

The lymphangiogenesis inducer may be wild-type protein or truncated protein. In some embodiments, the lymphangiogenesis inducer is released in a controlled-release device or polymer. In some embodiments, the lymphangiogenesis induces is fused to or associated with a mistrix-binding sequence.

In some embodiments, the antigen comprises secreted exosomes from the patient's tumor cells. In some embodiments, the method further comprises obtaining a tumor cell sample from the patient. In some embodiments, the method further comprises isolating exosomes from the sample from the patient. In some embodiments, the antigen comprises irradiated tumor cells, tumor lysate, or antigens described herein.

Similar polypeptides, peptides and proteins, in some embodiments, are limited to those proteinaceous compounds whose substitutions are only with conservative amino acids. In other embodiments, only conservative substitutions are contemplated, while in others, deletions of nonessential amino acids or the addition of other amino acids in an area that is not involved in the compound's function are contemplated. In other embodiments, the antigen is a bacterial antigen, a viral antigen, a fungal antigen, a protozoal antigen, a helminth antigen or a cancer antigen. In still other aspects, the antigen is one or more bacterial antigens, one or more viral antigens, one or more fungal antigens, one or more protozoal antigens, one or more helminth antigens or one or more cancer antigens. In some aspects an antigen may be a biomolecule, a protein, a polypeptide, a carbohydrate, a polysaccharide, a lipid, a nucleic acid, a fatty acid, a glycolipid, a sterol, a polyterpene, a glycerolipid or a combination of these.

The polypeptides described herein may include 1, 2, 3, 4, 5, 6, 7, 8, 9, 10, 11, 12, 13, 14, 15, or more variant amino acids (or any range derivable therein) or be at least 70%, 80%, 85%, 90%, 95%, 98%, 99% or 100% similar or identical within at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of SEQ ID NO: 1-6. The contiguous amino acids may start at, include, or exclude amino acids starting at the N-terminus at positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, or 250 (or any length therein) in the polypeptide, such as of SEQ ID NO:1-6.

A polypeptide segment as described herein may include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of SEQ ID NO: 1-6.

In some embodiments, the lymphangiogenesis inducer or the antigen or both the lymphangiogenesis inducer and the antigen may be isolated. The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

In some embodiments, the subject is administered an antibacterial, antiviral, antifungal, antibiotic, antineoplastic or chemotherapeutic agent. In some aspects, administration of the antibacterial, antiviral, antifungal, antibiotic, antineoplastic or chemotherapeutic agent is concurrent with the lymphangiogenesis inducer and the antigen. In other aspects the antibacterial, antiviral, antifungal, antibiotic, antineoplastic or chemotherapeutic agent is administered separately. The antibacterial, antiviral, antifungal, antibiotic, antineoplastic or chemotherapeutic agent may be administered up to 1, 2, 3, 4, 5, 6, 7, 8, 9, 10, 11, 12, 13, 14, 15 16, 17, 18, 19, 20, 21, 22, 23 or 24 hours apart or up to 1, 2, 3, 4, 5, 6, 7, 8, 9, 10, 11, 12, 13, 14, 15 16, 17, 18, 19, 20, 21, 22, 23, 24, 25, 26, 27, 28, 29 30 or 31 days apart or up to 1, 2, 3, 4, 5, 6, 7, 8, 9, 10, 11 or 12 months apart (or any range derivable therein).

In particular aspects, the methods and compositions described are aimed at treating, preventing, ameliorating, suppressing, resolving, improving or otherwise addressing the symptoms of a subject or patient with an infection, disease or condition related to a bacterial infection, a viral infection, a fungal infection, a protozoal infection, a helminth infection or a cancer condition. In certain aspects, the subject exhibits one or more symptoms of a bacterial infection, a viral infection, a fungal infection, a protozoal infection, a helminth infection or a cancer condition. In other embodiments, the subject has been diagnosed with a bacterial infection, a viral infection, a fungal infection, a protozoal infection, a helminth infection or a cancer condition. In still other embodiments, the subject is at risk for a bacterial infection, a viral infection, a fungal infection, a protozoal infection, a helminth infection or a cancer condition. In specific embodiments the bacterial infection, viral infection, fungal infection, protozoal infection, helminth infection or cancer condition affects one or more organ systems. For example, a bacterial infection, a viral infection, a fungal infection, a protozoal infection, a helminth infection or a cancer condition may affect the circulatory system, integumentary system, skeletal system, reproductive system, digestive system, urinary system, respiratory system, endocrine system, lymphatic system, muscular system, nervous system or immune system. Specifically, a bacterial infection, a viral infection, a fungal infection, a protozoal infection, a helminth infection or a cancer condition may infect or affect the heart, blood, blood vessels, skin, hair, fat, nails, bones, cartilage, ligaments, tendons, sex organs, ovaries, fallopian tubes, uterus, vagina, mammary glands, testes, vas deferens, seminal vesicles, prostate, salivary glands, esophagus, stomach, liver, gallbladder, pancreas, intestines, rectum, anus, kidneys, ureters, bladder, urethra, pharynx, larynx, bronchi, lungs, diaphragm, hypothalamus, pituitary gland, pineal body, pineal gland, thyroid, parathyroid and adrenals, adrenal glands, lymph nodes, lymph vessels, skeletal muscles, smooth muscles, cardiac muscle, brain, spinal cord or peripheral nervous system.

In specific embodiments, the lymphangiogenesis inducer and the antigen are administered in a single composition. In certain aspects, the lymphangiogenesis inducer and the antigen are provided over multiple administrations. For example, the lymphangiogenesis inducer and the antigen may be provided over at least or at most 1, 2, 3, 4, 5, 6, 7, 8, 9, 10, 11, 12, 13, 14, 15, 16, 17, 18, 19, or 20 administrations (or any range derivable therein). In a further aspect, the subject is also administered an adjuvant. In still other aspects, the lymphangiogenesis inducer and the antigen are administered in a single composition comprising an adjuvant. In further aspects, the lymphangiogenesis inducer and the antigen are administered in a single composition comprising a pharmaceutically acceptable excipient. In specific embodiments, the composition is administered parenterally, subcutaneously or intramuscularly. In some embodiments, the adjuvant is operably linked to the tumor antigen. In some embodiments, the adjuvant is fused through a peptide bond to the tumor antigen. In some embodiments, the adjuvant is coupled to the tumor antigen chemically or encapsulated with the tumor antigen. In some embodiments, the adjuvant is injected into the site of the tumor and/or site of administration of the lymphanogenesis inducer and antigen. In some embodiments, the adjuvant is applied topically at the site of the tumor and or site of administration of the lymphanogensis inducer and antigen.

In certain aspects, administering to a patient or a subject an effective amount of a composition comprising a lymphangiogenesis inducer and the antigen comprises more than one administration of the composition. In certain aspects, the composition is administered orally, intravenously, subcutaneously, intradermally, intramuscularly, nasally, by injection, by inhalation, and/or using a nebulizer.

In still other embodiments, the subject is administered an effective amount of a second antigen. For example, the second antigen may be a bacterial antigen, a viral antigen, a fungal antigen, a protozoal antigen, a helminth antigen or a cancer antigen or a second bacterial antigen, a second viral antigen, a second fungal antigen, a second protozoal antigen, a second helminth antigen or a second cancer antigen. In some aspects the second antigen may be a biomolecule, a protein, a polypeptide, a carbohydrate, a polysaccharide, a lipid, a nucleic acid, a fatty acid, a glycolipid, a sterol, a polyterpene, a glycerolipid or a combination of these.

In further aspects, the lymphangiogenesis inducer is incorporated into a matrix. In certain aspects, the antigen is bound or incorporated into the matrix and is cleavable. In other aspects, the matrix incorporates one or more cleavable chemokines, chemoattractants, chemorepellants or one or more cleavable cytokines. For example, the chemokine may be one or any combination of chemokines selected from the group consisting of CCL1, CCL2, CCL3, CCL4, CCL5, CCL6, CCL7, CCL8, CCL9/CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, XCL1, XCL2 and CX3CL1. A cytokine for use with the methods or compositions disclosed herein may include members of the IL 17, IL-10, Interleukin, Lymphokine, Monokine, Myokine, Tumor necrosis factor or Proinflammatory cytokine families. Specific examples of cytokines for use with the methods and compositions described herein include one or any combination of Erythropoietin, GcMAF, Granulocyte colony-stimulating factor, Granulocyte macrophage colony-stimulating factor, Hepatocyte growth factor, IL1A, Interferon, Interferon beta-1a, Interferon beta-1b, Interferon gamma, Interferon type I, Interferon type II, Interferon type III, Interleukin 1 beta, Interleukin 1 receptor antagonist, Interleukin 10, Interleukin 12, Interleukin 13, Interleukin 16, Interleukin 2, Interleukin 23, Interleukin 23 subunit alpha, Interleukin 34, Interleukin 35, Interleukin 6, Interleukin 7, Interleukin 8, Interleukin-1 family, Interleukin-12 subunit beta, Interleukin-36, Leukemia inhibitory factor, Leukocyte-promoting factor, Lymphotoxin, Lymphotoxin alpha, Lymphotoxin beta, Macrophage colony-stimulating factor, Macrophage inflammatory protein, Macrophage-activating factor, Myonectin, Nicotinamide phosphoribosyltransferase, Oncostatin M, Oprelvekin, Platelet factor 4, Promegapoietin, RANKL, Stromal cell-derived factor 1, Tumor necrosis factor alpha or Vascular endothelial growth inhibitor.

In some embodiments the matrix is a gel. In yet other embodiments the matrix is a hydrogel. In certain instances, a hydrogel refers to three-dimensional hydrophilic cross-linked polymer networks that can absorb large volumes of water and biological fluids without dissolving. Hydrogels may be composed of polymers that are insoluble due to the presence of physical crosslinks (e.g., crystalline regions, intermolecular interactions and entanglements) or chemical crosslinks (e.g., covalent bonding). In specific embodiments, the hydrogel is a fibrin hydrogel or a fibrin domain modified polyethylene glycol hydrogel.

In one embodiment, the hydrogel is a fibrin hydrogel gel which is cross-linked with a cross-linking agent. In certain embodiments, the cross-linked fibrin hydrogel has chemical, physical or mechanical properties that are suitable for their use in implantation into a subject or patient, in particular subcutaneous implantation.

Without limitations, the gel can comprise any ratio of cross-linking agent to fibrin. Accordingly, the gel can comprise a cross-linking agent to fibrin ratio in the range from about 0.1:1 to about 10:1. In some embodiments of the aspects described herein, the gel comprises a cross-linking agent:fibrin ratio from 0.1:1 to 5:1, from 0.1:1 to 4:1, from 0.1:1 to 2:1, from 0.1:1 to 1.5:1, from 0.1:1 to 1:1, from 0.1:1 to 0.9:1, from 0.2 to 0.8:1, and/or from 0.25 to 0.75:1. In some embodiments, the gel comprises a cross-linking agent:fibrin ratio of 0.20:1 to 0.5:1. In some embodiments, the gel comprises a cross-linking agent:fibrin ratio of 0.25:1 or 0.5:1.

The hydrogels can be made from fibrin solutions comprising a wide concentration range of fibrin. Accordingly, the gel can be made from a fibrin solution comprising from about 50 mg/ml to about 500 mg/ml, from about 100 mg/ml to about 400 mg/ml, 150 mg/ml to about 300 mg/ml, 20 mg/ml to about 250 mg/ml of fibrin, or any range derivable therein. In some embodiments of the aspects described herein, the gel is made from a fibrin solution comprising about 200 mg/ml of fibrin. In some embodiments of the aspects described herein, the hydrogel is made from a fibrin solution comprising about 250 mg/ml of fibrin. In still some other embodiments of the aspects described herein, the hydrogel is made from a fibrin solution comprising about 300 mg/ml of fibrin.

In other embodiments, a hydrogel refers to a polymer that is formed by the free radical polymerization of a hydrophilic monomer solution gelled and crosslinked to form a three dimensional polymeric meshwork anchoring macromolecules. The macromolecules may comprise a constituent of a ground substance of tissue, such as a native collagen. Collagen may be interspersed within a polymeric meshwork forming a collagen-hydrogel. In some embodiments the collagen hydrogel is capable of promoting epithelial cell growth.

Soluble collagen for cross-linking can be prepared by art-recognized techniques. In addition, other proteins are that support cell attachment and growth may be used to form a cross-linked hydrogel. One example of an additional protein known to support cell growth is fibronectin.

Polysaccharides and mucopolysaccharides can also be added to hydrogels of the present invention.

Hydrogel polymers formed by free radical polymerization of monomer solutions require crosslinking to form the three dimensional polymeric structure of meshwork to gel the aqueous solution. The addition of crosslinking agents such as ethylene glycol dimethacrylate to the polymerization process can change the resultant hydrogel. Generally, the addition of crosslinking agents tend to increase the rigidity and mechanical strength of the hydrogel. Addition of cross-linking agents, such as ethylene glycol dimethacrylate and methymethacrylate, to the polymerization mixture in the presence of native collagen, still changes the physical properties of the hydrogel, and such additions to the polymerization mixture are compatible with the native collagen, and result in the collagen-hydrogel. Other known crosslinking agents that can be used satisfactorily in producing the collagen-hydrogel include diacrylates and dimethacrylates or other divalent molecules.

Without limitations, the gel can comprise any ratio of cross-linking agent to collagen. Accordingly, the gel can comprise a cross-linking agent to collagen ratio in the range from about 0.1:1 to about 10:1. In some embodiments of the aspects described herein, the gel comprises a cross-linking agent:collagen ratio from 0.1:1 to 5:1, from 0.1:1 to 4:1, from 0.1:1 to 2:1, from 0.1:1 to 1.5:1, from 0.1:1 to 1:1, from 0.1:1 to 0.9:1, from 0.2 to 0.8:1, and/or from 0.25 to 0.75:1. In some embodiments, the gel comprises a cross-linking agent:collagen ratio of 0.20:1 to 0.5:1. In some embodiments, the gel comprises a cross-linking agent:collagen ratio of 0.25:1 or 0.5:1.

The hydrogels can be made from collagen solutions comprising a wide concentration range of collagen. Accordingly, the gel can be made from a collagen solution comprising from about 50 mg/ml to about 500 mg/ml, from about 100 mg/ml to about 400 mg/ml, 150 mg/ml to about 300 mg/ml, 20 mg/ml to about 250 mg/ml of collagen, or any range derivable therein. In some embodiments of the aspects described herein, the gel is made from a collagen solution comprising about 200 mg/ml of collagen. In some embodiments of the aspects described herein, the hydrogel is made from a collagen solution comprising about 250 mg/ml of collagen. In still some other embodiments of the aspects described herein, the hydrogel is made from a collagen solution comprising about 300 mg/ml of collagen.

Hydrogels, which can be used as synthetic "stimuli-responsive" polymers may be based on synthetic polymers, such as poly (ethylene glycol) (PEG), poly(vinyl alcohol) (PVA), poly(N-isopropylacrylamide) (poly(NiPAAm)). Such hydrogels have been used in numerous regenerative medicine applications (see e.g. N. A. Peppas, P. Bures, W. Leobandung, and H. Ichikawa. Hydrogels in pharmaceutical formulations. Eur. J. Pharm. Biopharm. 50:27-46 (2000)), incorporated herein by reference.

In certain aspects hydrogels are prepared with various polymers such as polyvinyl alcohol (PVA). polyvinyl pyrrolidone (PVP), or polyacrylamides. Exemplary PVA-based hydrogels are disclosed in, e.g., U.S. Pat. Nos. 6,231,605; 5,346,935; 5,981,826; 4,663,358; and 4,988,761, the contents of which are herein incorporated by reference. In certain embodiments polyethylene glycol (PEG) based hydrogels provide a large degree of swelling in aqueous solutions. Various PEG based hydrogels are disclosed in U.S. Pat. Nos. 5,514,379; 6,362,276 and 6,541,015, the contents of which are herein incorporated by reference. PCT application WO2006125082, incorporated herein by reference, provides hydrogel formulation containing pre-solidified hydrogel particles in a precursor hydrogel solution.

Without limitations, the gel can comprise any ratio of cross-linking agent to poly (ethylene glycol) (PEG). Accordingly, the gel can comprise a cross-linking agent to PEG ratio in the range from about 0.1:1 to about 10:1. In some embodiments of the aspects described herein, the gel comprises a cross-linking agent:PEG ratio from 0.1:1 to 5:1, from 0.1:1 to 4:1, from 0.1:1 to 2:1, from 0.1:1 to 1.5:1, from 0.1:1 to 1:1, from 0.1:1 to 0.9:1, from 0.2 to 0.8:1, and/or from 0.25 to 0.75:1. In some embodiments, the gel comprises a cross-linking agent:PEG ratio of 0.20:1 to 0.5:1. In some embodiments, the gel comprises a cross-linking agent:PEG ratio of 0.25:1 or 0.5:1.

The hydrogels can be made from PEG solutions comprising a wide concentration range of PEG. Accordingly, the gel can be made from a PEG solution comprising from about 50 mg/ml to about 500 mg/ml, from about 100 mg/ml to about 400 mg/ml, 150 mg/ml to about 300 mg/ml, 20 mg/ml to about 250 mg/ml of PEG, or any range derivable therein. In some embodiments of the aspects described herein, the gel is made from a PEG solution comprising about 200 mg/ml of PEG. In some embodiments of the aspects described herein, the hydrogel is made from a PEG solution comprising about 250 mg/ml of PEG. In still some other embodiments of the aspects described herein, the hydrogel is made from a PEG solution comprising about 300 mg/ml of PEG.

In certain aspects the lymphangiogenesis inducer is capable of binding to the matrix or hydrogel. Hydrogels can further be prepared according to any of U.S. Pat. Nos. 4,684,558, 5,346,935, 6,534,083, 6,576,679 or U.S. Pat. No. 8,329,763, all of which are herein incorporated by reference. In specific embodiments, the lymphangiogenesis inducer comprises a matrix binding domain. In certain aspects the lymphangiogenesis inducer is a modified vascular endothelial growth factor C (VEGF-C) or VEGF-D protein comprising a fibrin-binding domain.

In some aspects the lymphangiogenesis inducer the antigen or both the lymphangiogenesis inducer and the antigen are formulated in or as part of a liposome, micelle or nanoparticle.

In further aspects, the lymphangiogenesis inducer comprises a protease cleavage site. Examples of proteases classes that may act upon or cleave the protease cleavage site include serine proteases, cysteine proteases, threonine proteases, aspartic proteases, glutamic proteases, metalloproteases or asparagine peptide lyases. In specific embodiments, the protease cleavage site is a matrix metalloprotease cleavage site.

In yet further aspects, the VEGF-C is recombinant, the antigen is recombinant or both the VEGF-C and the antigen are recombinant. In certain aspects, the antigen is encoded by a recombinant nucleic acid molecule. In certain aspects the VEGF-C or VEGF-D, the antigen or both the VEGF-C or VEGF-D and the antigen are expressed by a heterologous cell line.

In some embodiments, the matrix or hydrogel is implanted into a subject. In specific embodiments, the lymphangiogenesis inducer and antigen can be administered separately. In still other aspects the lymphangiogenesis inducer and the antigen are administered up to 1 month apart. In other embodiments, the lymphangiogenesis inducer and the antigen are administered up to 1, 2, 3, 4, 5, 6, 7, 8, 9, 10, 11, 12, 13, 14, 15 16, 17, 18, 19, 20, 21, 22, 23 or 24 hours apart or up 1, 2, 3, 4, 5, 6, 7, 8, 9, 10, 11, 12, 13, 14, 15 16, 17, 18, 19, 20, 21, 22, 23, 24, 25, 26, 27, 28, 29 30 or 31 days apart or up to 1, 2, 3, 4, 5, 6, 7, 8, 9, 10, 11 or 12 months apart. In specific embodiments, the subject is a mammal. In further aspects, the subject is a human.

In certain aspects the immune response induced by the methods disclosed herein is a protective immune response. In yet further aspects, the immune response produces antibodies that specifically bind to the antigen or the second antigen. In certain aspects the immune response produces antibodies that specifically bind to antigens present in a cell lysate. In specific aspects the cell lysate is a tumor cell lysate.

Embodiments are also directed to a method of treating or preventing an infection in a subject, the method comprising administering to the subject an isolated lymphangiogenesis inducer and an effective amount of an antigen. In some embodiments, the lymphangiogenesis inducer is vascular endothelial growth factor C (VEGF-C) or vascular endothelial growth factor D (VEGF-D). In certain embodiments, the antigen is bacterial antigen, a viral antigen, a fungal antigen, a helminth antigen or a protozoal antigen. In yet further embodiments, the method of treating or preventing an infection in a subject comprises administration of an effective amount of a second antigen to the subject.

In certain aspects, the method of treating or preventing an infection in a subject comprises a lymphangiogenesis inducer and an antigen administered in a single composition. In some embodiments, the lymphangiogenesis inducer and the antigen are provided over multiple administrations. In yet further embodiments, the subject is also administered an adjuvant. In certain embodiments, the lymphangiogenesis inducer and the antigen are administered in a single composition comprising an adjuvant. In some embodiments the lymphangiogenesis inducer and the antigen are administered in a single composition comprising a pharmaceutically acceptable excipient. In certain aspects, the composition is administered parenterally, subcutaneously or intramuscularly.

In other aspects, the method of treating or preventing an infection in a subject comprises a lymphangiogenesis inducer incorporated into a matrix. Embodiments of the method of treating or preventing an infection in a subject also include an antigen that is bound or incorporated into the matrix and is cleavable. In some embodiments, the matrix incorporates one or more cleavable chemokines, chemoattractants, chemorepellants or one or more cleavable cytokines. In certain embodiments, the matrix is a hydrogel. In certain aspects, the hydrogel is a fibrin hydrogel or a fibrin domain modified polyethylene glycol hydrogel. In still further aspects, the lymphangiogenesis inducer is capable of binding to the matrix or hydrogel. In yet further embodiments, the lymphangiogenesis inducer comprises a matrix binding domain. In certain embodiments, the lymphangiogenesis inducer is a modified vascular endothelial growth factor C (VEGF-C) or vascular endothelial growth factor D (VEGF-D) protein comprising a fibrin-binding domain. In some embodiments, the matrix or hydrogel is implanted into the subject.

In some embodiments, the method of treating or preventing an infection in a subject comprises a lymphangiogenesis inducer that comprises a protease cleavage site. In other aspects, the protease cleavage site is a matrix metalloprotease cleavage site.

In yet further embodiments, the VEGF-C or VEGF-D is recombinant, the antigen is recombinant or both the VEGF-C or VEGF-D and the antigen are recombinant. In certain embodiments, the VEGF-C or VEGF-D, the antigen or both the VEGF-C or VEGF-D and the antigen are expressed by a heterologous cell line. In some embodiments, the antigen is encoded by a recombinant nucleic acid molecule.

In certain aspects, the lymphangiogenesis inducer and antigen are administered separately. In other aspects, the lymphangiogenesis inducer and the antigen are administered up to 1 month apart. In certain embodiments, the subject is a mammal. Embodiments are also included wherein the subject is a human.

In yet further embodiments, administration of the lymphangiogenesis inducer and antigen or second antigen produces antibodies that specifically bind to the antigen or the second antigen.

Other embodiments of the present invention include a pharmaceutical composition comprising a lymphangiogenesis inducer, an effective amount of an antigen and a pharmaceutically acceptable excipient. In certain embodiments, the pharmaceutical composition comprises vascular endothelial growth factor C (VEGF-C) or vascular endothelial growth factor D (VEGF-D). In some aspects, the pharmaceutical composition comprises a bacterial antigen, a viral antigen, a fungal antigen, a protozoal antigen or a cancer antigen. In still other aspects, the pharmaceutical composition comprises an adjuvant. In certain embodiments, the composition is adapted to be administered parenterally, subcutaneously or intramuscularly. In some aspects, the pharmaceutical composition comprises an effective amount of a second antigen.

In certain embodiments, the pharmaceutical composition comprises a lymphangiogenesis inducer that is incorporated into a matrix. In still other aspects, the pharmaceutical composition comprises an antigen which is bound or incorporated into the matrix and is cleavable. In yet further aspects, the pharmaceutical composition comprises a matrix that incorporates one or more cleavable chemokines, chemoattractants, chemorepellants or one or more cleavable cytokines. In still other aspects, the matrix of the pharmaceutical composition is a hydrogel. In certain embodiments, the hydrogel is a fibrin hydrogel or a fibrin domain modified polyethylene glycol hydrogel. In still other embodiments, the lymphangiogenesis inducer is bound or incorporated into the matrix or hydrogel. In some aspects, the lymphangiogenesis inducer comprises a matrix binding domain. In certain embodiments, the lymphangiogenesis inducer comprises a protease cleavage site. In still other aspects, the lymphangiogenesis inducer is a modified vascular endothelial growth factor C (VEGF-C) protein comprising a fibrin-binding domain and a matrix metalloprotease cleavage site. In some aspects, the VEGF-C is recombinant, the antigen is recombinant or both the VEGF-C and the antigen are recombinant. In certain embodiments, the VEGF-C, the antigen or both the VEGF-C and the antigen are expressed by a heterologous cell line. Embodiments also include a vaccine that comprising any composition as described herein.

In some aspects, a method for treating or preventing a bacterial infection, a viral infection, a fungal infection, a protozoal infection, a helminth infection or a cancer condition in a subject or patient comprising administering to the subject or patient a pharmaceutically acceptable vaccine composition comprising at least a first lymphangiogenesis inducer and one or more antigens. In other embodiments, the subject is administered the vaccine composition multiple times. In still other embodiments, the composition is administered orally, intravenously, subcutaneously, intradermally, intramuscularly, nasally, by injection, by inhalation, and/or using a nebulizer. In certain aspects, the subject exhibits one or more symptoms of a bacterial infection, a viral infection, a fungal infection, a protozoal infection, a helminth infection or a cancer condition.

Furthermore, in certain embodiments of the current compositions or methods, the compositions may contain about, at least about, or at most about 0.1, 0.2, 0.3, 0.4, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 21, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 μg or mg of a biomolecule, a protein, a polypeptide, a carbohydrate, a polysaccharide, a lipid, a nucleic acid, a fatty acid, a glycolipid, a sterol, a polyterpene, a glycerolipid or a combination of these (or any range derivable therein). The biomolecule, a protein, a polypeptide, a carbohydrate, a polysaccharide, a lipid, a nucleic acid, a fatty acid, a glycolipid, a sterol, a polyterpene, a glycerolipid or a combination of these may be in about, at least about, or at most about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 10, 11, 12, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 μl or ml (or any range derivable therein). In certain aspects, one or more lymphangiogenesis inducers or one or more antigens can be administered as a dose of 0.1, 0.2, 0.3, 0.4, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 21, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 mg per kg of body weight.

Certain aspects are directed to a method of treating neoplasia, dysplasia or cancer, the method comprising administering to a subject an isolated lymphangiogenesis inducer and an effective amount of one or more neoplasia, dysplasia or cancer antigens. The one or more neoplasia, dysplasia or cancer antigens may be one or more antigens from leukemias, lymphomas, neurological tumors such as astrocytomas or glioblastomas, melanoma, breast cancer, lung cancer, head and neck cancer, gastrointestinal tumors, gastric cancer, colon cancer, liver cancer, pancreatic cancer, genitourinary tumors such as cervical or uterine tumors, ovarian cancer, vaginal cancer, testicular cancer, prostate cancer or penile cancer, bone tumors, vascular tumors, cancer of the lip, nasopharynx, pharynx, oral cavity, esophagus, rectum, gall bladder, biliary tree, larynx, lung or bronchus, bladder cancer, kidney cancer, brain cancer or cancer from other parts of the nervous system, thyroid cancer, Hodgkin's disease, non-Hodgkin's lymphoma or multiple myeloma.

In some embodiments, the method of treating neoplasia, dysplasia or cancer comprises a method where the lymphangiogenesis inducer is vascular endothelial growth factor C (VEGF-C) or vascular endothelial growth factor D (VEGF-D). In certain embodiments, the one or more antigens are cancer antigens. In yet other embodiments, the one or more antigens are in or are part of a cell lysate. The cell lysate may be a cancer, dysplasia, neoplasia or tumor lysate. After lysis or disruption of cells to generate the cell lysate, the lysate may be purified or enriched. Enrichment may be for a specific biomolecule, a protein, a polypeptide, a carbohydrate, a polysaccharide, a lipid, a nucleic acid, a fatty acid, a glycolipid, a sterol, a polyterpene, a glycerolipid or a combination of these.

In further aspects, the method of treating neoplasia, dysplasia or cancer comprises a method where the lymphangiogenesis inducer and the one or more neoplasia, dysplasia or cancer antigens are administered in a single composition. In some embodiments, the lymphangiogenesis inducer and the one or more neoplasia, dysplasia or cancer antigens are provided over multiple administrations. In still other embodiments, the subject is also administered an adjuvant. In certain embodiments, the lymphangiogenesis inducer and the one or more neoplasia, dysplasia or cancer antigens are administered in a single composition comprising an adjuvant. In yet other embodiments, the lymphangiogenesis inducer and the one or more neoplasia, dysplasia or cancer antigens are administered in a single composition comprising a pharmaceutically acceptable excipient. In some embodiments, the composition is administered parenterally, subcutaneously or intramuscularly.

In certain embodiments, the subject is administered an effective amount of a second neoplasia, dysplasia or cancer antigen.

In further aspects, the lymphangiogenesis inducer is incorporated into a matrix. In still other embodiments, the antigen is bound or incorporated into the matrix and is cleavable. In yet other embodiments, the matrix incorporates one or more cleavable chemoattractants or one or more cleavable cytokines.

In some embodiments, the matrix is a hydrogel. In still other embodiments, the hydrogel is a fibrin hydrogel or a fibrin domain modified polyethylene glycol hydrogel. In certain embodiments, the lymphangiogenesis inducer is capable of binding to the matrix or hydrogel. Embodiments are also included wherein the lymphangiogenesis inducer comprises a matrix binding domain. In some embodiments, the lymphangiogenesis inducer comprises a protease cleavage site. In further aspects, the lymphangiogenesis inducer is a modified vascular endothelial growth factor C (VEGF-C) protein comprising a fibrin-binding domain. In certain embodiments, the lymphangiogenesis inducer is a modified vascular endothelial growth factor C (VEGF-C) protein comprising a matrix metalloprotease cleavage site. Specific embodiments are also included wherein the matrix or hydrogel is implanted into the subject.

In yet other embodiments, the VEGF-C is recombinant, the one or more neoplasia, dysplasia or cancer antigens are recombinant or both the VEGF-C and the one or more antigens are recombinant. In still other embodiments, the VEGF-C, the antigen or both the VEGF-C and the one or more neoplasia, dysplasia or cancer antigens are expressed by a heterologous cell line.

In yet other embodiments, the lymphangiogenesis inducer and one or more neoplasia, dysplasia or cancer antigens are administered separately. In some embodiments, the lymphangiogenesis inducer and one or more neoplasia, dysplasia or cancer antigens are administered up to 1 month apart. In other embodiments, the lymphangiogenesis inducer and the antigen are administered up to 1, 2, 3, 4, 5, 6, 7, 8, 9, 10, 11, 12, 13, 14, 15 16, 17, 18, 19, 20, 21, 22, 23 or 24 hours apart or up 1, 2, 3, 4, 5, 6, 7, 8, 9, 10, 11, 12, 13, 14, 15 16, 17, 18, 19, 20, 21, 22, 23, 24, 25, 26, 27, 28, 29 30 or 31 days apart or up to 1, 2, 3, 4, 5, 6, 7, 8, 9, 10, 11 or 12 months apart. In further aspects, the subject is a mammal. In certain embodiments, the subject is a human. In still other embodiments, administration of the lymphangiogenesis inducer and the one or more neoplasia, dysplasia or cancer antigens or the second neoplasia, dysplasia or cancer antigen produces antibodies that specifically bind to the one or more neoplasia, dysplasia or cancer antigens or to the second neoplasia, dysplasia or cancer antigen.

In certain embodiments, the one or more neoplasia, dysplasia or cancer antigens are encoded by a recombinant nucleic acid molecule.

In some embodiments, the cancer comprises breast cancer or melanoma. In some embodiments, the cancer comprises a cancer disclosed herein. In some embodiments, the neoplasia or dysplasia is in the breast or skin. In some embodiments, the neoplasia or dysplasia are pre-cancerous cells that are a precursor to a cancer described herein. In some embodiments, the cancer, dysplasia, and/or neoplasia comprises a solid tumor. In some embodiments, the cancer is non-lymphatic.

In some embodiments, the method further comprises administration of an immunotherapy. In some embodiments, the immunotherapy comprises a checkpoint blockade inhibitor, adoptive T cell therapy, a chimeric antigen receptor, a STING agonist, cytolytic virus therapy, one or more additional antigens, tumor cell lysate, tolerance-breaking peptide antigen, a dendritic cell vaccine (e.g. Provenge), and/or an antibody-antigen conjugate. It is contemplated that combinations of immunotherapy may be administered or that one or more immunotherapies may be excluded.

Certain embodiments are directed to a method of inducing immune tolerance, the method comprising administering to a subject an isolated lymphangiogenesis inducer and an effective amount of an antigen. In further embodiments, the method of inducing immune tolerance comprises administering one or more tolerogenic adjuvants.

In particular embodiments, the immune tolerance response elicited by the lymphangiogenesis inducer and an effective amount of an antigen may be complemented, supplemented, increased or augmented. In some embodiments the antigen may be myelin sheath protein is myelin basic protein (MBP), myelin oligodendrocyte glycoprotein (MOG), proteolipid protein (PLP), or myelin associated glycoprotein (MAG). In certain aspects the immune tolerance response elicited by the lymphangiogenesis inducer and an effective amount of an antigen may be complemented, supplemented, increased or augmented by an adjuvant. In certain aspects the adjuvant is a tolerogenic adjuvant. In certain embodiments the lymphangiogenesis inducer and an effective amount of an antigen composition further comprises at least one tolerogenic adjuvant. In certain aspects the tolerogenic adjuvant is attached or bound to a hydrogel, a lymphangiogenesis inducer or an antigen. In other aspects, the tolerogenic adjuvant is conjugated to a hydrogel, a lymphangiogenesis inducer or an antigen. In still other aspects, the tolerogenic adjuvant is fused to a hydrogel, a lymphangiogenesis inducer or an antigen. In specific embodiments, the tolerogenic adjuvant is selected from IL-10, dexamethasone, FK506 (Tacrolimus), cholera toxin B subunit, *Escherichia coli* heat-labile enterotoxin B subunit, IFN-beta, glucocorticoids, vitamin D3, and vitamin D3 analogues.

In some aspects, a method for treating an autoimmune disease or a demyelinating disease in a subject comprising administering to the subject a pharmaceutically acceptable composition comprising at least a first an isolated lymphangiogenesis inducer and an effective amount of at least one antigen is contemplated. In some embodiments the antigen may be myelin sheath protein is myelin basic protein (MBP), myelin oligodendrocyte glycoprotein (MOG), proteolipid protein (PLP), or myelin associated glycoprotein (MAG). In some embodiments, the isolated lymphangiogenesis inducer is VEGF-C or VEGF-D. In other embodiments, the subject is administered the composition multiple times. In still other embodiments, the composition is administered orally, intravenously, subcutaneously, intradermally, intramuscularly, nasally, by injection, by inhalation, and/or using a nebulizer. In certain aspects, the subject exhibits one or more symptoms of a demyelinating disease. In additional aspects, the subject has been diagnosed with a demyelinating disease. In some embodiments, the subject is at risk for a demyelinating disease. In other embodiments, the demyelinating disease affects the central nervous system. In additional embodiments, the demyelinating disease is an idiopathic inflammatory demyelinating disease. In certain aspects, the demyelinating disease is multiple sclerosis, neuropathy, central pontine myelinolysis, tabes *dorsalis*, transverse myelitis, Devic's disease, progressive multifocal leukoencephalopathy, optic neuritis, or leukodystrophy. In specific embodiments, the demyelinating disease is multiple sclerosis. In some embodiments, the demyelinating disease is one of the borderline forms of multiple sclerosis. In some aspects, the borderline form of multiple sclerosis is standard multiple sclerosis, Remitent-Recidivant multiple sclerosis (RRMS), Secondary Progressive multiple sclerosis (SPMS), Primary progressive multiple sclerosis (PPMS), KIR4.1 multiple sclerosis, Optic-spinal multiple sclerosis, Opticospinal multiple sclerosis, Devic's disease, acute disseminated encephalomyelitis (ADEM), acute hemorrhagic leukoencephalitis, Balo concentric sclerosis, Schilder disease, diffuse myelinoclastic sclerosis, Marburg multiple sclerosis, malignant multiple sclerosis, fulminant multiple sclerosis, acute multiple sclerosis, Tumefactive multiple sclerosis, or Solitary sclerosis. In yet other embodiments the demyelinating disease is Susac's syndrome, myalgic encephalomyelitis or leukoaraiosis. In other aspects, the demyelinating disease affects the peripheral nervous system. In specific embodiments, the demyelinating disease is Guillain-Barré syndrome, chronic inflammatory demyelinating polyneuropathy, anti-MAG peripheral neuropathy, Charcot-Marie-Tooth Disease or progressive inflammatory neuropathy. In certain embodiments, the methods further comprise preparing the composition. In further embodiments still, the methods further comprise measuring antibodies against the at least one myelin sheath protein in the subject after administering the composition. In some aspects a patient or subject has been diagnosed with or is at risk for an autoimmune disease or disorder. In some embodiments a patient or subject has been diagnosed with asthma or an allergic disorder. In yet other aspects, a method for treating asthma or an allergic reaction in a subject comprising administering to the subject a pharmaceutically acceptable composition comprising at least a first an isolated lymphangiogenesis inducer and an effective amount of at least one antigen is contemplated.

In some embodiments, there are methods and compositions for treating a cancer patient with cancer immunotherapy, for administering cancer immunotherapy, for predicting efficacy of cancer immunotherapy in a cancer patient, for prognosing a cancer patient, for evaluating treatment for a cancer patient, for evaluating cancer immunotherapy for a cancer patient; for evaluating efficacy of immunotherapy in a cancer patient, and/or for determining a cancer treatment for a cancer patient.

In certain embodiments, there are methods for treating a cancer patient with cancer immunotherapy comprising administering cancer immunotherapy to the patient after detecting in a serum sample from that patient a level of VEGF-C and/or CCL21 that is indicative of response to cancer immunotherapy. The expression level or activity level from a control sample or test biological sample from the patient may be an average value, a median value, a normalized value, a cut-off value, or an average normalized value. The expression level or activity level may be an average or mean obtained from a significant proportion of patient samples. The expression or activity level may also be an average or mean from one or more samples from the patient.

Further steps of methods may include measuring or detecting the level of expression in a sample from the patient; comparing a measured or detected level of expression to the level or range of levels in a control sample; and/or determining the patient is a good candidate for a particular immunotherapy or predicting that a particular immunotherapy will have therapeutic efficacy or predicting that a particular immunotherapy is unlikely to be efficacious on the patient. A patient is predicted to respond favorably or positively to a particular immunotherapy if the expression level of VEGF-C and/or CCL21 in a sample from the patient is indicative of the level observed in patient who respond favorably or positively to that particular immunotherapy.

In certain embodiments, there are methods for treating a cancer patient with cancer immunotherapy comprising administering cancer immunotherapy to the patient after detecting in a serum sample from that patient a level of VEGF-C and/or CCL21 that is indicative of response to cancer immunotherapy. In additional embodiments, there are methods for predicting the efficacy of cancer immunotherapy in a patient comprising: measuring a level of VEGF-C and/or CCL21 protein expression in a serum sample from the patient; and, comparing the level of VEGF-C and/or CCL21 protein expression to a level in a control sample. In certain embodiments, the level is increased when compared to the level in a control sample.

In some embodiments, methods involve further comprising comparing the level of VEGF-C and/or CCL21 to a control level. In other embodiments, the control level is a level of VEGF-C or CCL21 expression from serum of patients who affirmatively respond to the cancer immunotherapy. In additional embodiments, such patients are those who affirmatively respond to the cancer immunotherapy exhibit at least a 25% reduction in tumor growth following treatment with the cancer immunotherapy. In further embodiments, the control level is a level of VEGF-C or CCL21 expression that is the median level in serum of cancer patients. In other cases, the patient is administered immunotherapy after being determined to have a level of expression of VEGF-C or CCL21 that is increased as compared to the level of expression in serum from noncancer patients. In other cases, the control level is a level or range of level of VEGF-C or CCL21 expression from serum of patients who do not respond affirmatively to the cancer immunotherapy. In further embodiments, methods involve a control level that is a level or range of level of VEGF-C or CCL21 expression in serum from patients who do not respond affirmatively to the cancer immunotherapy.

In some methods, there is the additional step of obtaining serum from the patient. While in other cases, the sample has already been obtained or a level of expression has already been measured, though in some embodiments, methods involve measuring the level of VEGF-C and/or CCL21 expression in serum from the patient. In some embodiments, there are methods involving measuring the level of VEGF-C and/or CCL21 expression comprises using a peptide or polypeptide that binds VEGF-C and/or CCL21. In further embodiments, an immunotherapy is a checkpoint blockade inhibitor, adoptive T cell therapy, a chimeric antigen receptor, a STING agonist, cytolytic virus therapy, one or more additional antigens, tumor cell lysate, tolerance-breaking peptide antigen, a dendritic cell vaccine, or an antibody-antigen conjugate.

In some embodiments, the biological sample from the patient is a sample from a primary tumor. In some embodiments, the biological sample is from a tissue or organ as described herein. In still further embodiments, the method may comprise obtaining a sample of the subject or patient. Non-limiting examples of the sample include a tissue sample, a whole blood sample, a urine sample, a saliva sample, a serum sample, a plasma sample, or a fecal sample. In particular embodiments, the sample is a serum sample.

In some embodiments the subject or patient is one that has previously been treated for cancer. In some embodiments, the cancer is recurrent.

The term subject or patient may refer to an animal (for example a mammal), including but not limited to humans, non-human primates, rodents, dogs, or pigs. The methods of obtaining provided herein include methods of biopsy such as fine needle aspiration, core needle biopsy, vacuum assisted biopsy, incisional biopsy, excisional biopsy, punch biopsy, shave biopsy or skin biopsy.

In certain embodiments the sample is obtained from a biopsy from gall bladder, skin, heart, lung, breast, pancreas, liver, muscle, kidney, smooth muscle, bladder, intestine, brain, prostate, esophagus, or thyroid tissue.

Alternatively, the sample may include but not be limited to blood, serum, sweat, hair follicle, buccal tissue, tears, menses, urine, feces, or saliva. In particular embodiments, the sample may be a tissue sample, a whole blood sample, a urine sample, a saliva sample, a serum sample, a plasma sample or a fecal sample.

In certain aspects the sample is obtained from cystic fluid or fluid derived from a tumor or neoplasm. In certain aspects of the current methods, any medical professional such as a doctor, nurse or medical technician may obtain a biological sample for testing. In further aspects of the current methods, the patient or subject may obtain a biological sample for testing without the assistance of a medical professional, such as obtaining a whole blood sample, a urine sample, a fecal sample, a buccal sample, or a saliva sample.

In further embodiments, the sample may be a fresh, frozen or preserved sample or a fine needle aspirate. In particular embodiments, the sample is a formalin-fixed, paraffin-embedded (FFPE) sample. An acquired sample may be placed in short term or long term storage by placing in a suitable medium, excipient, solution, or container. In certain cases storage may require keeping the sample in a refrigerated, or frozen environment. The sample may be quickly frozen prior to storage in a frozen environment. In certain instances the frozen sample may be contacted with a suitable cryopreservation medium or compound. Examples of cryopreservation mediums or compounds include but are not limited to: glycerol, ethylene glycol, sucrose, or glucose.

Some embodiments further involve isolating nucleic acids such as ribonucleic or RNA from a biological sample or in a sample of the patient. Other steps may or may not include amplifying a nucleic acid in a sample and/or hybridizing one or more probes to an amplified or non-amplified nucleic acid. The methods may further comprise assaying nucleic acids in a sample. Further embodiments include isolating or analyzing protein expression in a biological sample for the expression of the biomarker.

In certain embodiments, a microarray or ELISA may be used to measure or assay the level of CCL21 or VEGF-C in a sample. The methods may further comprise recording the expression or activity level in a tangible medium or reporting the expression or activity level to the patient, a health care payer, a physician, an insurance agent, or an electronic system.

In some embodiments, methods will involve determining or calculating a prognosis score based on data concerning the expression or activity level of one or more of VEGF-C and CCL21, meaning that the expression or activity level of one or more of VEGF-C and CCL21 is at least one of the factors on which the score is based. A prognosis score will provide information about the patient, such as the general probability whether the patient is sensitive to a particular therapy or has poor survival or high chances of recurrence. In certain embodiments, a prognosis value is expressed as a numerical integer or number that represents a probability of 0% likelihood to 100% likelihood that a patient has a chance of poor survival or cancer recurrence or poor response to a particular treatment.

In some embodiments, the subject or patient is determined to be a candidate for or is further administered an immunotherapy when the VEGF-C or CCL21 level in the serum sample is greater than 2, 3, 4, 5, 6, 7, 8, 9, 10, 12, 14, 16, 18, 20, 25, 30, 35, or 40 ng/ml (or any derivable range therein).

In some embodiments, the subject or patient is determined to be a candidate for or is further administered an immunotherapy when the VEGF-C or CCL21 level is at least ⅓, ⅔, 1, 1.5, 2, 2.5, 3, 3.5, 4, 4.5, or 5 standard deviations from a control.

In some embodiments, the subject or patient is determined to be a candidate for or is further administered an immunotherapy when the VEGF-C or CCL21 level is at least 2, 3, 4, 5, 6, 7, 8, 9, 10, 12, 14, 16, 18, 20, or 30 fold (or any derivable range therein) higher in a biological sample from the patient compared to the level in a control.

In some embodiments, the method further comprises surgical incision of the primary tumor. In some embodiments, the elevated level/increased expression or reduced level/decreased expression is at least 1, 1.5, 2, 2.5, 3, 3.5, 4, 4.5, 5, 5.5, 6, 7, 8, 9, 10, 12, 14, 16, 18, 20, 50, 100, 150, 200, 250, 500, or 1000 fold (or any derivable range therein) or at least 10, 20, 30, 40, 50, 60, 70, 80, 90, 100, 200, 300, 400, 500, 600, 700, 800, or 900% different than the control, or any derivable range therein.

In some embodiments, the prognosis score is expressed as a number that represents a probability of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% likelihood (or any range derivable therein) that a patient will have a poor response to a particular treatment. Alternatively, the probability may be expressed generally in percentiles, quartiles, or deciles.

A control may be serum from healthy or noncancerous patients; a control level may be the level or range of levels that represent the level of expression from healthy or non-cancerous patients. In some embodiments, a control may be serum from cancer patients known to respond positively to the relevant immunotherapy, such as by demonstrating at least a 25% decrease in tumor volume after being given a particular immunotherapy. In other embodiments, a control may be serum from cancer patients known to be unresponsive to the relevant immunotherapy or to be poor responders to the relevant immunotherapy, such as by notdemonstrating at least a 25% decrease in tumor volume after being given that immunotherapy.

A difference between or among weighted coefficients or expression or activity levels or between or among the weighted comparisons may be, be at least or be at most about 0.1, 0.2, 0.3, 0.4, 0.5, 0.6, 0.7, 0.8, 0.9, 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 times or -fold (or any range derivable therein).

In some embodiments, determination of calculation of a diagnostic, prognostic, or risk score is performed by applying classification algorithms based on the expression values of VEGF-C or CCL21 with differential expression p values of about, between about, or at most about 0.005, 0.006, 0.007, 0.008, 0.009, 0.01, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.03, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050, 0.051, 0.052, 0.053, 0.054, 0.055, 0.056, 0.057, 0.058, 0.059, 0.060, 0.061, 0.062, 0.063, 0.064, 0.065, 0.066, 0.067, 0.068, 0.069, 0.070, 0.071, 0.072, 0.073, 0.074, 0.075, 0.076, 0.077, 0.078, 0.079, 0.080, 0.081, 0.082, 0.083, 0.084, 0.085, 0.086, 0.087, 0.088, 0.089, 0.090, 0.091, 0.092, 0.093, 0.094, 0.095, 0.096, 0.097, 0.098, 0.099, 0.1, 0.2, 0.3, 0.4, 0.5, 0.6, 0.7, 0.8, 0.9 or higher (or any range derivable therein).

Further aspects relate to a kit comprising nucleic acid probes and/or polypeptides (e.g. antibodies) for detecting the expression level of VEGF-C or CCL21 in a biological sample. In some embodiments, the probes or polypeptides are labeled. In some embodiments, the kit further comprises nucleic acid probes or polypeptides for detecting a control. In some embodiments, the probe comprises nucleic acid primers that are capable of amplifying VEGF-C or CCL21 genes by PCR. In some embodiments, the kit further comprises reagents for performing one or more of reverse transcriptase PCR, ELISA, DNA amplification by PCR, and real-time PCR. In some embodiments, the kit further comprises instructions for use.

Any of the methods described herein may be implemented on tangible computer-readable medium comprising computer-readable code that, when executed by a computer, causes the computer to perform one or more operations. In some embodiments, there is a tangible computer-readable medium comprising computer-readable code that, when executed by a computer, causes the computer to perform operations comprising: a) receiving information corresponding to an expression or activity level of a gene, biomarker or protein in a sample from a patient; and b) determining a difference value in the expression or activity levels using the information corresponding to the expression or activity levels in the sample compared to a control or reference expression or activity level for the gene.

In other aspects, tangible computer-readable medium further comprise computer-readable code that, when executed by a computer, causes the computer to perform one or more additional operations comprising making recommendations comprising: wherein the patient in the step a) is under or after a first treatment for cancer, administering the same treatment as the first treatment to the patient if the patient does not have increased expression or activity level; administering a different treatment from the first treatment to the patient if the patient has increased expression or activity level.

In some embodiments, receiving information comprises receiving from a tangible data storage device information corresponding to the expression or activity levels from a tangible storage device. In additional embodiments the medium further comprises computer-readable code that, when executed by a computer, causes the computer to perform one or more additional operations comprising: sending information corresponding to the difference value to a tangible data storage device, calculating a prognosis score for the patient, treating the patient with a traditional cancer therapy if the patient does not have expression or activity levels, and/or or treating the patient with an alternative cancer therapy if the patient has increased expression or activity levels.

The tangible, computer-readable medium further comprise computer-readable code that, when executed by a computer, causes the computer to perform one or more additional operations comprising calculating a prognosis score for the patient. The operations may further comprise making recommendations comprising: administering a treatment comprising a thymidylate synthase inhibitor to a patient that is determined to have a decreased expression or activity level.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-C—LECs express MHC-II under resting conditions, and upregulate it under inflammatory conditions, promoting $CD4^+$ T cell education. (A) Primary LN-LECs were stimulated with IFNγ or TNFα for 6 h, or left in culture medium, prior to measurement of MHC-II levels by flow cytometry. Representative histograms of MHC-II expression are shown. (B) BMDCs or primary LN-LECs or LN-FRCs were stimulated with IFNγ over up to 20 h, and surface expression was detected via flow cytometry. Mean fluorescence intensities (MFIs) were normalized to negative controls (dotted line). (C) OVA-reactive $CD4^+$ T (OT-II) cells that recognize the $OVA_{323-339}$ peptide were co-cultured in the presence of the peptide with mDCs or LN-LECs, and proliferation (CFSE dilution) and the expression of memory and effector phenotypic markers were assessed after 4 d. Numbers indicate representative percentage of OT-II cells that express CD44 or CD62L under each education condition.

FIG. 2A-F—DCs and LECs activate cognate T cells and promote different T cell phenotypes. DCs, LN-LECs, or LN-FRCs from healthy wild-type mice, or immortalized LECs (iLECs) were co-cultured with OT-I cells in the presence of 10 nM SIINFEKL for 3 d. (A) Representative histograms depicting CFSE dilution of OT-I cells and (B) quantification of OT-I cell proliferation in the form of proliferation index, versus the APC used to 'educate' the OT-I cells. (C-F) Quantification of typical T cell activation and functional markers by flow cytometry. (C) Representative dot plots of CFSE versus several functional markers to reflect upregulation or downregulation of certain markers as the T cells proliferated. (D-F) Percentage of all OT-I cells, regardless of number of cell divisions undertaken, that express (D) the memory-like phenotype characterized by $CD44^+CD62L^+$ staining, (E) ability to migrate to LNs via the CCR7 receptor, and (F) tissue-resident phenotype by $CD103^+$ staining.

FIG. 3A-C—LEC-educated OT-I cells can be activated following CD28 stimulation, and can produce effector cytokines as well as DC-educated OT-I cells. (A) Flow cytometry was used to analyze the expression of various functional markers on OT-I cells co-cultured with LN-LECs in the presence of 10 nM SIINFEKL without (light gray, solid line) or with 2 μg/mL αCD28 (dotted lines). Isotype control-stained OT-I cells have been shown as a negative control for staining (dark gray, filled). (B) Supernatants were analyzed for IFNγ production by ELISAs, showing that in the presence of CD28 stimulation, LEC-educated OT-I cells can produce effector cytokines as effectively as BMDC-educated OT-I cells. (C) In spite of similar effector cytokine production, LEC-educated OT-I cells tend to favor a memory-like phenotype characterized by $CD44^+CD62L^+$ staining, even in the presence of CD28 stimulation (Isotype—dotted, gray circles; +CD28—solid, black squares).

FIG. 4A-F—Despite a weak effector response, LEC-educated $CD8^+$ T cells can be activated for anti-infection immunity. (A) Schematic of the experiment to characterize early memory phase response. To determine the functional potential of the transferred cells, the cells were assessed for cytokine expression (IFNγ, TNFα, IL-2) and CD107 upon ex vivo restimulation followed by intracellular staining and flow cytometric analysis. (B) LEC-educated CD8+ T cells can induce cytokines and cytolytic molecules at levels similar to DC-educated CD8+ T cells. The percentage of IFNγ, CD107, TNFα, IL-2 positive cells (gated in transferred cells) is shown for LEC/DC-educated cells in the spleen. (C) The graph displays the percentage of single (IFNγ+ only, TNFα+ only, IL-2+ only), double ($IFN\gamma^+TNF\alpha^+$ or $TNF\alpha^+IL-2^+$, $IL-2^+IFN\gamma^+$) or triple ($IFN\gamma^+TNF\alpha^+IL-2^+$) positive cells in LEC/DC-educated $CD8^+$ T cells in the spleen. The data are from two independent experiments (n=5 each). Two-way ANOVA followed by Bonferroni posttest. (D-E) LEC-educated $CD8^+$ T cells not only contributed to the generation of effector CTLs against infectious pathogens but also controlled the bacterial load during infection with L.m.-OVA. (D) Schematic of the experiment. (E) Representative examples of bacterial culture plates for the differentially educated cells and without prior transfer. (F) The graph shows the bacterial burden in spleen at day 3 after infection with L.m.-OVA. The data are from one experiment (n=6), *p≤0.05 using two-tailed unpaired Student's t test.

FIG. 5A-G—Hydrogel-mediated delivery of VEGFC drives local lymphangiogenesis. (A) Hydrogel precursors and proteins containing the fibrin-binding, transglutaminase substrate peptide (Tg; yellow) are mixed and crosslinked in the presence of thrombin and the clotting factor-XIII to create hydrogels. Inset photo showcases a hydrogel (arrowhead). In the presence of MMPs, the hydrogel matrix is degraded, releasing the free protein. (B) Intravital fluorescence imaging of the release of AF750-labeled VEGFC, in soluble (sVEGFC) or gel-crosslinkable (TgVEGFC) formats, from hydrogels following intradermal implantation in the hinds of healthy wild-type BALB/c over 20 days. Mice injected with buffer only (naïve) or empty hydrogels (empty) have been shown as negative controls. (C) Release profiles of the VEGFC over the study period. (D-G) Characterization of lymphangiogenesis at the implant site and at the draining LNs 22 days after hydrogel implantation. (D-E) Fibrin-binding VEGFC (TgVEGFC) increases local skin-draining lymphatic vessels (LYVE-1+F4/80) as observed using confocal microscopy (D; scale bars=80 μm) and flow cytometry (E) relative to empty hydrogel controls. (F-G) Soluble VEGFC (sVEGFC) appears to exert more effects at the draining lymph node. (F) Tiled fluorescence micrographs (scale=300 μm) showing cross-section of the draining, brachial LNs with LYVE-1 (red) and DAPI staining (gray). (G) $gp38^+CD31^+$ LECs in the brachial LNs were counted by flow cytometry and normalized against brachial LN mass. (Data points and error bars represent mean±SD of n=3-4 measurements. *p<0.05 by Student's t-test vs. all other groups; **p<0.05 relative to all other treatment groups by one-way ANOVA).

FIG. 6A-G—Local lymphangiogenesis drives local recruitment of T cells. Hydrogels containing sVEGFC or TgVEGFC were implanted intradermally into healthy wild-type C57Bl/6 mice and after 9 or 22 days, implant sites were excised for analysis by flow cytometry and immunohistochemistry. (A) At day 9 post-implantation, there has not yet been significant increase in lymphatic vessel density (not shown), but local recruitment of $CD45^+$ cells is already increased. (A, right) Ratio of 'area-under-curve' (AUC) of $CD45^+$ pixels normalized to AUC of $LYVE-1^+$ pixels (Each data point represents ratio quantified from one field-of-view). (B) At day 22, number of live cells per mg of tissue collected, and (C) number of live $CD45^+$ cells per mg of tissue collected. (D) At day 22, a large number of infiltrating immune cells at the implant site are $CD3^+$. (E-H) Flow cytometry analysis of cell types at the implant site at (E) day 9 and (E-H) day 22 post-implantation. (E) Pie charts represent composition of all live cells detected at the implant sites, and bar graphs represent numbers of live cells within named various $CD45^+$ subsets normalized per mg of tissue. Hydrogels containing VEGFC increase the proportion of local $CD45^+$ cells over the 22 d study period, and this can be accounted for by the T cells, DCs, and other CD45+ compartments. (F-G) increased recruitment of T cells quantified as number of live $CD4^+CD8^-$ or $CD4^-CD8^+$ per mg, or as percentage of total live cells. (H) Conventional DCs (defined as $CD3e^-B220^-CD11b^+CD11c^+$) enumerated per mg of tissue isolated, or as percentage of total live cells. (Data points and error bars represent mean±SD of n=3-10 measurements pooled from up to 3 independent experiments. *p<0.05 by Student's t-test. **p<0.05 by one-way ANOVA with Tukey's post-test).

FIG. 7A-C—Lymphangiogenic sites promote generation of effector-memory cells expressing $CD44^+CD62L^-KLRG1^-CD127^+$, and can be activated to produce IFNγ. (A) OT-II cells were adoptively transferred into healthy wild-type mice 1 d before injection of hydrogels with VEGFC±OVA. 8 d later, mice were sacrificed and the implant sites were isolated and analyzed by (B) IFNγ ELISPOTs post-ex vivo re-stimulation with OVA or (C) flow cytometry for markers of memory or effector cells. Short-lived effector cells (SLECs) were defined by $CD44^+CD62L^-KLRG1^+CD127^-$ and effector-memory Tem cells were defined by $CD44^+CD62L^-KLRG1^-CD127^+$. (Each data point=one individual mouse. *p<0.05 by Student's t-test; **p<0.05 relative to all other treatment groups by one-way ANOVA).

FIG. 8A-B—Generation of CD4 and CD8 effector-memory like cells by lymphangiogenic hydrogels. (A) Experimental timeline showing OT-I and OT-II cells were adoptively transferred into healthy wild-type mice 1 d before injection of hydrogels with VEGFC and/or OVA. Mice were bled multiple times to collect blood samples for longitudinal analysis, and at 22 d post-implantation, mice were sacrificed and the implant sites and draining brachial LNs (bLNs) were isolated and analyzed by flow cytometry for memory and effector phenotype of OT-I and OT-II cells. (B) CD4 and CD8 T cells infiltrating the implant site or bLNs, or circulating in blood were gated for $CD45.1^+$ expression to define OT-I/OT-II cells versus the endogenously-derived T cells, and then stained for expression of CD44 and CD62L to define memory and effector compartments. (n=5 per group, **p<0.05 relative to all other treatment groups by one-way ANOVA).

FIG. 9A-C—Lymphangiogenic hydrogels provoke less systemic inflammation than conventional vaccines. (A) Experimental timeline. Hydrogels containing TgVEGFC and/or TgOVA were implanted intradermally into mice. As a positive control, a standard vaccine containing 50 μg soluble OVA and 50 μg CpG were injected into mice intradermally through the footpads. This group was also boosted at day 15 with the same formulation, matching published mouse vaccination schedules. (B) Serum levels of various inflammatory markers were assayed via Luminex assay at d3 post-implantation or at d35+3 d post-challenge with OVA+LPS, mimicking an infection. (C) Levels of inflammatory cytokines were assayed by Luminex assay or by ELISA (IL-15) at the hydrogel implant site at d35+3 d post-challenge with OVA+LPS. **p<0.05 via one-way ANOVA with Tukey's post-test, n=5 per group.

FIG. 10A-G. Blocking VEGFR-3 signaling in lymphangiogenic melanomas decreases $T_{Reg}$ cell infiltration and delays primary tumor growth. (A) Representative images of immunostained whole tumor sections (scale bar=500 □m, 200 □m in zoomed images) showing overall LEC density (Lyve-1, green; DAPI, cyan). (B) Quantification of LECs ($CD45^-gp38^+CD31^+$) assessed by flow cytometry. (C) Growth curves of B16-OVA or B16-OVA/VC tumor-bearing C57BL6 mice treated with control (Iso) or VEGFR-3 (□R3) blocking antibodies. Quantification of indicated cell types within the tumor at day 9 post-inoculation: (D) total leukocytes ($CD45^+$), (E) regulatory CD4+ T cells ($T_{reg}$, $CD4^+FoxP3^+$) and effector $CD8^+$ T cells ($CD62L^-CD44^+$). (F) Representative flow cytometry plots and gating strategy of tumor cells and (G) quantification of mature ($CD11c^-CD11b^+MHCII^+$) and immature ($CD11c^-CD11b^+MHCII^-$) myeloid subsets, granulocytic ($CD11c^-CD11b^+MHCII^-Ly6G^+Ly6C^{low}$) and monocytic ($CD11c^-CD11b^+MHCII^-Ly6G^+Ly6C^{low}$) MDSCs. Results represent 2 independent experiments, n=5 each. *p≤0.05, **p≤0.01 by two-tailed Student's t-test. Bar graphs shown as mean±SEM.

FIG. 11A-G. VEGF-C/VEGFR-3 signaling increases responsiveness of melanoma to immunotherapy. B16-OVA/VC tumor-bearing C57BL/6 mice, treated with control (Iso) or □VEGFR3 (□R3) blocking antibodies, received different immunotherapies after tumors became established (arrows on growth curves indicate when the immunotherapies were administered). Tumor growth curves and survival waterfall plots for (A) Antigen-specific adoptive T cell therapy (ATT) performed by intravenously (i.v.) injection of $1 \times 10^6$ ex vivo activated effector OT-I cells on day 9 after tumor cell inoculation (data pooled from 3 independent experiments, n≥5 each). (B) ATT performed in tumor-bearing mice lacking dermal lymphatics (K14-VEGFR-3-Ig mice, n=4). (C) Dendritic cell (DC) vaccination performed by intraperitoneally (i.p.) injection of $10^6$ ex vivo peptide-pulsed DCs on days 4 and 10 after tumor cell inoculation (n=6). (D to F) Vaccination on days 4, 7, and 10 with i.d. injection into the hind legs of CpG (50 □g) with (D) no antigen, (E) 10 □g OVA (data from 2 independent experiments, n≥4 each), or (F) 2 □g Trp-2-peptide-conjugated nanoparticles (NP-Trp2, n≥6). (G) Tumor growth curves and survival plot for BRAF GEM treated with control (Iso) or □VEGFR3 (□R3) blocking antibodies, followed by a combined immunotherapy of CpG+gp100 peptide (day 8 and day 12) and anti-PD-1 antibody (day 12 and every 4 days thereafter). *p≤0.05, p≤0.01, *p≤0.001 by two-tailed Student's t-test for growth curves and Log-rank (Mantel-Cox) test for survival curves. Growth curves shown as mean±SEM over time.

FIG. 12A-J. VEGFR-3 signaling increases infiltration of naïve T cells in a CCR7-dependent manner. (A to D) B16-OVA and B16-OVA/VC tumor-bearing mice treated with i.p injection of control IgG (Iso) or □VEGFR3 (□R3) blocking antibodies were euthanized on day 9 after inoculation and tumor single cell suspensions analyzed by flow cytometry (representative of 2 independent experiments, n=5 each). (A) Quantification of conventional (cony) CD4$^+$ T cells (CD45$^+$CD4$^+$FoxP3$^-$) and CD8$^+$ T cells (CD45$^+$CD8$^+$) after live/dead exclusion. (B) Phenotype of TILs (CD4 (upper graph) or CD8 (lower graph) according to CD44 and CD62L expression status. Naïve ($T_{naive}$) CD44$^-$CD62L$^+$, effector/effector memory ($T_{EM}$): CD44$^+$CD62L$^-$, central memory ($T_{04}$): CD44$^+$CD62L$^+$T. (C) Ratio of naïve versus effector CD4$^+$ or CD8$^+$ T cells. (D) CCL21 concentration as assessed by ELISA in the tumor, dLNs, and ndLNs. (E) Representative images of an immunostained section of a lymphangiogenic B16-VC tumor (scale bar=100 □m) showing CCL21 expression and CD4 infiltration within the tumor microenvironment (Lyve-1, white; CCL21, green; CD4, red; DAPI, blue). (F) CCR7 expression of TILs. B16-OVA/VC tumor bearing mice treated with control IgG (Iso) or anti-CCR7 (□CCR7) blocking antibodies were euthanized 9 days after inoculation, and tumor single cell suspensions analyzed by flow cytometry (n=6). CCR7 expression was quantified on conventional (cony) CD4$^+$ T cells (CD45$^+$CD4$^+$FoxP3$^-$CCR7$^+$), regulatory CD4$^+$ T cells (CD4$^+$FoxP3$^+$CCR7$^+$) and CD8$^+$ T cells (CD45$^+$CD8$^+$CCR7$^+$). (G) Representative flow cytometry plots of TIL phenotype based on CD62L and CD44 expression, and (H) quantification of naïve and central memory (CM) phenotype (n=6). (I) Ratio of naïve versus effector T cells. (J) B16-OVA/VC tumor-bearing mice (CD45.1) were treated with control IgG (Iso) or anti-CCR7 (□CCR7) blocking antibodies on day 0, 3 and 6 after inoculation and adoptive transfer of 1×10$^6$ naïve CD45.2$^+$ OT-I T cells was performed on day 9. Quantification of intratumoral OT-I (CD45$^+$CD3$^+$CD8$^+$CD45.2$^+$) cells analyzed on day 10 after inoculation (n≥6). *p≤0.05,  p≤0.01, *p≤0.001 by two-tailed Student's t-test or one-way ANOVA. Bar graphs shown as mean±SEM.

FIG. 13A-F. Primary human metastatic melanomas contain CCL21-expressing LECs, and expression of VEGFC positively correlates with hallmarks of tumor inflammation. (A) Representative immunofluorescence images of human primary melanoma tumor sections (10× tiles, scale bar=500 □m, 200 □m in zoom-in images) showing nuclei (DAPI, cyan) and LECs (podoplanin, green). (B) Quantification of lymphatic vessel density in healthy (when available) and tumor region of skin of melanoma patients. Paired t-test. Scatter dot plots shown as mean±SEM (n=7 for normal skin, n=14 for tumors). (C) Representative immunohistochemistry image of a human primary melanoma tumor section (scale bar=100 □m) showing intratumoral VEGF-C expression (brown). (D) Representative immunofluorescence image of an intratumoral lymphatic vessel (podoplanin, green) expressing CCL21 (red) in a section of human primary melanoma (63×, scale bar=10 □m, DAPI, blue). (E and F) Correlations of gene expression data of human primary melanoma samples from the cancer genome atlas (TCGA). (E) Heat map showing correlation between the expression of 30 genes indicative of T cell inflammation versus VEGFC, -D (FIGF), and A. Colors indicate min and max r values using non-parametric Spearman's test. (F) Dot plots of genes of interest with linear regression curve (n=103, correlation was tested using non-parametric Spearman's test).

FIG. 14A-D. Serum VEGF-C levels in human metastatic melanoma patients predict the magnitude and functionality of a systemic tumor-specific CD8$^+$ response after peptide vaccination, and act as a biomarker for the response to combined anti-PD-1 and anti-CTLA-4 immunotherapy. (A to C) Correlations of serum VEGF-C with T cell responses in human melanoma patients (n=20) enrolled in a Phase I clinical study (NCT00112229) evaluating an anti-tumor Melan-A/MART-1 peptide vaccine. (A) magnitude and (B) functionality in terms of IFN□ expression or (C) polyfunctionality in terms of IFN□, TNF□, IL-2 and CD107 expression. (D) Progression-free survival (PFS) of human melanoma patients (n=76) enrolled in a Phase II clinical study (NCT01927419) receiving combined anti-PD-1 and anti-CTLA-4 checkpoint blockade. Patients were stratified into three groups (high, mid, low) according to serum VEGF-C concentrations. *p≤0.05 by non-parametric Spearman's test for correlations, two-tailed Student's t-test for dot plots (shown as mean±SEM) and Log-rank (Mantel-Cox) test for survival curves.

FIG. 15A-F. Increased efficacy of immunotherapy in lymphangiogenic B16 melanomas depends on CCR7 signaling prior to therapy, and local activation and expansion of TILs post therapy. (A and B) B16-OVA/VC tumor-bearing mice treated with control IgG (Iso) or anti-VEGFR3 (□R3) blocking antibodies were euthanized 3 days after adoptive T cell transfer (ATT), and tumor single cell suspensions analyzed by flow cytometry (n=5, one experiment). Quantification of overall naïve CD8+(CD45$^+$CD8$^+$CD44$^-$CD62L$^+$), effector CD8+(CD45$^+$CD8$^+$CD44$^+$CD62L$^-$), and OT-I (CD45$^+$CD8$^+$CD45.1$^+$) T cells (A) in the tumor and (B) in the dLNs. (C) Tumor growth (left) and survival curves (right) of B16-OVA/VC tumor-bearing mice treated with anti-CCR7 (□CCR7), control IgG (Iso), or □R3 antibodies combined with ATT on day 9. CCR7 blockade was performed only prior to ATT (day 0, 3, and 6) (data pooled from ≥2 independent experiments, n≥15 total). (D) Tumor growth curves of B16-OVA/VC tumor-bearing mice treated with control IgG or □R3 antibodies received daily injections of the small molecular S1P inhibitor FTY720 starting on the same day as ATT was performed (day 9) (n≥5, one experiment). (E) Representative flow cytometry plots and (F) quantification of circulating CD4$^+$ and CD8$^+$ T cells (after B220 exclusion) in blood 26 days after tumor inoculation. *p≤0.05, p≤0.01, *p≤0.001 by two-tailed Student's t-test or One-way ANOVA. Bar graphs shown as mean±SEM.

FIG. 16A-D. Mice rejecting primary lymphangiogenic B16 melanomas in response to immunotherapy show epitope spreading and long-term protection. B16-OVA/VC tumor bearing mice that rejected the primary tumor following therapeutic vaccination were re-challenged with intravenous injections of 2×10$^5$ B16 wildtype (WT) or B16-OVA/VC cells (2° i.v. challenge) at least 10 days after complete regression. Mice that either received no treatment (naïve) or vaccination only (Vax only) served as control for the first challenge (1° i.d. challenge). (A) Representative images of lung metastasis and (B) quantification of metastatic nodules per lung of mice euthanized 9 days after the 2° i.v. challenge. Flow cytometry analysis of (C) effector CD4$^+$ (CD45$^+$B220$^-$CD4$^+$CD44$^+$CD62L$^-$), effector CD8$^+$ (CD45$^+$B220$^-$CD8$^+$CD44$^+$CD62L$^-$), and OVA-specific CD8$^+$ (CD45$^+$B220$^-$CD8$^+$SIINFEKL-pentamer$^+$) 23 days after inoculation and (D) circulating tumor antigen-specific CD8$^+$ T cell responses 9 days after metastatic challenge. Data pooled from 2 independent experiments, n≥3 each. *p≤0.05, p≤0.01, *p≤0.001 by one-way ANOVA. Bar graphs shown as mean±SEM.

FIG. 17A-F. VEGFR-3 blocking specifically prevents lymphangiogenesis in VEGF-C overexpressing B16 melanoma. (A) Intratumoral VEGFC concentration as assessed by ELISA (n=5) 9 days after tumor inoculation. (B) Representative images of an immunostained whole tumor section of a non-lymphangiogenic B16-OVA tumor (scale bar=500 □m) showing overall LEC density (Lyve-1, green; DAPI, cyan). (C and E) Representative flow cytometry plots and gating strategy of tumor single cell suspensions and (D) quantification of BECs (CD45⁻gp38⁻CD31⁺), macrophages (CD45⁺F4/80⁺), and (F) dendritic cell subsets: conventional DCs (CD11c⁺CD11b), cross-presenting DCs (CD11c⁺ CD11b⁻CD8⁺), and myeloid DCs (CD11c⁺CD11b⁺). Results represent 2 independent experiments, n=5 each. *p≤0.05, **p≤0.01 by two-tailed Student's t-test. Bar graphs shown as mean±SEM.

FIG. 18A-C. VEGF-C/VEGFR-3 signaling increases melanoma responsiveness to immunotherapy against endogenous B16 melanoma antigens. (A) Growth curves of B16-WT (left) or B16-VC (right) tumor-bearing mice treated with i.p injections of control (Iso) or □VEGFR3 (□R3) blocking antibodies (n=5). (B and C) Growth curves of B16-VC tumor-bearing mice treated with CpG (50 □g) and (B) no antigen or (C) in combination with 2 □g Trp-2-peptide-conjugated nanoparticles (NP-Trp2) i.d. into hind legs on day 4, 7 and 10 after tumor cell inoculation (n≥6). *p≤0.05, p≤0.01, *p≤0.001 by two-tailed Student's t-test for growth curves and Log-rank (Mantel-Cox) test for survival curves. Growth curves shown as mean±SEM over time and bar graphs as mean±SEM.

FIG. 19A-E. VEGFR3 blockade does not broadly affect cytokine expression in lymphangiogenic B16 tumors, and decreases intratumoral CCL21 levels and tumor-associated lymphangiogenesis in BRAF GEMs. (A) Intratumoral concentrations of cytokines as assessed by protein array (n=5) from B16 tumors 9 days after inoculation. (B to E) Characterization of BRAF GEM treated with i.p injections of control (Iso) or αVEGFR3 (αR3) blocking antibodies. Intratumoral concentrations of VEGF—C(B) and CCL21 (D) as assessed by ELISA (n≥6). (C) Representative images of immunostained sections (scale bar=100 □m) showing lymphatic vessels (Lyve-1, red; DAPI, blue) and (E) zoom at the lymphatic vessel with combined CCL21 staining (green). *p≤0.05 by two-tailed Student's t-test. Bar graphs shown as mean±SEM.

FIG. 21A-D. Serum VEGF-C levels in human metastatic melanoma patients mainly predicts polyfunctionality of systemic tumor-specific CD8+ response after immunotherapy. (A to D) Correlations of serum VEGF-C with T cell responses in human melanoma patients (n=20) enrolled in a Phase I clinical study (NCT00112229) evaluating an antitumor Melan-A/MART-1 peptide vaccine. Correlation of serum VEGF-C levels with T cell functionality in terms of (A) TNF□ (B) IL-2, (C) CD107, and (D) combined IFN□ and TNF□ expression. *p≤0.05 by non-parametric Spearman's test for correlations and two-tailed Student's t-test for dot plots (shown as mean±SEM).

FIG. 22A-F. VEGFC recruits T cells to populate 'cold tumors' and blockade of VEGFC signaling reduces efficacy of checkpoint blockade immunotherapy. (A) Using a genetically-modified mouse model (GEMM) of melanoma that mimics the mutations most commonly found in human melanoma, hydroxytamoxifen (OHT)-treated mice develop skin tumors within 3 weeks of induction, following which they were injected with VEGFC weekly for two weeks. Mice were sacrificed at 5 weeks post-induction of tumors and primary tumors were collected and analyzed by flow cytometry for immune cell infiltration. (B) Braf$^{V600E}$pTEN$^{-/-}$ CAT-STA mice typically develop 'cold tumors' which were very poorly infiltrated by immune cells—particularly T cells, which have the ability to kill tumor cells. However, VEGFC-treated individuals exhibited significantly increased levels of recruitment of conventional CD4 T cells and cytotoxic T cells. An insignificant increase in accumulation of immunosuppressive regulatory T cells was also seen in these mice. (C) To test the relevance of this data to immunotherapy, a related mouse model lacking expression of artificial antigens was used. After tumor induction, a typical therapeutic vaccine (gp100 melanoma antigen with CpG adjuvant) with checkpoint blockade immunotherapy (anti-PD-1; αPD-1) schedule was then followed. Blockade of VEGFC signaling commenced a week before the vaccine-checkpoint blockade schedule, through administration of an antibody against its receptor (VEGFR3), and was continued with αPD-1 for the duration of the study in order to ensure complete silencing of this signaling pathway. (D) ELISA measurements confirm the reduction in local CCL21 levels in mice that received αVEGFR3, suggesting a weakened ability to recruit T cells. (E) Tumors in αVEGFR3-treated mice grow more rapidly than in control mice treated with an isotype control antibody. (F) Survival of tumor-bearing mice was tracked longitudinally, showing that mice treated with αVEGFR3 succumb earlier to their disease. *p<0.05 for n=3-7 biological replicates via Mann-Whitney U-test (A-E) or via Mantel-Cox log rank test (F).

FIG. 23A-E. Lymphatic expansion in VEGFC-overexpressing cancer vaccines promotes systemic activation of antigen-specific T cell immunity. (A) Healthy mice were vaccinated with either x-irradiated B16OVA/VEGFC plus CFA/OVA (VEGFC vax) or with control irradiated B16OVA and CFA/OVA (ctrl vax). (B) Following the vaccination schedule described in A, antigen-specific CD8+ T cells in vaccinated dLNs and spleen were re-stimulated with a MHCI-restricted OVA peptide (SIINFEKL) and IFNγ production was measured by ELISA and intracellular staining. (C) Healthy mice were vaccinated with either x-irradiated B16OVA/VEGFC plus Imiquimod (VEGFC vax) or with control irradiated B16OVA plus Imiquimod (ctrl vax). Imiquimod vas applied on the cell injection site every other day starting at day 2 from cell injection. (D) Following the vaccination protocol described in C, antigen-specific CD8+ T cells in vaccine-dLNs and spleen were re-stimulated with either a MHCI-restricted OVA peptide (SIINFEKL, left panels) or MHCI-restricted mixed Trp2 and gp100 peptides (right panels) and IFNγ secretion was measured by ELISA. (E) Correlation between IFNγ secretion in dLNs or spleen and LEC proportion in the vaccine injection site following the vaccination schedule described in C. IFNγ production was measured post ex vivo T cell re-stimulation with the SIIKFEKL peptide. *p<0.05, **<0.01. dLNs: draining-lymph nodes. CFA: Complete Freund's Adjuvant. B16OVA/VEGFC: VEGFC-overexpressing B16OVA.

DESCRIPTION OF ILLUSTRATIVE EMBODIMENTS

Figure 19A:
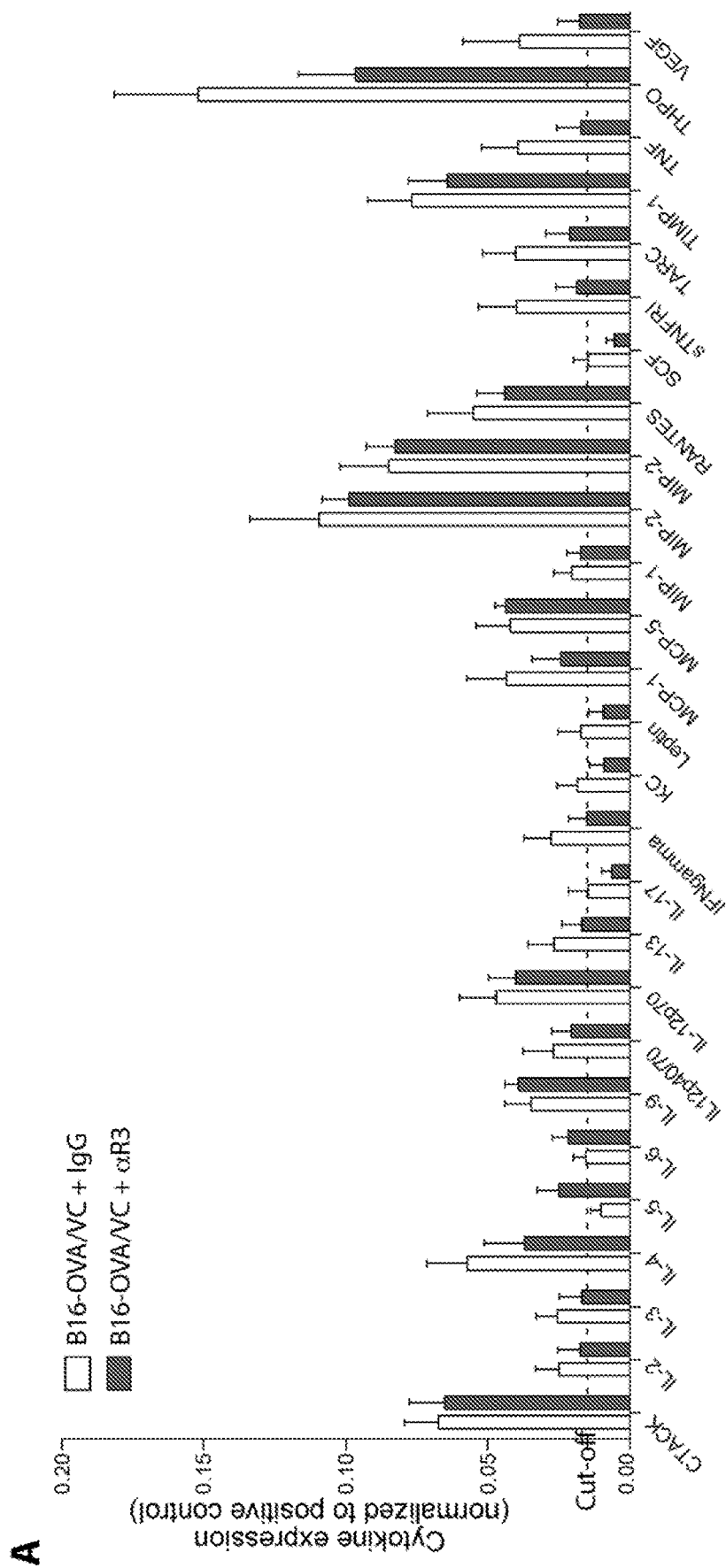

The inventors have observed that cells lining the lymphatic vessels, notably lymphatic endothelial cells (LECs), can serve as APCs, and that LECs may play a pivotal role in induction of immunological memory. LECs can collect exogenous antigens and cross-present them on major histocompatibility complex I (MHC I), a process more associated with specific classes of DCs (Hirosue et al., 2014; Lund et al., 2012; Card et al., 2014; Fletcher et al., 2010; Lukacs-Kornek et al., 2011; Malhotra et al., 2012). Classically, antigens from cytoplasmic location (such as viral proteins) are processed and presented on MHC I; as such, this MHC serves as a sensor for antigens present endogenously within the cells. Some APCs, however, notably CD8$^+$ DCs, are capable of processing exogenous antigen and loading it on MHC I, a process referred to as cross-presentation (den Hann et al., 2000; Schulz et al., 2002). The inventors have observed that LECs can cross-present exogenous antigens as well. It is thought that antigenic epitopes presented on MCH I can stimulate responses in the CD8 T cell compartment. In addition to this mode of antigen presentation, APCs are also able to present exogenous antigens on major histocompatibility complex II (MHC II), which stimulates responses in the CD4 T cell compartment. The inventors have observed that LECs can do this as well (Dubrot et al., 2014) However, prior art suggests that LEC-educated T cells tend to exhibit suboptimal activation profiles, in similar fashion to suppressed T cells (Hirosue et al., 2014; Lund et al., 2012; Card et al., 2014; Fletcher et al., 2010; Lukacs-Kornek et al., 2011; Hirosue et al., 2015; Tewalt et al., 2012).

II. METHODS AND COMPOSITIONS

The inventors describe here the use of lymphangiogenesis inducers and antigens that serve to evoke protective immune responses. the inventors find that LECs can function as powerful APCs in vaccination from the perspective of immunological memory and memory recall responses. Embodiments focus the way in which LECs and lymphangiogenesis may be manipulated to induce immunological responses.

III. IMMUNOTHERAPIES

In some embodiments, the methods include the administration of an immunotherapy. Exemplary immunotherapies are described below.

A. Checkpoint Inhibitors

An "immune checkpoint inhibitor" is any molecule that directly or indirectly inhibits, partially or completely, an immune checkpoint pathway. Without wishing to be bound by any particular theory, it is generally thought that immune checkpoint pathways function to turn on or off aspects of the immune system, particularly T cells. Following activation of a T cell, a number of inhibitory receptors can be upregulated and present on the surface of the T cell in order to suppress the immune response at the appropriate time. In the case of persistent immune stimulation, such as with chronic viral infection, for example, immune checkpoint pathways can suppress the immune response and lead to immune exhaustion. Examples of immune checkpoint pathways include, without limitation, PD-1/PD-L1, CTLA4/B7-1, TIM-3, LAG3, By-He, H4, HAVCR2, IDOL CD276 and VTCN1. In the instance of the PD-1/PD-L1 immune checkpoint pathway, an inhibitor may bind to PD-1 or to PD-L1 and prevent interaction between the receptor and ligand. Therefore, the inhibitor may be an anti-PD-1 antibody or anti-PD-L1 antibody. Similarly, in the instance of the CTLA4/B7-1 immune checkpoint pathway, an inhibitor may bind to CTLA4 or to B7-1 and prevent interaction between the receptor and ligand. Further examples of immune checkpoint inhibitors can be found, for example, in WO2014/144885. Such immune checkpoint inhibitors are incorporated by reference herein. In some embodiments of any one of the methods, compositions or kits provided, the immune checkpoint inhibitor is a small molecule inhibitor of an immune checkpoint pathway. In some embodiments of any one of the methods, compositions or kits provided, the immune checkpoint inhibitor is a polypeptide that inhibits an immune checkpoint pathway. In some embodiments of any one of the methods, compositions or kits provided, the inhibitor is a fusion protein. In some embodiments of any one of the methods, compositions or kits provided, the immune checkpoint inhibitor is an antibody. In some embodiments of any one of the methods, compositions or kits provided, the antibody is a monoclonal antibody.

Non-limiting examples of immune checkpoint inhibitors include fully human monoclonal antibodies, such as RG7446, BMS-936558/MDX-1106, BMS-936559 (anti-PDL1 antibody), Yervoy/ipilimumab (anti-CTLA-4 checkpoint inhibitor), and Tremelimumab (CTLA-4 blocking antibody); humanized antibodies, such as pidilizumab (CT-011, CureTech Ltd.) and lambrolizumab (MK-3475, Merck, PD-1 blocker); and fusion proteins, such as AMP-224 (Merck). Other examples of checkpoint inhibitors include anti-OX40, PD-L1 monoclonal Antibody (Anti-B7-H1; MEDI4736), Nivolumab (BMS-936558, Bristol-Myers Squibb, anti-PD1 antibody), CT-011 (anti-PD1 antibody), BY55 monoclonal antibody, MPLDL3280A (anti-PDL1 antibody), and MSB0010718C (anti-PDL1 antibody), MDX-1105 (Medarex), MPDL3280A (Genentech), Anti-KIR antibodies such as lirlumab (Innate Pharma) and IPH2101 (Innate Pharma) may perform similar functions in NK cells. Further examples of checkpoint inhibitors include agonistic anti-4-1bb antibody; agonistic anti-CD27 antibody; agonistic anti-GTIR antibody; agonistic anti-OX40 antibody; and antagonistic anti-TIM3 antibody.

B. Additional Immunotherapies and Agents

In some embodiments, the method further comprises administration of an immunotherapy or an additional agent described herein. In some embodiments, the additional agent is an immunostimulator. The term "immunostimulator" as used herein refers to a compound that can stimulate an immune response in a subject, and may include an adjuvant. In some embodiments, an immunostimulator is an agent that does not constitute a specific antigen, but can boost the strength and longevity of an immune response to an antigen. Such immunostimulators may include, but are not limited to stimulators of pattern recognition receptors, such as Toll-like receptors, RIG-1 and NOD-like receptors (NLR), mineral salts, such as alum, alum combined with monphosphoryl lipid (MPL) A of Enterobacteria, such as *Escherihia coli*, *Salmonella minnesota*, *Salmonella typhimurium*, or *Shigella flexneri* or specifically with MPL® (ASO4), MPL A of above-mentioned bacteria separately, saponins, such as QS-21, Quil-A, ISCOMs, ISCOMATRIX, emulsions such as MF59, Montanide, ISA 51 and ISA 720, AS02 (QS21+squalene+MPL.), liposomes and liposomal formulations such as ASO1, synthesized or specifically prepared microparticles and microcarriers such as bacteria-derived outer membrane vesicles (OMV) of *N. gonorrheae*, *Chlamydia trachomatis* and others, or chitosan particles, depot-forming agents, such as Pluronic block co-polymers, specifically modified or prepared peptides, such as muramyl dipeptide, aminoalkyl glucosaminide 4-phosphates, such as RC529, or proteins, such as bacterial toxoids or toxin fragments.

In some embodiments, the additional agent comprises an agonist for pattern recognition receptors (PRR), including, but not limited to Toll-Like Receptors (TLRs), specifically TLRs 2, 3, 4, 5, 7, 8, 9 and/or combinations thereof. In some embodiments, additional agents comprise agonists for Toll-Like Receptors 3, agonists for Toll-Like Receptors 7 and 8, or agonists for Toll-Like Receptor 9; preferably the recited immunostimulators comprise imidazoquinolines; such as R848; adenine derivatives, such as those disclosed in U.S. Pat. No. 6,329,381, U.S. Published Patent Application 2010/0075995, or WO 2010/018132; immunostimulatory DNA; or immunostimulatory RNA. In some embodiments, the additional agents also may comprise immunostimulatory RNA molecules, such as but not limited to dsRNA, poly I:C or poly I:poly C12U (available as Ampligen®, both poly I:C and poly I:polyC12U being known as TLR3 stimulants), and/or those disclosed in F. Heil et al., "Species-Specific Recognition of Single-Stranded RNA via Toll-like Receptor 7 and 8" Science 303(5663), 1526-1529 (2004); J. Vollmer et al., "Immune modulation by chemically modified ribonucleosides and oligoribonucleotides" WO 2008033432 A2; A. Forsbach et al., "Immunostimulatory oligoribonucleotides containing specific sequence motif(s) and targeting the Toll-like receptor 8 pathway" WO 2007062107 A2; E. Uhlmann et al., "Modified oligoribonucleotide analogs with enhanced immunostimulatory activity" U.S. Pat. Appl. Publ. US 2006241076; G. Lipford et al., "Immunostimulatory viral RNA oligonucleotides and use for treating cancer and infections" WO 2005097993 A2; G. Lipford et al., "Immunostimulatory G,U-containing oligoribonucleotides, compositions, and screening methods" WO 2003086280 A2. In some embodiments, an additional agent may be a TLR-4 agonist, such as bacterial lipopolysaccharide (LPS), VSV-G, and/or HMGB-1. In some embodiments, additional agents may comprise TLR-5 agonists, such as flagellin, or portions or derivatives thereof, including but not limited to those disclosed in U.S. Pat. Nos. 6,130,082, 6,585,980, and 7,192,725.

In some embodiments, additional agents may be proinflammatory stimuli released from necrotic cells (e.g., urate crystals). In some embodiments, additional agents may be activated components of the complement cascade (e.g., CD21, CD35, etc.). In some embodiments, additional agents may be activated components of immune complexes. Additional agents also include complement receptor agonists, such as a molecule that binds to CD21 or CD35. In some embodiments, the complement receptor agonist induces endogenous complement opsonization of the synthetic nanocarrier. In some embodiments, immunostimulators are cytokines, which are small proteins or biological factors (in the range of 5 kD-20 kD) that are released by cells and have specific effects on cell-cell interaction, communication and behavior of other cells. In some embodiments, the cytokine receptor agonist is a small molecule, antibody, fusion protein, or aptamer.

In some embodiments, the additional agent is an antibody-drug conjugate. In some embodiments, the antibody-drug conjugate is selected from gemtuzumab ozogamicin, brentuximab vedotin, and trastuzumab emtansine.

In some embodiments, the additional agent is a chimeric antigen receptor (CAR). CARs are artificial T cell receptors which graft a specificity onto an immune effector cell. The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g. neuroblastoma cells). The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows the scFv to orient in different directions to enable antigen binding. The transmembrane domain is a typical hydrophobic alpha helix usually derived from the original molecule of the signalling endodomain which protrudes into the cell and transmits the desired signal.

Additional agents that can act as immunostimulators include STING agonists. The STING pathway is a pathway that is involved in the detection of cytosolic DNA. Stimulator of interferon genes (STING), also known as transmembrane protein 173 (TMEM173) and MPYS/MITA/ERIS, is a protein that in humans is encoded by the TMEM173 gene. STING plays an important role in innate immunity. STING induces type I interferon production when cells are infected with intracellular pathogens, such as viruses, mycobacteria and intracellular parasites. Type I interferon, mediated by STING, protects infected cells and nearby cells from local infection in an autocrine and paracrine manner.

STING is encoded by the TMEM173 gene. It works as both a direct cytosolic DNA sensor (CDS) and an adaptor protein in Type I interferon signaling through different molecular mechanisms. It has been shown to activate downstream transcription factors STATE and IRF3 through TBK1, which are responsible for antiviral response and innate immune response against intracellular pathogen.

STING resides in the endoplasmic reticulum, but in the presence of cytosolic DNA, the sensor cGAS binds to the DNA and forms cyclic dinucleotides. This di-nucleotide binds to STING and promotes its aggregation and translocation from the ER through the Golgi to perinuclear sites. There, STING complexes with TBK1 and promotes its phosphorylation. Once TBK1 is phosphorylated, it phosphorylates the transcription factor IRF3 that dimerices and traslocates to the nucleus, where it activates the transcription of type I IFN and other innate immune genes.

STING agonsists can include 3'3'-cGAMP fluorinated, fluorinated cyclic diadenylate monophosphate, ZDHHC1, 2'3'-c-di-AM(PS)2 (Rp,Rp), 2'2'-cGAMP, c-di-IMP, 2'3'-cGAM(PS)2 (Rp/Sp), 3'3'-cGAMP, DMXAA, 2'3'-cGAMP, c-di-GMP, c-di-GMP, 2'3'-c-di-GMP, 2'3'-c-di-AMP, c-di-GMP Fluorinated, and c-di-AMP.

In some embodiments, the immunotherapy includes cytolytic viral therapy, such administration of an onocolytic virus or modified version thereof. Oncolytic viruses include oncolytic herpes simplex virus, adenovirus, reovirus, measles, Newcastle disease virus, and vaccinia virus.

C. Vaccine Immunotherapies

The methods of the disclosure may also include the administration of vaccines. As used herein, the term in vitro administration refers to manipulations performed on cells removed from or outside of a subject, including, but not limited to cells in culture. The term ex vivo administration refers to cells which have been manipulated in vitro, and are subsequently administered to a subject. The term in vivo administration includes all manipulations performed within a subject, including administrations.

In certain aspects of the present disclosure, the compositions may be administered either in vitro, ex vivo, or in vivo. In certain in vitro embodiments, autologous T cells are incubated with compositions of this disclosure. The cells can then be used for in vitro analysis, or alternatively for ex vivo administration.

Method aspects of the disclosure include vaccinating a subject with a variety of different immunotherapeutic compositions. In some embodiments, the methods further comprise administration of immune cells to the subject. In some embodiments, the immune cells are autologous. In some embodiments, the immune cells has been contacted with an antigen. In some embodiments, the antigen is an antigen expressed by the subject's cancer cells. In some embodiments, the antigen is cell free. The term "cell free" refers to a composition that does not have any cellular components. In some embodiments, the antigen is an extract from the patient's tumor. In some embodiments, the antigen is a polypeptide. In some embodiments, the antigen comprises one or more of tumor cell lysate, apoptotic tumor cell, tumor-associated antigen, and tumor-derived mRNA. In some embodiments, the immune cell has been contacted with a maturation agent. In some embodiments, the maturation agent is one or more of GM-CSF, IL-1β, TNF-α, and PGE2. In some embodiments, the immune cell comprises a chimeric antigen receptor.

In some embodiments, the immune cell is an antigen presenting cells. Antigen-presenting cells can be used as a cancer vaccine. Examples of the antigen-presenting cells include dendritic cells, macrophages, B cells, and tumor cells (false antigen-presenting cells) in which a T cell stimulation factor (e.g., B7 or 4-1 BBL) and the like is forcibly expressed by, for example, gene transfer. In some embodiments, the antigen presenting cell is a dendritic cell.

The route of administration of the immune cell may be, for example, intratumoral, intracutaneous, subcutaneous, intravenous, intralymphatic, and intraperitoneal administrations. In some embodiments, the administration is intratumoral or intralymphatic. In some embodiments, the immune cells are administered directly into a cancer tissue or a lymph node.

In some embodiments, the immune cell is a T cell. T cells can also be used as a cancer vaccine. The T cells may be ones that have been contacted with an antigen or with antigen-presenting cells. For example, APCs may be cultured with tumor antigen specific to the patient's cancer to differentiate them, into, for example, CD8-positive cytotoxic T lymphocytes (CTLs) or CD4-positive helper T cells. The T cells thus established may be administered to an individual with cancer.

The origin of the naive T cells is not specifically limited and it may be derived from, for example, peripheral blood of a vertebrate animal. The naive T cell used may be CD8-positive cells or CD4-positive cells isolated from a PBMC fraction. In some embodiments, the naive T cells are CD8-positive cells or CD4-positive cells mixed with other cells and components without being isolated from the PBMC fraction in terms of the efficiency of inducing CTLs. For example, when cells of a PBMC fraction are cultured in a medium supplemented with serum and tumor antigen, the PBMCs differentiate into dendritic cell precursors. The dendritic cell precursors then bind to the peptide and differentiate into dendritic cells as the antigen-presenting cells presenting this peptide/tumor antigen. The antigen-presenting cells stimulate the CD8-positive T cells in the PBMCs to differentiate them into CTLs. Thus, the CTLs capable of recognizing the added peptide can be obtained. The CTLs thus obtained may be isolated and used as the cancer vaccine as they are. Alternatively, they may be cultured further in the presence of interleukin such as IL-2, the antigen-presenting cell, and tumor antigen before used as the cancer vaccine. The route of their administration is not specifically limited and examples include intracutaneous, subcutaneous, intravenous, and intratumoral administrations.

IV. ANTIGEN

The methods of the disclosure may include the administration of an antigen. In one embodiment, the antigen is a cancer antigen. In a further embodiment, the antigen is specific to the patient's cancer. In some embodiments, the antigen is chemically or recombinantly synthesized. In some embodiments, the antigen comprises one or more of tumor cell lysate, apoptotic tumor cell, tumor-associated antigen, and tumor-derived mRNA. In some embodiments, the antigen is cell-free. The antigen may be one known in the art or described herein. Non-limiting examples of cancer antigens include antigenic fragments and polypeptides from VEGFR-2, MMPs, Survivin, TEM8, PMSA, CA125, folate binding protein (FBP), HER2/neu, MUC1, NYESO 1, PSA, Carcinoembryonic antigen (CEA), a-fetoprotein (AFP), heat shock proteins (e.g., hsp70 or hsp90 proteins) from a particular type of tumor, MICAS ligands of NKG2D, epithelial cell adhesion molecule (Ep-CAM/TACSTD1), mesothelin, tumor-associated glycoprotein 72 (TAG-72), gp100, Melan-A, MART-1, KDR, RCAS1, MDA7, cancer-associated viral vaccines (e.g., human papillomavirus antigens), prostate specific antigen (PSA, PSMA), RAGE (renal antigen), CAMEL (CTL-recognized antigen on melanoma), CT antigens (such as MAGE-B5, -B6, -C2, -C3, and D; Mage-12; CT10; NY-ESO-1, SSX-2, GAGE, BAGE, MAGE, and SAGE), mucin antigens (e.g., MUC1, mucin-CA125, etc.), cancer-associated ganglioside antigens, tyrosinase, gp75, C-myc, Mart1, MelanA, MUM-1, MUM-2, MUM-3, HLA-B7, Ep-CAM, tumor-derived heat shock proteins, and the like (see also, e.g., Acres et al., Curr Opin Mol Ther 2004 February, 6:40-7; Taylor-Papadimitriou et al., Biochim Biophys Acta. 1999 Oct. 8; 1455(2-3):301-13; Emens et al., Cancer Biol Ther. 2003 July-August; 2(4 Suppl 1):5161-8; and Ohshima et al., Int J Cancer. 2001 Jul. 1; 93(1):91-6). Other exemplary cancer antigen targets include CA 195 tumor-associated antigen-like antigen (see, e.g., U.S. Pat. No. 5,324,822) and female urine squamous cell carcinoma-like antigens (see, e.g., U.S. Pat. No. 5,306,811), and the breast cell cancer antigens described in U.S. Pat. No. 4,960,716.

The cancer antigen may be an epithelial cancer antigen, (e.g., breast, gastrointestinal, lung), a prostate specific cancer antigen (PSA) or prostate specific membrane antigen (PSMA), a bladder cancer antigen, a skin (melanoma) cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, or a colorectal cancer antigen. A cancer antigen can also be an antigen specifically expressed by the patient's cancer or an antigen known to be specifically expressed by the patient's cancer.

V. NUCLEIC ACIDS

In certain embodiments, there are recombinant nucleic acids encoding the proteins, polypeptides, or peptides described herein. Polynucleotides contemplated for use in methods and compositions include those encoding lymphangiogenesis inducers and antigens such as a bacterial antigen, a viral antigen, a fungal antigen, a protozoal antigen, a helminth antigen or a cancer antigen.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or fewer in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein (see above).

In particular embodiments, there are isolated nucleic acid segments and recombinant vectors incorporating nucleic acid sequences that encode a polypeptide (e.g., a lymphangiogenesis inducer) that induces formation of lymphatic vessels from pre-existing lymphatic vessels. The term "recombinant" may be used in conjunction with a polypeptide or the name of a specific polypeptide, and this generally refers to a polypeptide produced from a nucleic acid molecule that has been manipulated in vitro or that is a replication product of such a molecule.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain embodiments, there are polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence provided herein using the methods described herein (e.g., BLAST analysis using standard parameters). In certain aspects, the isolated polynucleotide will comprise a nucleotide sequence encoding a polypeptide that has at least 90%, preferably 95% and above, identity to an amino acid sequence described herein, over the entire length of the sequence; or a nucleotide sequence complementary to said isolated polynucleotide.

A. Vectors

Polypeptides may be encoded by a nucleic acid molecule. The nucleic acid molecule can be in the form of a nucleic acid vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). Vectors may be used in a host cell to produce lymphangiogenesis inducers and antigens such as a bacterial antigen, a viral antigen, a fungal antigen, a protozoal antigen, a helminth antigen or a cancer antigen.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

B. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

C. Expression Systems

Numerous expression systems exist that comprise at least a part or all of the compositions discussed above. Prokaryote- and/or eukaryote-based systems can be employed for use with an embodiment to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems, other examples of expression systems include STRATAGENE®'s COMPLETE CONTROL Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

VI. PROTEINACEOUS COMPOSITIONS

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that bacteria containing such a variant may be implemented in compositions and methods. Consequently, a protein need not be isolated.

The term "functionally equivalent codon" is used herein to refer to codons that encode the same amino acid, such as the six codons for arginine or serine, and also refers to codons that encode biologically equivalent amino acids (see Table, below).

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent, or even an improved, second-generation molecule. For example, certain amino acids may be substituted for other amino acids in a protein structure without appreciable loss of interactive binding capacity, ability to induce lymphangiogenesis or antigenicity with structures such as, for example, lymphangiogenesis inducers and antigens such as a bacterial antigen, a viral antigen, a fungal antigen, a protozoal antigen, a helminth antigen or a cancer antigen. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

It is contemplated that in compositions there is between about 0.001 mg and about 10 mg of total biomolecule, protein, polypeptide, carbohydrate, polysaccharide, lipid, nucleic acid, fatty acid, glycolipid, sterol, polyterpene, glycerolipid or a combination of these per ml. Thus, the concentration of a biomolecule, a protein, a polypeptide, a carbohydrate, a polysaccharide, a lipid, a nucleic acid, a fatty acid, a glycolipid, a sterol, a polyterpene, a glycerolipid or a combination of these in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be a lymphangiogenesis inducer and/or antigens such as a bacterial antigen, a viral antigen, a fungal antigen, a protozoal antigen, a helminth antigen or a cancer antigen, and may be used in combination with lymphangiogenesis inducers and antigens such as a bacterial antigen, a viral antigen, a fungal antigen, a protozoal antigen, a helminth antigen or a cancer antigen described herein.

Included are polypeptides with 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to a peptide of the disclosure. The peptide or polypeptide may have one or more conservative or non-conservative substitutions. Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

The polypeptides described herein may include 1, 2, 3, 4, 5, 6, 7, 8, 9, 10, 11, 12, 13, 14, 15, or more (or any derivable range therein) variant amino acids within at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of a peptide or polypeptide of the disclosure.

A polypeptide segment as described herein may include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein of a peptide or polypeptide of the disclosure.

The polypeptides described herein may be of a fixed length of at least, at most, or exactly 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more amino acids (or any derivable range therein).

A linker sequence may be included in the compositions of the disclosure. For example, a linker having at least, at most, or exactly 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids (or any derivable range therein) may separate two polypeptide components in the compositions of the disclosure.

A. Polypeptides and Polypeptide Production

Embodiments involve lymphangiogenesis inducers and antigens such as a bacterial antigen, a viral antigen, a fungal antigen, a protozoal antigen, a helminth antigen or a cancer antigen for use in various aspects described herein. For example, lymphangiogenesis inducers and antigens such as a bacterial antigen, a viral antigen, a fungal antigen, a protozoal antigen, a helminth antigen or a cancer antigen are assayed for or used in methods of eliciting immune responses, protective immune responses and inducing immune tolerance. In specific embodiments, all or part of proteins described herein can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence that encodes a peptide or polypeptide is inserted into an expression vector, transformed or transfected into an appropriate host cell and cultivated under conditions suitable for expression.

One embodiment includes the use of gene transfer to cells, including microorganisms, for the production and/or presentation of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are discussed herein. Alternatively, the protein to be produced may be an endogenous protein normally synthesized by the cell used for protein production.

In a certain aspects a lymphangiogenesis inducer comprises substantially some or all of a lymphangiogenesis inducing protein which has at least 85% identity, at least 90% identity, at least 95% identity, or at least 97-99% identity, including all values and ranges there between, to a sequence selected over the length of the fragment sequence. In yet other aspects, antigens such as a bacterial antigen, a viral antigen, a fungal antigen, a protozoal antigen, a helminth antigen or a cancer antigen comprises substantially some or all of the antigenic portion a protein which has at least 85% identity, at least 90% identity, at least 95% identity, or at least 97-99% identity, including all values and ranges there between, to a sequence selected over the length of the fragment sequence.

B. Adjuvants

In other embodiments an immune adjuvant is included in a composition comprising a lymphangiogenesis inducer and an antigen such as a bacterial antigen, a viral antigen, a fungal antigen, a protozoal antigen, a helminth antigen or a cancer antigen or is directly fused or otherwise linked to a lymphangiogenesis inducer or an antigen in order to enhance the efficacy of the immunotherapeutic. In certain aspects the immune adjuvant may be a toll-like receptor (TLR) agonist. TLR agonists comprise flagellins from *Salmonella enterica* or *Vibrio cholerae*. In certain aspects the adjuvant in Flagellin-1 or Flagellin-2. TLR agonists may be specific for certain TLR classes (i.e., TLR5, TLR7 or TLR9 agonists) and may be presented in any combination or as any modification. Examples of such immune adjuvants are described in WO 2012/021834, the contents of which are incorporated herein by reference. Poly ICLC, a TLR3 ligand is also contemplated for use with a lymphangiogenesis inducer and an antigen comprising composition. In some embodiments the lymphangiogenesis inducer and the antigen and Poly ICLC is delivered separately from the antibody antigen fusion polypeptide. In one embodiment, the Poly ICLC is as described in U.S. Pat. No. 7,439,349, the contents of which are incorporated herein by reference. In one embodiment, the Poly ICLC is Hiltonol®. Interleukins are also contemplated as adjuvants that may be administered alongside, separately or fused to a lymphangiogenesis inducer or an antigen. Non-limiting examples of such interleukins are IL-21, IL-2, IL-9 and IL-10. In some embodiments the interleukin proteins are human interleukins. In certain aspects the adjuvant is an HLA-DR antigen-associated invariant chain that augments antigen processing. In certain aspects the adjuvant is interferon alpha. In yet other embodiments the adjuvant is a toxin that will deliver a death signal to cells also receiving an myelin sheath protein or component, thereby augmenting immunotherapeutic efficiency. One example of such a toxin is PE38. Any adjuvant may be delivered in fused or conjugated form with a lymphangiogenesis inducer and an antigen or may be delivered concomitantly as part of the same composition or preparation without fusion or direct conjugation.

C. Tolerogenic Adjuvants

In certain embodiments the immune adjuvant may be a tolerogenic adjuvant. In certain instances a tolerogenic adjuvant may refer to an adjuvant that is utilized for tolerogenic immunization, where the aim of immunization with an antigen is to generate an immune response such that the antigen is tolerated by an immunizaed subject. In certain aspects, the goal of a tolerogenic adjuvant is to enhance tolerogenic immunization such that tolerance to an antigen is further enhanced. In certain embodiments a tolerogenic adjuvant is used to tolerize autoimmunity. In yet other aspects, a tolerogenic adjuvant is used to tolerize harmful autoimmunity. In some embodiments the tolerogenic adjuvant is an immunosuppressant. In yet other embodiments the tolerogenic adjuvant is dexamethasone, FK506 (Tacrolimus), cholera toxin B subunit, *Escherichia coli* heat-labile enterotoxin B subunit, IFN-beta, glucocorticoids, vitamin D3, or vitamin D3 analogues. In certain aspects the tolerogenic adjuvant is administered concurrently with a lymphangiogenesis inducer and an antigen as an immunotherapeutic. In other aspects a tolerogenic adjuvant is administered before or after administration of a lymphangiogenesis inducer and an antigen. In yet other embodiments two or more tolerogenic adjuvants are administered concurrently, before or after administration of a lymphangiogenesis inducer and an antigen. In certain aspects, the tolerogenic adjuvant may be fused, conjugated or otherwise linked to the lymphangiogenesis inducer and antigen. In one embodiment, the tolerogenic adjuvant is interleukin-10 (IL-10). In another embodiment IL-10 is co-administered with the lymphangiogenesis inducer and antigen. In certain aspects, IL-10 is fused by recombinant methods. In other aspects IL-10 is conjugated. In other embodiments IL-10 is linked by coupling or other modular domains.

D. VEGF Proteins

Human VEGF-C includes the following sequence:

(SEQ ID NO: 1)
MHLLGFFSVACSLLAAALLPGPREAPAAAAAFESGLDLSDAEPDAGEATA

YASKDLEEQLRSVSSVDELMTVLYPEYWKMYKCQLRKGGWQHNREQANLN

SRTEETIKFAAAHYNTEILKSIDNEWRKTQCMPREVCIDVGKEFGVATNT

FFKPPCVSVYRCGGCCNSEGLQCMNTSTSYLSKTLFEITVPLSQGPKPVT

ISFANHTSCRCMSKLDVYRQVHSIIRRSLPATLPQCQAANKTCPTNYMWN

NHICRCLAQEDFMFSSDAGDDSTDGFHDICGPNKELDEETCQCVCRAGLR

PASCGPHKELDRNSCQCVCKNKLFPSQCGANREFDENTCQCVCKRTCPRN

QPLNPGKCACECTESPQKCLLKGKKFHHQTCSCYRRPCTNRQKACEPGFS

YSEEVCRCVPSYWKRPQMS.

MHLLGFFSVACSLLAAALLPGPREAPAAAAA (SEQ ID NO:7) is the signal peptide for protein secretion. It is usually removed and exchanged to another leading sequence for protein expression. The N-terminal propeptide: FESGLDLSDAEPDAGEATAYASKDLE-EQLRSVSSVDELMTVLYPEYWKMYKCQLRK GGWQHNREQANLNSRTEETIKFAA (SEQ ID NO:8) has been reported to be involved in the binding of the co-receptor Nrp-1 and enhanced the binding to Nrp-2, which can act to modulate lymphangiogenic effect (or kinetics) triggered by VEGF-C.

The C-terminal propeptides: SLPATLPQCQAANKTC-PTNYMWNNHICRCLAQEDFMFSSDAGDD-STDGFHDICGPN KELDEETCQCVCRAGLRPASCGPH-KELDRNSCQCVCKNKLFPSQCGANREFDENTC QCVCKRTCPRNQPLNPGKCACECTESPQKCLL-KGKKFHHQTCSCYRRPCTNRQKAC EPGFSYS-EEVCRCVPSYWKRPQMS (SEQ ID NO: 9), CGPN-KELDEETCQCVCRAGLRPASCGPHKELDRN-SCQCVCKNKLFPSQCGANREFD ENTCQCVCKR-TCPRNQPLNPGKCACECTESPQKCLLKGKKF-HHQTCSCYRRPCTNR QKACEPGFSYSEEVCRCVP-SYWKRPQMS (SEQ ID NO:10), and CGPN-KELDEETCQCVCRAGLRPASCGPHKELDRN-SCQCVCKNKLFPSQCGANREFD ENTCQCVCKRT-CPRNQPLNPGKCACEC (SEQ ID NO:11) contain repeats of 16 amino-acids repeats of C-X(10)-C-X-C-X(1-3)-C. These alternate patterns of CXCXC were also found in other angiogenic proteins. It is contemplated that variants of VEGF-C may comprise only conservative mutations in the C-X(10)-C-X-C-X(1-3)-C region. It is also contemplated that non-conservative mutations may be tolerated outside of this region and retain the functional activities of this protein.

The mature VEGF-C human sequence comprises: AHYNTEILKSIDNEWRKTQCMPREVCIDVGKEFG-VATNTFFKPPCVSVYRCGGCCNS EGLQCMNTST-SYLSKTLFEITVPLSQGPKPVTISFANHTSCRCMSK-LDVYRQVHSIIRR (SEQ ID NO:12). In some embodiments, the VEGF-C sequence comprises: AHYN-TEILKSIDNEWRKTQCMPREVCIDVGKEFG-VATNTFFKPPCVSVYRCGGCCNS (SEQ ID NO: 13)
AHYNTEILKSIDNEWRKTQCMPREVCIDVGKEFGVATNTFFKPPCVSVY

RCGGCCNSEGLQCMNTSTSYLSKTLFEITVPLSQGPKPVTISFANHTSC

RCMSKLDVYRQ.

Human VEGF-D sequence is included as SEQ ID NO:3. This protein comprises a conserved region of repeats of 16 amino-acids repeats of C-X(10)-C-X-C-X(1-3)-C that are found in other angiogenic proteins: CPIDMLWDSNKCK-CVLQEENPLAGTEDHSHLQEPALCGPHMMFD-EDRCECVCKTPC PKDLIQHPKNCSCFECKES-LETCCQKHKLFHPDTCSCEDRC (SEQ ID NO:14). It is contemplated that variants of VEGF-C may comprise only conservative mutations in the C-X(10)-C-X-C-X(1-3)-C region. It is also contemplated that non-conservative mutations may be tolerated outside of this region and retain the functional activities of this protein.

The mature VEGF-C human sequence comprises:

(SEQ ID NO: 15)
FAATFYDIETLKVIDEEWQRTQCSPRETCVEVASELGKSTNTFFKPPCV

NVFRCGGCCNEESLICMNTSTSYISKQLFEISVPLTSVPELVPVKVANH

TGCKCLPTAPRHPYSIIRR.

E. CCL21

Mature human CCL21 has the sequence of SEQ ID NO:5. The signal peptide: MAQSLALSLLILVLAFGIPRTQG (SEQ ID NO:16) may be removed and still have an active protein. Therefore, in some embodiments, the CCL21 polypeptide comprises: SDGGAQDCCLKYSQRKI-PAKVVRSYRKQEPSLGCSIPAILFLPRKRSQAEL-CADPKEL WVQQLMQHLDKTPSPQKPAQGC-RKDRGASKTGKKGKGSKGCKRTERSQTPKGP (SEQ ID NO:17). It is also contemplated that the active form includes the ECM-binding domain of CCL21, which is underlined in SEQ ID NO:5: MAQSLALSLLILVLAF-GIPRTQGSDGGAQDCCLKYSQRKIPAKVVRSYRK-QEPSLGCS IPAILFLPRKRSQAELCADPKELWVQQL-MQHLDKTPSPQKPAQGCrkdrgasktgkkgkgs KGCKRTERSQTPKGP. However, the lower case amino acid residues may be unimportant for CCL21 active and can be replaced with additional sequences such as a spacer, an additional ECM-binding domain, or any other functional or non-functional domain, or removed altogether.

Examples of CCL21 polypeptides are provided as SEQ ID NO: 18 and 19.

(SEQ ID NO: 18)
MAQSLALSLLILVLAFGIPRTQGSDGGAQDCCLKYSQRKIPAKVVRSYRK
QEPSLGCSIPAILFLPRKRSQAELCADPKELWVQQLMQHLDKTPSPQKPA
QGCRRRPKGRGKRRREKQRKGCKRTERSQTPKGP.

(SEQ ID NO: 19)
MAQSLALSLLILVLAFGIPRTQGSDGGAQDCCLKYSQRKIPAKVVRSYRK
QEPSLGCSIPAILFLPRKRSQAELCADPKELWVQQLMQHLDKTPSPQKPA
QGCRKDRGASKTGKKGKGSKGCKRTERSQTPKGPRRRPKGRGKRRREKQR
PTDAHL.

The mature mouse CCL21 sequence comprises SEQ ID NO:6 or SEQ ID NO: 20:

(SEQ ID NO: 20)
MAQMMTLSLLSLVLALCIPWTQGSDGGGQDCCLKYSQKKIPYSIVRGYRK
QEPSLGCPIPAILFLPRKHSKPELCANPEEGWVQNLMRRLDQPPAPGKQS
PGCRKNRGTSKSGKKGKGSKGCKRTEQTQPSRG.

VII. LIPIDS

In certain aspects, there may be provided methods and compositions for associating or encapsulating a lymphangiogenesis inducer, an antigen or both with a lipid and/or liposome. The lymphangiogenesis inducer, an antigen or both may be encapsulated in the aqueous interior of a liposome, interspersed within the lipid bilayer of a liposome, attached to a liposome via a linking molecule that is associated with both the liposome and the polynucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The liposome or liposome/lymphangiogenesis inducer, an antigen or both lymphangiogenesis inducer and antigen-associated compositions are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. An example is the lipid dioleoylphosphatidylcholine (DOPC).

"Liposome" is a generic term encompassing a variety of unilamellar, multilamellar, and multivesicular lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, certain embodiments also encompass compositions that have different structures in solution than the normal vesicular structure. For example, the lipids may assume a micellar structure or merely exist as non-uniform aggregates of lipid molecules. Also contemplated are lipofectamine-nucleic acid complexes.

In certain embodiments, the lipid may be associated with a hemaglutinating virus (HVJ). This has been shown to facilitate fusion with the cell membrane and promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1. In that such expression vectors have been successfully employed in transfer of a polynucleotide in vitro and in vivo, then they are applicable.

Exemplary lipids include, but are not limited to, dioleoylphosphatidylycholine ("DOPC"), egg phosphatidylcholine ("EPC"), dilauryloylphosphatidylcholine ("DLPC"), dimyristoylphosphatidylcholine ("DMPC"), dipalmitoylphosphatidylcholine ("DPPC"), di stearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dilauryloylphosphatidylglycerol ("DLPG"), dimyristoylphosphatidylglycerol ("DWG"), dipalmitoylphosphatidylglycerol ("DPPG"), di stearoylphosphatidylglycerol ("DSPG"), distearoyl sphingomyelin ("D SSP"), di stearoylphophatidylethanolamine ("DSPE"), dioleoylphosphatidylglycerol ("DOPG"), dimyristoyl phosphatidic acid ("DMPA"), dipalmitoyl phosphatidic acid ("DPPA"), dimyristoyl phosphatidylethanolamine ("DMPE"), dipalmitoyl phosphatidylethanolamine ("DPPE"), dimyristoyl phosphatidylserine ("DMPS"), dipalmitoyl phosphatidylserine ("DPPS"), brain phosphatidylserine ("BPS"), brain sphingomyelin ("BSP"), dipalmitoyl sphingomyelin ("DPSP"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), dioleoylphosphatidylethanolamine ("DOPE"), palmitoyloeoyl phosphatidylcholine ("POPC"), palmitoyloeoyl phosphatidylethanolamine ("POPE"), lysophosphatidylcholine, lysophosphatidylethanolamine, dilinoleoylphosphatidylcholine, phosphatidylcholines, phosphatidylglycerols, phosphatidylethanolamines, cholesterol.

Liposomes and lipid compositions can be made by different methods. For example, a nucleotide (e.g., siRNA) may be encapsulated in a neutral liposome using a method involving ethanol and calcium (Bailey and Sullivan, 2000). The size of the liposomes varies depending on the method of synthesis. A liposome suspended in an aqueous solution is generally in the shape of a spherical vesicle, and may have one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Lipids suitable for use can be obtained from commercial sources. For example, dimyristyl phosphatidylcholine ("DMPC") can be obtained from Sigma Chemical Co., dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform may be used as the only solvent since it is more readily evaporated than methanol.

Liposomes can be prepared in accordance with known laboratory techniques. In certain embodiments, liposomes are prepared by mixing liposomal lipids, in a solvent in a container (e.g., a glass, pear-shaped flask). The container may have a volume ten-times greater than the volume of the expected suspension of liposomes. Using a rotary evaporator, the solvent may be removed at approximately 40° C. under negative pressure. The solvent may be removed within about 5 minutes to 2 hours, depending on the desired volume of the liposomes. The composition can be dried further in a desiccator under vacuum. Dried lipids can be hydrated at approximately 25-50 mM phospholipid in sterile, pyrogen-free water by shaking until all the lipid film is resuspended. The aqueous liposomes can be separated into aliquots, each placed in a vial, lyophilized and sealed under vacuum.

Liposomes can also be prepared in accordance with other known laboratory procedures: the method of Bangham et al. (1965), the contents of which are incorporated herein by reference; the method of Gregoriadis (1979), the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

VIII. NUCLEIC ACID ASSAYS

Aspects of the methods include assaying nucleic acids to determine expression or activity levels. Arrays can be used to detect differences between two samples. Specifically contemplated applications include identifying and/or quantifying differences between RNA from a sample that is normal and from a sample that is not normal, between a cancerous condition and a non-cancerous condition, or between two differently treated samples. Also, RNA may be compared between a sample believed to be susceptible to a particular disease or condition and one believed to be not susceptible or resistant to that disease or condition. A sample that is not normal is one exhibiting phenotypic trait(s) of a disease or condition or one believed to be not normal with respect to that disease or condition. It may be compared to a cell that is normal with respect to that disease or condition. Phenotypic traits include symptoms of, or susceptibility to, a disease or condition of which a component is or may or may not be genetic or caused by a hyperproliferative or neoplastic cell or cells.

An array comprises a solid support with nucleic acid probes attached to the support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., 1991), each of which is incorporated by reference in its entirety for all purposes. Techniques for the synthesis of these arrays using mechanical synthesis methods are described in, e.g., U.S. Pat. No. 5,384,261, incorporated herein by reference in its entirety for all purposes. Although a planar array surface is used in certain aspects, the array may be fabricated on a surface of virtually any shape or even a multiplicity of surfaces. Arrays may be nucleic acids on beads, gels, polymeric surfaces, fibers such as fiber optics, glass or any other appropriate substrate, see U.S. Pat. Nos. 5,770,358, 5,789, 162, 5,708,153, 6,040,193 and 5,800,992, which are hereby incorporated in their entirety for all purposes.

In addition to the use of arrays and microarrays, it is contemplated that a number of difference assays could be employed to analyze nucleic acids, their activities, and their effects. Such assays include, but are not limited to, nucleic amplification, polymerase chain reaction, quantitative PCR, RT-PCR, in situ hybridization, Northern hybridization, hybridization protection assay (HPA)(GenProbe), branched DNA (bDNA) assay (Chiron), rolling circle amplification (RCA), single molecule hybridization detection (US Genomics), Invader assay (ThirdWave Technologies), and/or Bridge Litigation Assay (Genaco).

A further assay useful for quantifying and/or identifying nucleic acids is RNAseq. RNA-seq (RNA sequencing), also called whole transcriptome shotgun sequencing, uses next-generation sequencing (NGS) to reveal the presence and quantity of RNA in a biological sample at a given moment in time. RNA-Seq is used to analyze the continually changing cellular transcriptome. Specifically, RNA-Seq facilitates the ability to look at alternative gene spliced transcripts, post-transcriptional modifications, gene fusion, mutations/SNPs and changes in gene expression. In addition to mRNA transcripts, RNA-Seq can look at different populations of RNA to include total RNA, small RNA, such as miRNA, tRNA, and ribosomal profiling. RNA-Seq can also be used to determine exon/intron boundaries and verify or amend previously annotated 5' and 3' gene boundaries.

IX. PROTEIN ASSAYS

A variety of techniques can be employed to measure expression levels of polypeptides and proteins in a biological sample. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining protein expression levels of biomarkers.

In one embodiment, antibodies, or antibody fragments or derivatives, can be used in methods such as Western blots or immunofluorescence techniques to detect biomarker expression. In some embodiments, either the antibodies or proteins are immobilized on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present disclosure. The support can then be washed with suitable buffers followed by treatment with the detectably labeled antibody. The solid phase support can then be washed with the buffer a second time to remove unbound antibody. The amount of bound label on the solid support can then be detected by conventional means.

Immunohistochemistry methods are also suitable for detecting the expression levels of biomarkers. In some embodiments, antibodies or antisera, including polyclonal antisera, and monoclonal antibodies specific for each marker may be used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

Immunological methods for detecting and measuring complex formation as a measure of protein expression using either specific polyclonal or monoclonal antibodies are known in the art. Examples of such techniques include enzyme-linked immunosorbent assays (ELISAs), radioimmunoassays (RIAs), fluorescence-activated cell sorting (FACS) and antibody arrays. Such immunoassays typically involve the measurement of complex formation between the protein and its specific antibody. These assays and their quantitation against purified, labeled standards are well known in the art. A two-site, monoclonal-based immunoassay utilizing antibodies reactive to two non-interfering epitopes or a competitive binding assay may be employed.

Numerous labels are available and commonly known in the art. Radioisotope labels include, for example, $^{36}S$, $^{14}C$, $^{125}I$, $^{3}H$, and $^{131}I$. The antibody can be labeled with the radioisotope using the techniques known in the art. Fluorescent labels include, for example, labels such as rare earth chelates (europium chelates) or fluorescein and its derivatives, rhodamine and its derivatives, dansyl, Lissamine, phycoerythrin and Texas Red are available. The fluorescent labels can be conjugated to the antibody variant using the techniques known in the art. Fluorescence can be quantified using a fluorimeter. Various enzyme-substrate labels are available and U.S. Pat. Nos. 4,275,149, 4,318,980 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, .beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for Use in Enzyme Immunoassay, in Methods in Enzymology (Ed. J. Langone & H. Van Vunakis), Academic press, New York, 73: 147-166 (1981).

In some embodiments, a detection label is indirectly conjugated with an antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). In some embodiments, the antibody need not be labeled, and the presence thereof can be detected using a labeled antibody, which binds to the antibody.

X. SAMPLE PREPARATION

In certain aspects, methods involve obtaining a sample from a subject. The methods of obtaining provided herein may include methods of biopsy such as fine needle aspiration, core needle biopsy, vacuum assisted biopsy, incisional biopsy, excisional biopsy, punch biopsy, shave biopsy or skin biopsy. In certain embodiments the sample is obtained from a biopsy from colorectal tissue by any of the biopsy methods previously mentioned. In other embodiments the sample may be obtained from any of the tissues provided herein that include but are not limited to non-cancerous or cancerous tissue and non-cancerous or cancerous tissue from the serum, gall bladder, mucosal, skin, heart, lung, breast, pancreas, blood, liver, muscle, kidney, smooth muscle, bladder, colon, intestine, brain, prostate, esophagus, or thyroid tissue. Alternatively, the sample may be obtained from any other source including but not limited to blood, sweat, hair follicle, buccal tissue, tears, menses, feces, or saliva. In certain aspects the sample is obtained from cystic fluid or fluid derived from a tumor or neoplasm. In yet other embodiments the cyst, tumor or neoplasm is colorectal. In certain aspects of the current methods, any medical professional such as a doctor, nurse or medical technician may obtain a biological sample for testing. Yet further, the biological sample can be obtained without the assistance of a medical professional.

A sample may include but is not limited to, tissue, cells, or biological material from cells or derived from cells of a subject. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

The sample may be obtained by methods known in the art. In certain embodiments the samples are obtained by biopsy. In other embodiments the sample is obtained by swabbing, scraping, phlebotomy, or any other methods known in the art. In some cases, the sample may be obtained, stored, or transported using components of a kit of the present methods. In some cases, multiple samples, such as multiple colorectal samples may be obtained for diagnosis by the methods described herein. In other cases, multiple samples, such as one or more samples from one tissue type (for example colon) and one or more samples from another tissue (for example buccal) may be obtained for diagnosis by the methods. In some cases, multiple samples such as one or more samples from one tissue type (e.g. rectal) and one or more samples from another tissue (e.g. cecum) may be obtained at the same or different times. Samples may be obtained at different times are stored and/or analyzed by different methods. For example, a sample may be obtained and analyzed by routine staining methods or any other cytological analysis methods.

In some embodiments the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

In other cases, the sample is obtained by an invasive procedure including but not limited to: biopsy, needle aspiration, or phlebotomy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

General methods for obtaining biological samples are also known in the art. Publications such as Ramzy, Ibrahim Clinical Cytopathology and Aspiration Biopsy 2001, which is herein incorporated by reference in its entirety, describes general methods for biopsy and cytological methods. In one embodiment, the sample is a fine needle aspirate of a colorectal or a suspected colorectal tumor or neoplasm. In some cases, the fine needle aspirate sampling procedure may be guided by the use of an ultrasound, X-ray, or other imaging device.

In some embodiments of the present methods, the molecular profiling business may obtain the biological sample from a subject directly, from a medical professional, from a third party, or from a kit provided by a molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

In some embodiments of the methods described herein, a medical professional need not be involved in the initial diagnosis or sample acquisition. An individual may alternatively obtain a sample through the use of an over the counter (OTC) kit. An OTC kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately. A sample suitable for use by the molecular profiling business may be any material containing tissues, cells, nucleic acids, proteins, polypeptides, genes, gene fragments, expression products, gene expression products, protein expression products or fragments, or gene expression product fragments of an individual to be tested. Methods for determining sample suitability and/or adequacy are provided.

In some embodiments, the subject may be referred to a specialist such as an oncologist, surgeon, or endocrinologist. The specialist may likewise obtain a biological sample for testing or refer the individual to a testing center or laboratory for submission of the biological sample. In some cases the medical professional may refer the subject to a testing center or laboratory for submission of the biological sample. In other cases, the subject may provide the sample. In some cases, a molecular profiling business may obtain the sample.

XI. METHODS OF TREATMENT

As discussed above, the compositions and methods of using these compositions can treat a subject (e.g., prevent or treat a bacterial infection, a viral infection, a fungal infection, a protozoal infection, a helminth infection or a cancer condition or evoke a robust immune tolerance to an autoimmune disease) having, suspected of having, or at risk of developing an infection, cancer or an autoimmune disorder or related disease.

As used herein the phrase "immune response" or its equivalent "immunological response" refers to a humoral (antibody mediated), cellular (mediated by antigen-specific T cells or their secretion products) or both humoral and cellular response directed against a protein, peptide, or polypeptide of the embodiments in a recipient patient. Treatment or therapy can be an active immune response induced by administration of immunogen or a passive therapy effected by administration of antibody, antibody containing material, or primed T-cells.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include those methods described in Epitope Mapping Protocols (1996). T cells recognize continuous epitopes of about nine amino acids for CD8 cells or about 13-15 amino acids for CD4 cells. T cells that recognize the epitope can be identified by in vitro assays that measure antigen-dependent proliferation, as determined by 3H-thymidine incorporation by primed T cells in response to an epitope (Burke et al., 1994), by antigen-dependent killing (cytotoxic T lymphocyte assay, Tigges et al., 1996) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject. As used herein and in the claims, the terms "antibody" or "immunoglobulin" are used interchangeably.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

In some embodiments, a method includes treatment for a disease or condition caused by a bacterial infection, a viral infection, a fungal infection, a protozoal infection, a helminth infection or a cancer condition. Furthermore, in some examples, treatment comprises administration of other agents commonly used against a bacterial infection, a viral infection, a fungal infection, a protozoal infection, a helminth infection or a cancer condition.

In one embodiment a method includes treatment for a disease or condition caused by an autoimmune disorder. Furthermore, in some examples, treatment comprises administration of other agents commonly used against autoimmune disorders, such as one or more immunosuppressant compounds.

The therapeutic compositions are administered in a manner compatible with the dosage formulation, and in such amount as will be therapeutically effective. The quantity to be administered depends on the subject to be treated. Precise amounts of active ingredient required to be administered depend on the judgment of the practitioner. Suitable regimes for initial administration and boosters are also variable, but are typified by an initial administration followed by subsequent administrations.

Compositions of the current methods may be administered to patients via any route used to introduce vaccines or antibodies to patients. Such routes include, but are not limited to, mucosal or intramuscular delivery. In particular embodiments, a composition is administered to a patient intranasally or by inhalation. In other embodiments, a composition is administered intravenously or by intravenous injection. In additional embodiments, the administration of compositions includes, but is not limited to oral, parenteral, subcutaneous, intramuscular, intravenous administration, or various combinations thereof.

The manner of application may be varied widely. Any of the conventional methods for administration of a polypeptide therapeutic are applicable. These are believed to include oral application on a solid physiologically acceptable base or in a physiologically acceptable dispersion, parenterally, by injection and the like. The dosage of the composition will depend on the route of administration and will vary according to the size and health of the subject. In one treatment scheme, the patient receives a subcutaneous dose of the lymphangiogenesis inducer or inducers and antigens such as a bacterial antigen, a viral antigen, a fungal antigen, a protozoal antigen, a helminth antigen or a cancer antigen, together in a single formulation or composition or separately in multiple formulations or compositions, every week for three weeks and then every first week for an additional 1, 2, 3, 4, 5, 6, 7, 8, 9, 10, 11, or 12 months. In other aspects the patient or subject receives two injections spaced a minimum or 7 days apart within 1-2 months and then every week for an additional 1, 2, 3, 4, 5, 6, 7, 8, 9, 10, 11, or 12 months or every first week of the month for an additional 1, 2, 3, 4, 5, 6, 7, 8, 9, 10, 11, or 12 months.

In certain instances, it will be desirable to have multiple administrations of the composition, e.g., 2, 3, 4, 5, 6 or more administrations. The administrations can be at 1, 2, 3, 4, 5, 6, 7, 8, to 5, 6, 7, 8, 9, 10, 11, 12 twelve week intervals, including all ranges there between.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

The cancers amenable for treatment include, but are not limited to, tumors of all types, locations, sizes, and characteristics. The methods and compositions of the disclosure are suitable for treating, for example, pancreatic cancer, colon cancer, acute myeloid leukemia, adrenocortical carcinoma, AIDS-related cancers, AIDS-related lymphoma, anal cancer, appendix cancer, astrocytoma, childhood cerebellar or cerebral basal cell carcinoma, bile duct cancer, extrahepatic bladder cancer, bone cancer, osteosarcoma/malignant fibrous histiocytoma, brainstem glioma, brain tumor, cerebellar astrocytoma brain tumor, cerebral astrocytoma/malignant glioma brain tumor, ependymoma brain tumor, medulloblastoma brain tumor, supratentorial primitive neuroectodermal tumors brain tumor, visual pathway and hypothalamic glioma, breast cancer, lymphoid cancer, bronchial adenomas/carcinoids, tracheal cancer, Burkitt lymphoma, carcinoid tumor, childhood carcinoid tumor, gastrointestinal carcinoma of unknown primary, central nervous system lymphoma, primary cerebellar astrocytoma, childhood cerebral astrocytoma/malignant glioma, childhood cervical cancer, childhood cancers, chronic lymphocytic leukemia, chronic myelogenous leukemia, chronic myeloproliferative disorders, cutaneous T-cell lymphoma, desmoplastic small round cell tumor, endometrial cancer, ependymoma, esophageal cancer, Ewing's, childhood extragonadal Germ cell tumor, extrahepatic bile duct cancer, eye Cancer, intraocular melanoma eye Cancer, retinoblastoma, gallbladder cancer, gastric (stomach) cancer, gastrointestinal carcinoid tumor, gastrointestinal stromal tumor (GIST), germ cell tumor: extracranial, extragonadal, or ovarian, gestational trophoblastic tumor, glioma of the brain stem, glioma, childhood cerebral astrocytoma, childhood visual pathway and hypothalamic glioma, gastric carcinoid, hairy cell leukemia, head and neck cancer, heart cancer, hepatocellular (liver) cancer, Hodgkin lymphoma, hypopharyngeal cancer, hypothalamic and visual pathway glioma, childhood intraocular melanoma, islet cell carcinoma (endocrine pancreas), kaposi sarcoma, kidney cancer (renal cell cancer), laryngeal cancer, leukemia, acute lymphoblastic (also called acute lymphocytic leukemia) leukemia, acute myeloid (also called acute myelogenous leukemia) leukemia, chronic lymphocytic (also called chronic lymphocytic leukemia) leukemia, chronic myelogenous (also called chronic myeloid leukemia) leukemia, hairy cell lip and oral cavity cancer, liposarcoma, liver cancer (primary), non-small cell lung cancer, small cell lung cancer, lymphomas, AIDS-related lymphoma, Burkitt lymphoma, cutaneous T-cell lymphoma, Hodgkin lymphoma, Non-Hodgkin (an old classification of all lymphomas except Hodgkin's) lymphoma, primary central nervous system lymphoma, Waldenstrom macroglobulinemia, malignant fibrous histiocytoma of bone/osteosarcoma, childhood medulloblastoma, melanoma, intraocular (eye) melanoma, merkel cell carcinoma, adult malignant mesothelioma, childhood mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases, chronic myelogenous leukemia, adult acute myeloid leukemia, childhood acute myeloid leukemia, multiple myeloma, chronic myeloproliferative disorders, nasal cavity and paranasal sinus cancer, nasopharyngeal carcinoma, neuroblastoma, oral cancer, oropharyngeal cancer, osteosarcoma/malignant, fibrous histiocytoma of bone, ovarian cancer, ovarian epithelial cancer (surface epithelial-stromal tumor), ovarian germ cell tumor, ovarian low malignant potential tumor, pancreatic cancer, islet cell paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, childhood pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma, childhood Salivary gland cancer Sarcoma, Ewing family of tumors, Kaposi sarcoma, soft tissue sarcoma, uterine sezary syndrome sarcoma, skin cancer (nonmelanoma), skin cancer (melanoma), skin carcinoma, Merkel cell small cell lung cancer, small intestine cancer, soft tissue sarcoma, squamous cell carcinoma. squamous neck cancer with occult primary, metastatic stomach cancer, supratentorial primitive neuroectodermal tumor, childhood T-cell lymphoma, testicular cancer, throat cancer, thymoma, childhood thymoma, thymic carcinoma, thyroid cancer, urethral cancer, uterine cancer, endometrial uterine sarcoma, vaginal cancer, visual pathway and hypothalamic glioma, childhood vulvar cancer, and wilms tumor (kidney cancer).

A. Combination Therapy

The compositions and related methods, particularly administration of lymphangiogenesis inducer or inducers and antigens such as a bacterial antigen, a viral antigen, a fungal antigen, a protozoal antigen, a helminth antigen or a cancer antigen, may also be used in combination with the administration of antibacterial, antiviral, antifungal, antibiotic, antineoplastic or chemotherapeutic agent effective strategies or traditional immunomodulatory therapies. In specific aspects, administration of lymphangiogenesis inducer or inducers and antigens is provided in combination with programmed cell death protein-1 (PD-1) pathway inhibitors. In certain aspects, combination therapy may target PD-1 or the PD-L1 or PD-L2 ligands. Such strategies or therapies may be directed, among other aims, to modify the disease course, treat exacerbations, manage symptoms or improve a compromised function.

In one aspect, it is contemplated that a therapy is used in conjunction with immunosuppressants. In other aspects, a therapy is used in conjunction with disease-modifying agents, symptom controlling agents, or agents to improve compromised function. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the therapeutic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Various combinations of therapy may be employed, for example immunosuppressant therapy, disease-modifying agents, symptom controlling agents, or agents to improve compromised function is "A" and an antibody immunotherapeutic that comprises an antibody that binds a DC receptor and delivers an myelin sheath protein or component or a peptide or consensus peptide thereof is "B":

| | | | | |
|---|---|---|---|---|
| A/B/A | B/A/B | B/B/A | A/A/B | A/B/B |
| B/A/A | A/B/B/B | B/A/B/B | B/B/B/A | B/B/A/B |
| A/A/B/B | A/B/A/B | A/B/B/A | B/B/A/A | B/A/B/A |
| B/A/A/B | A/A/A/B | B/A/A/A | A/B/A/A | A/A/B/A |

Administration of the antibody compositions to a patient/subject will follow general protocols for the administration of such compounds, taking into account the toxicity, if any, of the composition. It is expected that the treatment cycles would be repeated as necessary. It is also contemplated that various standard therapies, such as hydration, may be applied in combination with the described therapy.

B. General Pharmaceutical Compositions

In some embodiments, pharmaceutical compositions are administered to a subject. Different aspects may involve administering an effective amount of a composition to a subject. In some embodiments, lymphangiogenesis inducers and antigens such as a bacterial antigen, a viral antigen, a fungal antigen, a protozoal antigen, a helminth antigen or a cancer antigen may be administered to the patient to protect against or treat a bacterial infection, a viral infection, a fungal infection, a protozoal infection, a helminth infection or a cancer condition. Alternatively, an expression vector encoding one or more such antibodies or polypeptides or peptides may be given to a patient as a preventative treatment. Additionally, such compositions can be administered in combination with an adjuvant or if immune tolerance is desired, an immunosuppressant. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-infective agents, immunosuppressants and immunotherapeutics, can also be incorporated into the compositions.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization or an equivalent procedure. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a immunotherapeutic composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

XII. KITS

Certain aspects of the present disclosure also concern kits containing compositions of the disclosure or compositions to implement methods of the disclosure. In some embodiments, kits can be used to evaluate one or more nucleic acid and/or polypeptide molecules. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1,000 or more nucleic acid probes, polypeptide detection agents (e.g. antibodies), synthetic RNA molecules or inhibitors, or any value or range and combination derivable therein. In some embodiments, there are kits for evaluating biomarker levels or activity in a cell.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

Kits for using probes, polypeptide detecting agents, and/or inhibitors or antagonists of the disclosure for prognostic or diagnostic applications are included. Specifically contemplated are any such molecules corresponding to any biomarker (e.g. CCL21 or VEGF-C) nucleic acid or polypeptide.

In certain aspects, negative and/or positive control agents are included in some kit embodiments. The control molecules can be used to verify transfection efficiency and/or control for transfection-induced changes in cells.

It is contemplated that any method or composition described herein can be implemented with respect to any other method or composition described herein and that different embodiments may be combined.

Any embodiment of the disclosure relating to a polypeptide or nucleic acid is contemplated also to cover embodiments whose sequences are at least 80, 81, 82, 83, 84, 85, 86, 87, 88, 89, 90, 91, 92, 93, 94, 95, 96, 97, 98, 99% identical to the polypeptide or nucleic acid.

Embodiments of the disclosure include kits for analysis of a pathological sample by assessing a nucleic acid or polypeptide profile for a sample comprising, in suitable container means, two or more RNA probes, or a biomarker polypeptide detecting agent, wherein the RNA probes or polypeptide detecting agent detects biomarker nucleic acids or polypeptides. In some embodiments, the reagents (i.e. RNA probe and/or polypeptide detecting agent) are labeled with a detectable label. Labels are known in the art and also described herein. The kit can further comprise reagents for labeling probes, nucleic acids, and/or detecting agents. The kit may also include labeling reagents, including at least one of amine-modified nucleotide, poly(A) polymerase, and poly(A) polymerase buffer. Labeling reagents can include an amine-reactive dye.

XIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Lymphatic Endothelial Cells Present Exogenous Antigens on MHC II

The inventors have observed that LECs can present exogenous antigens on MHC I and MHC II. This is surprising, in that antigen presentation on MHC II is usually associated with only so-called professional APCs, including DCs.

Experimental Design:

OT-II T cells are CD4 T cells that are transgenic for the T cell receptor (TCR) that recognizes an sequence in the model antigen ovalbumin, with the sequence ISQAVHAA-HAEINEAGR ($OVA_{323-339}$), on an I-A$^d$ immunological background. Primary DCs, LECs, and FRCs were compared for their baseline expression of MHC-II I-A, and for how this expression changes under inflammatory environments, by stimulating the cells in inflammatory cytokines such as TNFα and IFNγ. Then, OT-II cells were co-cultured with these cells in the presence of their antigen peptide $OVA_{323-339}$ and after 4 d of co-culture, the surface expression of activation markers was quantified on the OT-II cells by flow cytometry.

Methods:

Bone marrow-derived dendritic cells (BMDCs) were differentiated from bone marrow of healthy wild-type mice following an established method published by other groups (Lutz, et al., 1999). Mature DCs (mDCs) were obtained by incubating immature BMDCs with co-culture media supplemented with 10 nM $OVA_{323-339}$ peptide and 1 nM CpG-B for 6 h at 37° C., followed by three washes in PBS to remove all remnants of the CpG-B and antigen, followed by resuspension of the mDCs in co-culture media. To obtain primary LECs and FRCs, LNs from healthy wild-type mice were obtained and digested as above, then plated on tissue-culture polystyrene for 4 d with multiple washes to remove unbound cells. This process generally depletes all of the immune cell and blood cell compartment, and the remaining cells, which consist typically >99% of LECs and FRCs, were separated from each other using CD31$^+$ magnetic bead-based selection (Miltenyi Biotec). Cells were then stimulated in co-culture media supplemented with 100 ng/mL of IFNγ or TNFα for various timepoints, harvested from plates using Accutase, stained with antibodies against MHC-II I-A/I-E (clone AF6-88.5), CD44 (clone IM7), or CD62L (clone MEL14), and analyzed via flow cytometry on a BD LSR-II machine.

Results:

The inventors previously observed that LECs are able to acquire peptide-loaded MHC-II receptors from DCs through extracellular vesicles such as exosomes.[22] Here, the inventors demonstrate that the LECs express low levels of MHC-II under resting conditions (FIG. 1A), and can upregulate MHC-II within 24 h of stimulation with IFNγ (FIG. 1B). When OT-II cells are cultured in the presence of their cognate antigen and LECs, they are stimulated and acquire an antigen-experienced CD44$^+$ phenotype (FIG. 1C), but do not lose CD62L expression and proliferate much less than OT-II cells co-cultured with mature DCs.

The observation that LECs express MHC-II, albeit at much lower levels than DCs, is particularly relevant in light of the evidence that free peptides can directly load into the receptors and further, stimulate cognate CD4 T cells to express markers of antigen experience (FIG. 1). Similarly to what was observed with LEC-educated OT-I T cells (FIG. 2), LEC-educated OT-II cells do not lose CD62L expression, and therefore, appear to have a memory-like phenotype characterized by CD44$^+$CD62L$^+$ expression. However, OT-II cells as a whole were not as responsive to LEC education as OT-I cells, in the sense that a majority of LEC-educated OT-I cells proliferated and expressed activation markers as described earlier, while a majority of OT-II cells retained the naïve phenotype characterized by a CD44$^-$CD62L$^+$ profile. While this observation may explained by the low levels of MHC-II expression on LECs, it is nevertheless clear that LECs possess some ability to prime and activate CD4 T cell responses, albeit to much weaker extents than mDC-initiated CD4 responses.

Example 2: Lymphatic Endothelial Cells Educate T Cells to Induce Memory Responses that are Greater than Those Induced by Dendritic Cells Immunological priming refers to stimulation of lymphocytes by an APC so as to induce their activation and expansion. The inventors have observed that LECs can prime T cells so as to induce their differentiation in to memory T cells, even more so than can DCs, even though they induce a weaker effector expansion.

Experimental Design:

The inventors compared priming in vitro of OT I T cells on LECs exposed to ovalbumin, versus priming in vitro of OT-I T cells under the same conditions but on DCs exposed to ovalbumin. The behavior and biomarker profiles of the OT-I cells were assessed by flow cytometry after 3 days of co-culture. The OT-I cells were primed in vitro and then adoptively transferred into recipient C57BL/6 (which are also of the H2k$^b$ background) mice to follow immune responses. The memory phase response was measured at two time points in order to reflect early versus late memory responses. This was done using a *Listeria monocytogenes* challenge model, where the mice were challenged with ovalbumin-expressing *Listeria* strain, and the recall response to this challenge was measured. From the perspective of prophylactic vaccination, a stronger recall response to DC priming would indicate that DCs were more valuable than LECs in vaccination, and a stronger recall response to LEC priming would indicate that LECs were rather more valuable.

Methods:

Isolation of OT-I cells, LN-LECs, and LN-FRCs, and following co-cultures were performed as described under Example 1 above. OT-I cell proliferation was quantified by flow cytometry based on dilution of the CFSE dye as described above. In addition, the inventors introduced the proliferation index as a method of quantification of OT-I proliferation, which is calculated $$\sum_{i=0}^{g} \frac{n_i}{2^i},$$

where g is the total number of cell divisions observed (# of peaks in the CFSE histogram+1) and n, is the number of OT-I cells within a certain peak. This is essentially a measure of the number of observed OT-I cells normalized to the number of progenitor cells that led to that number of OT-I cells.

In order to evaluate the functional potential of LEC-educated CD8$^+$ T cells, the inventors sought to assess their functionality when they encounter a bacterial pathogen in vivo. Ex vivo generated (CD45.1.2) LEC-educated together with (CD45.1) DC-educated OT-I CD8$^+$ T cells were mixed at a ratio of 1:1 and adoptively transferred into C57/B16 mice (5×10$^4$ total cells/mouse). Mice that did not receive any T cells served as a positive control. The same mice were then challenged intravenously five weeks later with L.m.-OVA (10$^3$ cfu/mouse) to characterize early memory phase responses, or nine weeks later with 10$^4$ cfu/mouse to characterize long-term memory phase responses. L.m.-OVA for challenge was acquired from log phase of growth in BHI medium. Spleens were collected, homogenized and resuspended in sterile PBS. Different dilutions of the cell suspensions were generated, plated on BHI plates and incubated overnight at 37° C. The following day, bacterial load was determined by counting colony-forming units (cfu) present in the plates.

Results:

Following co-culture of OT-I cells with various APC subtypes in the presence of the cognate antigen, OT-I cells are activated and proliferate (FIGS. 2A-B). However, the resulting OT-I cells possess vastly different surface phenotypes, which suggest different functions (FIG. 2C-F). OT-I cells co-cultured with LECs and mDCs express high levels of CD25, some OX40, and similar levels of PD-1 and CTLA-4, which collectively suggest activation. However, they differ in the context of functional markers related to memory phenotype (FIG. 2D), LN homing (FIG. 2E), and tissue localization (FIG. 2F). Nevertheless, the LEC-educated OT-I cells are able to upregulate various activation markers (FIG. 3A) and produce effector cytokines (FIG. 3B) in the presence of additional co-stimulatory signals, even in spite of possessing a central memory-like phenotype (FIG. 3C).

Having demonstrated the capacity of LEC-educated CD8$^+$ T cells to give rise to functional effectors upon antigen re-encounter in vivo, the inventors sought to assess their contribution to immune responses against a real pathogen as well as evaluate their protective ability in direct competition to DC-educated T cells (FIG. 4). To this end, the inventors co-transferred ex vivo generated LEC-educated OT-I CD8$^+$ T cells together with DC-educated cells in mice at a 1:1 ratio. The mice were allowed to rest for five weeks and then challenged with *Listeria monocytogenes* (L.m.)-expressing OVA. LEC-educated cells exhibited effector function with cytotoxic potential, since they expressed cytokines (FIG. 4B, C) and underwent cytolytic granule release (FIG. 4B). More specifically, upon ex vivo restimulation, LEC-educated CD8$^+$ T cells displayed similar levels of IFNγ (FIG. 4B), as well as TNF-α and IL-2, with their DC-educated counterparts and they were on par in the expression of CD107, a marker of cytolytic granule exocytosis in the spleen. By assessing the percentage of single, double or triple positive cells for IFNγ, TNF-α and IL-2 (FIG. 4C) in order to evaluate the polyfunctionality of the cells, the inventors observed a similar distribution between the two populations. In LEC-educated cells, the inventors detected a dominant subset of cells positive for one of the three cytokines (42.18±5.35), a subset of cells positive for two of the three cytokines (30.37±6.25), a smaller subset of triple positive cells (2.85±0.60), while 25.11% (±6.75) of the cells did not produce any cytokine. Interestingly, there was a trend for a greater subset of double positive and triple positive (p=0.07) in LEC-educated cells compared to DC-educated ones.

The inventors observed that OT-I cells primed in vitro on DCs generally yielded a stronger effector immune response than did OT-I cells primed in vitro on LECs. By measures accepted in the art of vaccination, this would indicate that DCs are a more valuable APC than LECs. However, OT-I cells primed in vitro on LECs yielded an equivalent memory recall response after adoptive transfer than did OT-I cells primed on DCs in early memory phase induction, and further, appeared to provide better long term protection from bacterial challenge than did the OT-I cells primed on DCs (FIG. 4C,F). Given that the overall goal of prophylactic vaccination is to induce memory capable of strong memory recall, this indicates that LECs are a very valuable APC, thereby showing proof-of-concept of the value of targeting of antigen to LECs in vaccination. This is a departure from the state-of-the-art in vaccination, where the DC has been the most important target for antigen delivery.

Example 3: In Vivo Lymphangiogenesis May be Stimulated to Trigger Induction of Adaptive Immunity with Memory Experimental Design:

As an approach to target antigen to LECs in vaccination, the inventors have developed a hydrogel vaccine in which antigen is delivered in a gel along with bioactive factors that induce lymphangiogenesis. The rationale for this design is that antigen could be delivered to LECs that were induced to grow into the gel upon its injection. A powerful inducer of lymphangiogenesis is vascular endothelial growth factor-C (VEGF-C). A useful matrix as a gel is fibrin. Thus, a fibrin-binding variant of VEGF-C was incorporated into gel implants that also comprised the antigen. In addition, the inventors had also developed an alternative matrix based on poly(ethylene glycol), where the polymers were modified to contain the fibrin domains compatible with the fibrin-binding motifs present on the VEGF-C variant described above.

Hydrogels containing VEGF-C with or without the OVA model antigen were implanted into healthy wild-type mice, which had previously received CD4$^+$ T cells recognizing OVA (OT-II cells) with or without OT-I cells. Activity and biomarker expression on both cell types were evaluated early post-implantation of the vaccine (<10 d) or later during the early memory phase (22 d). Surface marker profiles on T cells can be typically used to characterize memory and effector phenotypes.

Methods: Hydrogel synthesis, preparation, and implantation. 8-arm, 40 kDa poly(ethylene glycol) (PEG)-maleimide was reacted with 9.6× molar excess of either Ac-FKGGVPMSMRGGERCG-Amide or NQEQVSPLERCG-Amide peptides in dimethylformamide, in the presence of 10× molar excess of triethylamine. The reaction was allowed to proceed for at least 4 h at 37° C. with agitation, after which the completed polymer-peptide conjugates (hereinafter referred to as 8APEG-FKGG &

8APEG-NQEQVSPL) were isolated using a size-exclusion chromatography and characterized by NMR and BCA assay to confirm peptide conjugation. 5% wt hydrogels were prepared by mixing 1 mg of 8APEG-FKGG & 1 mg of 8APEG-NQEQVSPL with desired bioactive factors (VEGF-C and/or OVA), 0.2 U Factor XIII, and 0.075 U thrombin, adjusted to a final volume of 40 µL in TBS with 50 mM $CaCl_2$. This mixture was pipetted to mix and injected into the interscapular region of isoflurane-anesthetized, healthy wild-type mice intradermally, where it polymerizes within 10-15 min of injection. Each mice received a single hydrogel.

Fibrin-Binding Protein Variants.

The fibrin-binding domain use to modify the proteins allows the binding into the hydrogels described in this example, since they are crosslinked with the fibrin-cross-linking transglutaminase Factor XIII. Cloning of TgVEGFC: a matrix metalloproteinase (MMP)-cleavage site followed by the fibrin-binding domain (Tg) was added at the C-terminus of the mouse VEGFC sequence (accession NM_009506.2, mature peptide, amino acid 108-223) by sequential polymerase chain reactions. Similarly, a poly-His tag followed by a thrombin-cleavage site was added at the N-terminus of VEGFC (TgVEGFC final design: "polyHis-thrombin-VEGFC-MMP-Tg"). The resulting sequence of TgVEGFC was then inserted in pSeqTagA plasmid backbone. Cloning of TgOVA: a MMP-cleavage site followed by the fibrin-binding domain (Tg) was added at the C-terminus of the chicken ovalbumin (OVA) sequence (accession P01012, full length), and a poly-His tag followed by a thrombin-cleavage site was added at the N-terminus of OVA, by sequential polymerase chain reactions (TgOVA final design: "polyHis-thrombin-OVA-MMP-Tg"). The resulting sequence of TgOVA was inserted into pSeqTagA plasmid backbone. Production of proteins: both TgVEGFC and TgOVA have been produced as follows. The plasmid was transfected into HEK-293E using 25 kDa polyethyleinimine as a transfection agent and cells and cultured in FreeStyle medium (Invitrogen, Carlsbad, USA) supplemented with glutamine (4 mM) and valproic acid (3.75 mM). At 7 days post-transfection, the expressed protein was isolated from the cell culture supernatants using $Ni^{2+}$-affinity chromatography (for the poly-His tag). The poly-His tag was then cleaved with a commercial agarose bead-bound thrombin cleavage kit (Sigma-Aldrich, St. Louis, USA), and purified using size-exclusion chromatography. The purified proteins were further dialyzed against Tris-buffer saline, sterilized through 0.22 µm filtration and stored at −80° C.

Intravital Imaging and Analysis.

All mice were anesthetized via 4.0% isoflurane and imaged via a Xenogen IVIS Spectrum (Caliper Life-Sciences/Perkin-Elmer, Waltham, Mass., United States). AlexaFluor750-tagged VEGF-C was detected via excitation and emission filters set at 745/800 nm and exposure time at 0.5 seconds. To quantify protein release from the hydrogels, ROIs were defined for each gel injection site using images obtained at the time of gel implantation. For any given gel injection site, the same ROIs were kept for the duration of the experiment. Background-corrected total photon counts within ROIs were quantified using Perkin-Elmer Living Image software (version 4.0) and normalized against total photon counts within the ROI at the time of injection in order to obtain release profiles of the fluorescently-labeled proteins over time.

Mice and adoptive transfers. OT-I and OT-II cells were isolated from spleens of healthy, adult OT-I and OT-II mice using commercial kits for CD8 and CD4 negative selection, respectively, according to manufacturer's instructions (Stemcell Technologies, Vancouver, Canada). Purity was confirmed to be 90-98% by flow cytometry, at which point cells were resuspended at $5\times10^6$ cells/mL in serum-free RPMI-1640 media. 200 µL of this suspension (corresponding to $1\times10^6$ cells) was injected into recipient wild-type C57Bl/6 mice (gender-matched, 8-12 weeks old) via the tail-vein one day prior to hydrogel implantation.

Vaccinations and Infection-Mimicking Challenge.

As a positive control vaccine, healthy adult wild-type mice were injected with 50 µg OVA and 50 µg CpG, in 50 µL PBS, intradermally via the front footpads (254, per footpad). This was repeated 15 days after the first vaccination in order to boost the T cell responses in these mice. For the challenge model, previously-vaccinated mice, or mice receiving hydrogels (with no vaccination boost) were injected in the front footpads with 50 µg OVA and 10 µg LPS in 50 µL PBS (25 µL per footpad). All mice were sacrificed 3 d post-challenge.

Results:

Fibrin-mimic PEG hydrogels are prepared liquid, injected into a mouse intradermally, and polymerize within 10-15 min of injection in vivo (FIG. 5A). Since there is the possibility of including fibrin-binding variants of proteins of interest into the hydrogel system, which leads to its slow release over time, this can be leveraged to create a flexible vaccine delivery platform which encompasses antigens of interest, chemoattractants and cytokines for recruitment and modulation of immune responses, as well as growth factors for encouraging ingrowth of local cell types, all in a system that slowly releases these proteins over time (FIGS. 5B-C).

As an example, the inventors showed here the delivery of soluble VEGFC (sVEGFC) versus a fibrin-binding variant (TgVEGFC) from the hydrogel system (FIGS. 5B-C), where the TgVEGFC is retained at the implant sites for about 50% longer than the sVEGFC. sVEGFC levels dropped to 10% of administered amounts within 8 d post-implantation, while TgVEGFC levels took 4 more days to reach this level. This led to different effects, as the TgVEGFC, owing to its longer retention locally, enhanced lymphangiogenesis at the implant site (FIGS. 5D-E), while the sVEGFC enhanced lymphangiogenesis mainly at the dLNs (FIGS. 5F-G). These were determined based on increased LYVE-1+ staining in the respective treatment groups detected by microscopy (FIGS. 5D,F) and quantification of local LEC populations by flow cytometry based on $gp38^+CD31^+$ staining (FIGS. 5E,G).

Focusing on the TgVEGFC-delivering formulation, the inventors observed increased recruitment of immune cells, defined by $CD45^+$ staining, within 9 d post-implantation into the mice (FIG. 6A). However, at 22 d post-implantation, TgVEGFC gels further enhance this difference (FIG. 6B), and this appears to be in large part due to increased recruitment of T cells (FIGS. 6C-D) and myeloid cells that are $CD11c^-CD11b^+$ (FIG. 6D). Quantification of the numbers and composition of the T cells and the dendritic cell compartments (FIGS. 6E-G) reveal a 6-fold increase in accumulation of CD4 T cells at the implant site, while CD8 T cells and DCs experienced modest levels of accumulation, if any at all.

To investigate if the increased recruitment of CD4 T cells can be leveraged towards the development of a vaccine, OVA and VEGFC were co-delivered via the hydrogels, and within 8 d post-implantation, implant sites were isolated for analysis of the phenotype of the CD4 T cells (FIG. 7). At this early timepoint, there are typically no significant differences in CD4 T cell accumulation at the implant site (FIG. 6E), so any differences in accumulation of any specific CD4 T cell subtypes may better reflect differences in T cell education. Hydrogels delivering both TgVEGFC and TgOVA created a local environment such that more cells isolated from the implant site spontaneously secreted IFNγ, and these differences were preserved when the same cells were stimulated with OVA (FIG. 7B). Furthermore, these cells contained a larger portion of effector-memory cells expressing a $CD44^+CD62L^-KLRG1^-CD127^+$ marker profile regardless of whether they were transferred OT-II cells or the endogenous CD4 T cells. In contrast, there was no detected increase in short-lived effector cells (SLECs).

Since these results suggest that hydrogels delivering TgVEGFC+TgOVA promoted faster generation of effector-memory CD4 T cells locally, the inventors hypothesized this may lead to higher numbers of circulating effector-memory CD4 T cells, reflecting the possibility that this may be used as a platform for vaccination. The inventors administered OT-I and OT-II cells into recipient mice 1 d prior to administration of the hydrogels (FIG. 8A), and at various time points, blood samples were obtained for flow cytometry analysis. Mice were sacrificed at 22 d post-implantation, and implant sites and the draining LNs—brachial LNs (bLNs) were also collected for flow cytometry analysis (FIG. 8B). As expected, relative to negative control hydrogels which lacked TgOVA, hydrogels delivering TgVEGFC+TgOVA enhanced the proportion of OT-I and OT-II cells expressing the $CD44^+CD62L^-$ profile (within which the effector-memory T cells are found) in all organs analyzed. Notably, this was also observed for the endogenous CD4 T cells found at the implant site for both hydrogels delivering TgVEGFC. With regards to the CD8 T cells, both TgOVA-containing hydrogel conditions produced similar effects in terms of the distribution of OT-I and endogenous T cells into the various subpopulations defined by CD44 and CD62L.

Finally, the performance of the hydrogels delivering TgVEGFC+TgOVA as a vaccine were compared head-to-head against a standard vaccine, consisting of soluble antigen and an adjuvant, injected intradermally in the front limbs of mice (FIG. 9A). To analyze for the immediate response to vaccination, a cohort of mice was sacrificed 3 days following hydrogel implantation or the initial vaccine. Another cohort was incubated for 35 days (mice in the standard vaccine group were boosted at d15), then challenged with the antigen and LPS to mimic an infection, incubated for another 3 days, then sacrificed. Hydrogel implantation sites, draining LNs, and blood were collected for proteomics analysis via ELISAs and Luminex. As expected, the standard vaccine elicited a moderate level of systemic inflammation (FIG. 9B), as characterized by elevated serum levels of the inflammatory mediators CXCL1, CXCL10, IL-10, M-CSF, BAFF, and IL-5 relative to all other groups tested. Following antigenic challenge, there was no difference in the circulating levels of all of these signals. Notably, the hydrogels delivering TgVEGFC+TgOVA produced highly localized responses (FIG. 9C), and the antigen challenge resulted in much higher local levels of the cytokines IL-15, CXCL1, and CCL20 within this group relative to all other groups. These are particularly important in that they stimulate T cell proliferation and memory T cells (IL-15), while recruiting more activated T cells and APCs (CCL20) and other immune cells (CXCL1).

Inducing local lymphangiogenesis increases the local accumulation of various immune cell subtypes, particularly CD4 T cells and myeloid cells (the inventors have not further investigated which subtypes were recruited). Co-delivery of an antigen with the lymphangiogenic mediators promotes local education of the T cells, promoting the generation of effector-memory CD4 T cells and as they disseminate into the bloodstream, they are able to circulate and potentially provide protection from antigenic challenges elsewhere in the body. It is also notable that endogenously-derived CD4 T cells also acquired activated phenotypes at the implant site. Since all hydrogel materials were confirmed endotoxin-free prior to injection, this activation may be potentially due to recognition of other OVA-derived antigens, resulting in the generation of CD4-directed adaptive responses against multiple epitopes derived from the same antigen. With CD4 T cells being capable of aiding in both B cell-mediated as well as CD8 T cell-mediated immune responses, this generation of CD4 memory, through a combination of lymphangiogenesis and antigen delivery, represents a vaccination strategy applicable to a large array of antigens. Moreover, the hydrogel vaccines were able to induce these memory responses without producing systemic inflammation that is seen with a standard vaccination strategy. At the site of the hydrogel implantation, the hydrogel 'vaccines' were even superior to the control vaccine at inducing cytokines and chemokines related to T cell memory and effector formation as well as recruitment of accessory immune cells.

Example 4: Lymphangiogenic Growth Factors May be Engineered to Induce In Vivo Lymphangiogenesis Experimental design: For the induction of in vivo lymphangiogenesis, it is important to provide the means to through which lymphangiogenic factors such as VEGFC may be retained in a tissue site. This can be done by incorporating the VEGFC into an injectable matrix (either co-delivered with the VEGFC, or in a separate formulation), or by providing the means for the VEGFC to directly bind the tissues in the injection site (which in this case, may also function as a matrix). The former is illustrated in Example 4 in the form of a polymeric hydrogel, which is crosslinked under the action of the naturally-occurring coagulation transglutaminase Factor XIIIa. Fibrin serves as another such material, which may first be crosslinked physically after exposure to thrombin, and then further crosslinked covalently under the action of Factor XIIIa. Thus, one means through which VEGFC may be rendered compatible for retention into such matrices is achieved by engineering them with a domain that serves as a Factor XIIIa substrate. The inventors have shown that the N-terminal domain of the protein alpha2-plasmin inhibitor (the amino acids NQEQVSPL) serves as such a substrate and can be fused to a terminus of proteins[27] such as VEGFC, to form TgVEGFC fusion protein. Factor XIIIa may therefore act on this fusion protein, and use the engineered peptide tag to directly graft the bioactive factor onto the polymeric or fibrin matrix. As an alternative, the inventors have shown that matrix-binding domains from proteins may be identified and fused to the bioactive factor, which allows binding to both matrices such as fibrin but also naturally-occurring, endogenous matrices such as the extracellular matrix (Martino, et al., 2014). Specifically, the inventors have shown that a domain in placental growth factor-2 ($PlGF-2_{123-144}$) is such a binding domain, and thus this domain can be used to engineer a matrix-binding variant of VEGFC, $PlGF-2_{123-144}$-VEGFC.

Methods: TgVEGFC is prepared as described in Example 4. The sequence of $PlGF-2_{123-144}$-VEGFC was made by adding the matrix-binding domain $PlGF-2_{123-144}$ to the C-terminus of the mouse VEGFC sequence (accession NM_009506.2, mature peptide, amino acid 108-223). In addition, a polyHis tag followed by a Factor Xa-cleavage site was added at the N-terminus of the VEGFC sequence. The resulting sequence was inserted in pXLG plasmid backbone and expressed in HEK293-E cells under the same conditions as for TgVEGFC (described in Example 4). The expressed protein was purified from the cell supernatant after 7 days in culture using $Ni^{2+}$-affinity chromatography and size exclusion chromatography. The purified proteins were sterile-filtered and stored in Tris-buffered saline at −80° C.

Results: TgVEGFC was covalently incorporated into fibrin and fibrin-mimetic matrices during polymerization by FactorXIIIa-mediated crosslinking (FIG. 5A-C). $PlGF-2_{123-144}$-VEGFC may be non-covalently sequestered into fibrin or endogenous matrices, owing to the high affinity of the $PlGF-2_{123-144}$ for endogenous extracellular matrix components. The spatial sequestration and slow controlled release of bioactive TgVEGFC and $PlGF-2_{123-144}$-VEGFC variants into the delivery site are likely to sequester the lymphangiogenic effects of VEGFC (eg. LECs signaling, proliferation, migration and lymphatic vessels formation) to the injection site, minimizing the systemic side effects (FIGS. 5D-E).

By using protein engineering approaches, lymphangiogenic factors can be generated that are more potent in inducing local lymphangiogenesis in vivo than their wild-type counterparts. The inventors illustrate that matrix binding is one such approach by which to achieve this, for example by binding covalently to matrix under the influence of a transglutaminase (with Factor XIIIa, although other transglutaminases such as tissue transglutaminase would be useful) and non-covalently, for example by binding with high affinity to the extracellular matrix or extracellular matrix analogs (Martino, et al., 2013).

Example 5: Tumor Lymphangiogenesis Promotes T Cell Infiltration and Potentiates Immunotherapy in Melanoma In melanoma, VEGF-C expression and consequent lymphangiogenesis correlate with metastasis and poor prognosis. VEGF-C also promotes tumor immune suppression, suggesting that lymphangiogenesis inhibitors may be clinically useful in combination with immunotherapy. The inventors addressed this hypothesis in mouse melanomas, with VEGFR-3 blocking antibodies and found, unexpectedly, that VEGF-C signaling enhanced therapeutic response to various immunotherapies. This was mediated by VEGF-C-induced CCL21 and infiltration of naïve T cells into the tumor before immunotherapy, since CCR7 blockade reversed the potentiating effects of VEGF-C. In human metastatic melanoma, gene expression of VEGF-C strongly correlated with CCL21 and T cell inflammation, while serum VEGF-C levels associated with T cell activation and expansion following peptide vaccination. It is proposed that tumor VEGF-C potentiates immunotherapy by attracting naïve T cells, which are locally activated upon immunotherapy-induced tumor cell killing to augment the antitumor immune response. In this way, VEGF-C may serve as a predictive biomarker for immunotherapy response.

It these experiments, it was sought to determine whether inhibiting tumor-associated lymphangiogenesis, and thus reducing its suppressive effects, would enhance the efficacy of immunotherapy, but find, surprisingly, that it increases resistance to immunotherapy. Instead, the inventors have identified a new mechanism whereby CCL21-dependent recruitment of naïve T cells into lymphangiogenic melanomas renders the tumor microenvironment more responsive to systemic immunotherapy. It is hypothesized that, once in the tumor, naïve T cells are locally primed and activated following immunotherapy-induced tumor cell death, leading to epitope spreading and long lasting anti-tumor immunity. These results reveal a new role to tumor-associated lymphangiogenesis in shaping the tumor immune microenvironment. While VEGF-C inhibits immunotherapy approaches that rely on activation within the immunosuppressed tumor draining lymph node, it induces a characteristic immune signature in the primary tumor that potentiates systemic immunotherapy.

A. VEGFR-3 Inhibition Decreases Suppressive Features of VEGFC-Expressing B16 Melanoma We first assessed whether anti-VEGFR-3 ($\alpha$R3) antibody treatment specifically altered peri- and intratumoral LEC density in B16-F10 tumors modified to express ovalbumin (B16-OVA) or OVA and VEGF-C (B16-OVA/VC). Intratumoral VEGF-C expression was confirmed in B16-OVA/VC tumors (FIG. 17A). Interestingly, blocking VEGFR-3 signaling in B16-OVA/VC tumors lead to increased VEGF-C levels, possibly due to accumulation consequential to decreased receptor-ligand internalization. As expected, VEGF-C expression increased the density of intratumoral Lyve-1$^+$ lymphatic vessels, while $\alpha$R3-treated tumors and non-VEGF-C expressing B16-OVA tumors were devoid of them (FIG. 17A and FIG. 17B). This was confirmed by flow cytometry, revealing that LECs (gp38$^+$CD31$^+$), but not blood endothelial cells (BECs, gp38$^-$CD31$^+$) or macrophages (F4/80), were enriched in lymphangiogenic tumors (FIGS. 10B and 17C-D). Primary tumor growth of $\alpha$R3-treated B16-OVA tumors was unaffected, while B16-OVA/VC tumors reacted with slightly delayed tumor growth to $\alpha$R3 treatment, which however did not significantly affect overall survival (FIG. 10C).

In line with previous reports, we found a VEGFR-3-dependent trend towards increased CD45$^+$ immune cell density in B16-OVA/VC tumors (FIG. 10D) including a significant increase of CD4$^+$FoxP3$^+$ regulatory T cells (FIG. 10E). Antigen-presenting cells (APCs) including conventional dendritic cells (DCs), cross-presenting CD8$^+$ DCs, myeloid DCs, and also potentially immunosuppressive myeloid-derived suppressor cells (MDSCs) were generally less abundant in the $\alpha$R3—as compared to control IgG-treated B16-OVA/VC tumors (FIGS. 10F-G and FIGS. 17E-F). We did not detect any significant effect of anti-VEGFR-3 therapy on the immune cell microenvironment in non-VEGF-C over-expressing B16-OVA tumors (FIGS. 10D-G and FIGS. 17D-F). Taken together, these data demonstrate that VEGF-C expression promotes an immune suppressive tumor microenvironment, while inhibiting VEGFR-3 prevents VEGF-C-driven tumor lymphangiogenesis and decreases suppression in B16 melanomas.

B. Lymphangiogenic Melanomas are Highly Sensitive to Immunotherapy

Having confirmed that VEGFR-3 blockade decreases cellular hallmarks of immuno suppression in B16-OVA/VC tumors, we hypothesized that a less suppressed environment in $\alpha$R3-treated tumors would enhance the efficacy of anti-tumor immunotherapy. To test this, we adoptively transferred ex vivo activated OVA-specific CD8$^+$ OT-I cells into tumor-bearing mice and assessed tumor growth over time. In line with our previous findings, non-lymphangiogenic B16 tumors were more sensitive to adoptive T cell therapy (ATT) in the short-term, leading to a significantly decreased tumor volume on day 12 (FIG. 11A). Against our expectation, $\alpha$R3-treated B16-OVA/VC tumors started progressing shortly after peak regression on day 16, while control IgG-treated B16-OVA/VC tumors showed a profound and long lasting response to ATT. This translated into significantly decreased tumor volume in the progression phase and into increased survival of control IgG-treated B16-OVA/VC tumor-bearing mice. When we performed the same experiment in mice that lack dermal lymphatic vessels (K14-VEGFR-3-IgG mice) there was no difference between B16-OVA and B16-OVA/VC tumor growth or host survival (FIG. 11B), confirming that the therapeutic benefit of ATT in B16-OVA/VC tumors was dependent on host lymphangiogenesis.

We next asked whether the lymphangiogenic status of B16 melanomas modulates the efficacy towards an immunotherapy approach that relies on raising an endogenous anti-tumor response. We thus treated tumor-bearing mice with a therapeutic DC vaccination (DC vax). DCs were activated ex vivo with LPS and then pulsed with the immunodominant MHC-I peptide SIINFEKL ex vivo, before being injected intraperitoneally into mice on days 4 and 10 after tumor inoculation. As with ATT, lymphangiogenic tumors grew significantly larger immediately after the DC vax, but then underwent profound regression (FIG. 11C). Accordingly, the median survival increased from 21 days for αR3-treated to over 2 months for control IgG-treated B16-OVA/VC tumor-bearing mice.

We next asked whether the lymphangiogenic status of B16 tumors also modulates non-antigen-specific immunotherapy using an adjuvant-only treatment with the Toll-like receptor 9 (TLR9) ligand CpG. Indeed, CpG treatment was more effective at controlling tumor growth and enhancing survival in lymphangiogenic (control IgG-treated) tumors compared to those treated with VEGFR-3 blocking antibodies (FIG. 11D). When CpG was combined with OVA protein, vaccine efficacy was almost complete (FIG. 11E)—with the exception of one mouse, tumors regressed completely, even after several months.

Importantly, the vaccine-potentiating effects of VEGF-C were not limited to the more immunogenic protein OVA, since an effective vaccine composed of nanoparticle-bound endogenous melanoma peptide Trp2 (NP-Trp2) and CpG adjuvant showed similar trends (FIG. 11F). We performed similar experiments in mice inoculated with wildtype B16 (B16 WT) and VEGF-C overexpressing (B16-VC) tumors lacking OVA expression to rule out the possibility that the observed effects were dependent on the expression of a foreign antigen. VEGFR-3 blocking had no profound effect on B16 WT or B16-VC tumors (FIG. 18A). However, as for the OVA expressing tumors, CpG adjuvant therapy alone induced delayed tumor growth and enhanced survival (FIG. 18B), and the NP-Trp2+CpG vaccine induced tumor regression and long-lasting responses in lymphangiogenic mice (FIG. 18C).

To ensure that our observations were not specific to the B16 melanoma model, we performed an immunotherapy trial in a more clinically relevant, genetically engineered mouse (GEM) model of melanoma driven by mutated $BRAF^{V600E}$ (further referred to as BRAF GEM). In order to raise a potent anti-tumor immune response, BRAF GEM mice received a combinatorial immunotherapy consisting of a peptide vaccine (CpG+gp100-peptide) combined with anti-PD-1 blockade starting 8 days after enrollment into the trial. Indeed, as observed in the B16 model, αR3-treated BRAF GEM mice responded less well to immunotherapy intervention, while IgG-treated mice showed delayed tumor outgrowth and increased survival (FIG. 11G).

Altogether, these data demonstrate that VEGF-C signaling in melanoma potentiates the effects of immunotherapy, particularly with protein or peptide vaccines, despite promoting a more immune suppressive microenvironment.

C. CCL21 is Increased in Lymphangiogenic Melanomas and Drives Recruitment of Naïve T Cells into VEGF-C Overexpressing B16 Tumors We next asked why the more immunosuppressed, invasive tumors would be more responsive to immunotherapy. When examining the immune cell infiltrates, we found a significant increase (~2.5 fold) in CD4$^+$FoxP3$^-$ T cell density as well as increased CD8$^+$ T cell density in control IgG-treated 1B16-OVC/VC tumors as compared to those with VEGFR-3 blocking (FIG. 12A). Interestingly, a large fraction of infiltrating CD4$^+$ TILs had a naïve (CD62L$^+$CD44$^-$) phenotype (FIG. 12B), shifting the balance between naïve and effector (CD62L$^-$CD44$^+$) CD4$^+$ T cells in favor of naïve ones in control IgG-treated B16-OVC/VC tumors (FIG. 12C).

Since naïve, but not effector, T cells express the chemokine receptor CCR7, we assessed tumor expression of the CCR7 ligand CCL21, which is normally expressed by LN stromal cells to guide naïve and memory T cells as well as mature DCs into the LN parenchyma. CCL21, when expressed at physiological levels (i.e., as in the LN), has been shown to promote local immune suppression by changing the tumor stroma. Because CCL21 is expressed by LECs and upregulated in response to VEGF-C/VEGFR-3 signaling, we were not surprised to find that CCL21 protein was substantially increased in control IgG-treated B16-OVA/VC as compared to either control IgG-treated B16-OVA or αR3-treated B16-OVA/VC tumors (FIG. 12D). Intratumoral LECs could indeed be a major source of CCL21, as the chemokine could be mainly detected in close proximity to lymphatic endothelium but not elsewhere in the tumor microenvironment (FIG. 12E). This effect was both restricted to CCL21 within the local tumor microenvironment, as no change in CCL21 levels could be detected in the tumor draining or non-draining LNs (FIG. 12D) and as no change in other cytokines levels could be detected within the tumor (FIG. 19A). Accordingly, and increased number of CCR7 expressing conventional CD4$^+$ and CD8$^+$ T cells was present within B16-OVA/VC as compared to B16-OVA tumors (FIG. 12F).

Even though BRAF GEM tumors expressed much lower, possibly more physiologic, levels of VEGF-C (FIG. 19B) as compared to VEGF-C overexpressing B16 tumors (FIG. 17A), we observed VEGFR-3 dependent tumor-associated lymphangiogenesis (FIG. 19C) and CCL21 expression (FIG. 19D). As in lymphangiogenic tumors, CCL21 accumulations within BRAF GEM tumors were mainly localized around the lymphatic endothelium (FIG. 17E).

To test whether CCL21/CCR7 signaling was indeed a mechanism underlying increased recruitment of naïve T cells into lymphangiogenic tumors, B16-OVA/VC tumor-bearing mice were treated with CCR7 blocking antibodies (FIG. 12G-E). Anti-CCR7 (aCCR7) treatment mainly reduced the infiltration of naïve T cells (FIG. 12G-H), with a very large reduction in the ratio of naïve versus effector phenotype for both tumor-infiltrating CD4$^+$ and CD8$^+$ T cells (FIG. 12I). We could also show this more directly by adoptive transfer of allogeneic (CD45.2) naïve OT-I cells into mice bearing B16-OVA/VC tumors and examining their TILs; after 24 hours, nearly 10-fold fewer OT-I cells were found in αCCR7-treated tumors compared with controls (FIG. 12J). Altogether, these data demonstrate that the CCL21/CCR7 axis not only drives regulatory CD4+ but also naïve T cells into lymphangiogenic B16 melanomas.

D. VEGF-C Correlates with the Expression of CCL21, CCR7, and a T Cell Signature in Human Melanoma Samples We next asked whether the VEGF-C/CCL21 axis was relevant for shaping the immune microenvironment in human melanoma. We first performed immunofluorescence analysis of the lymphatic marker podoplanin in tissue sections of 14 primary human melanomas (FIG. 13A-B). In roughly half of the tumors, we found substantially higher lymphatic density in the tumor than in the adjacent skin, implying that these were lymphangiogenic (FIG. 13B). Furthermore, we stained sections of human primary melanoma for VEGF-C, LECs (podoplanin+) and CCL21, and found ubiquitous VEGF-C expression (FIG. 13C) as well as more restricted CCL21 expression by intratumoral LECs (FIG. 13D).

Figure 20:
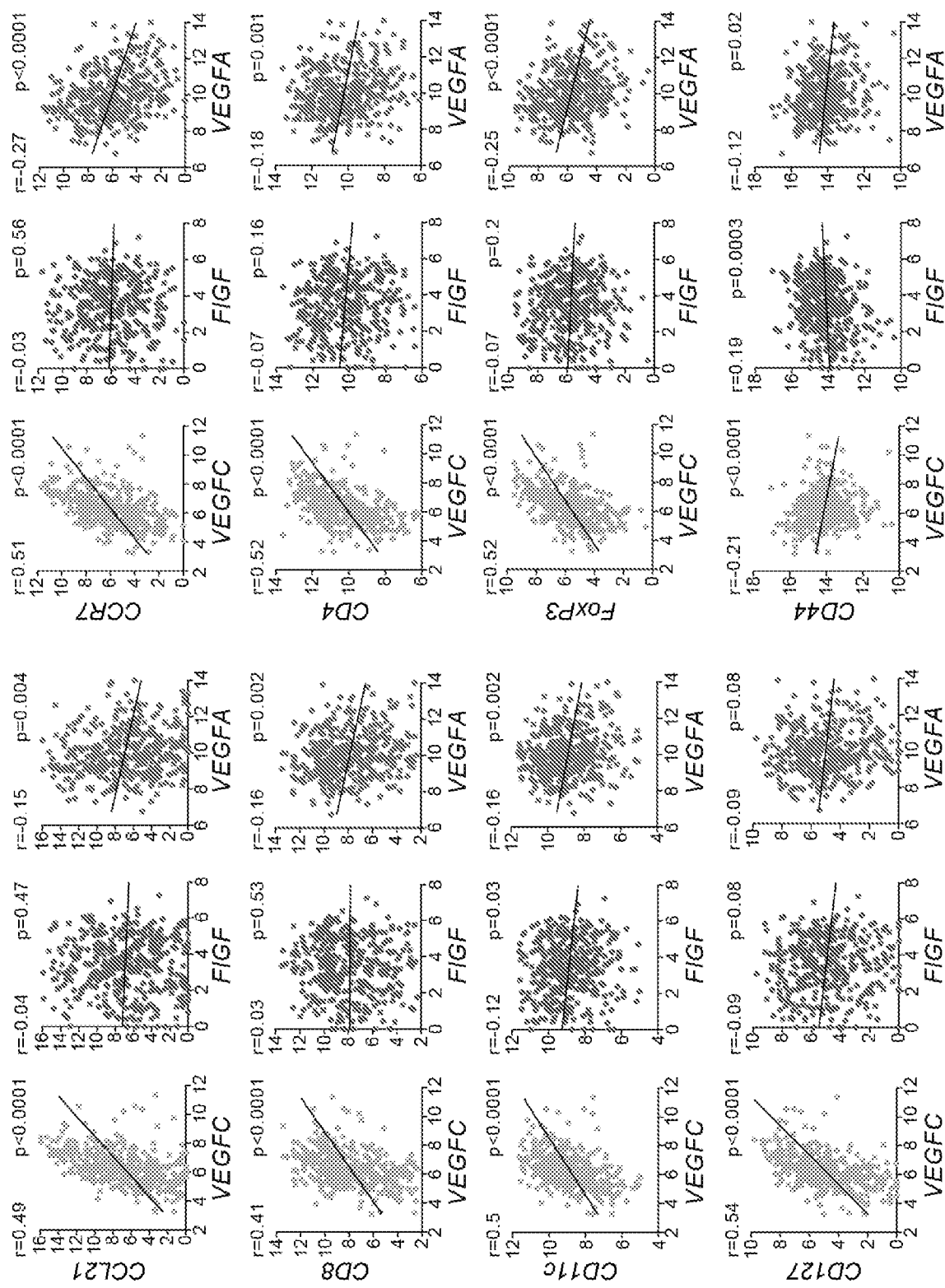
FIG. 20. Expression of VEGFC positively correlates with hallmarks of inflammation within metastatic sites of human melanoma. Correlations of gene expression data of samples from human metastatic melanoma sites from the cancer genome atlas (TCGA). Dot plots shown with linear regression curve (n=369, correlation was tested using non-parametric Spearman's test).

Several recent reports have described melanoma gene signatures that stratify patients that respond to immunotherapy and whose tumors contain high levels of T cells, from non-responders with poorly infiltrated tumors. We thus analyzed 469 metastatic melanoma patients from the Cancer Genome Atlas (TCGA) and found strong and highly significant correlations between VEGFC, but not VEGFA or FIGF (VEGF-D), and genes correlating with immunotherapy response (FIG. 13E, left). In addition, several genes correlated with immunotherapy resistance, including CTNNB1, MYC, and CXCL1 were inversely correlated with VEGFC (FIG. 13E, right). In line with our findings in mice, gene expression of VEGFC correlated with that of CCL21 and CCR7 in human primary melanoma, while expression of the other main VEGFR-3 ligand, FIGF (VEGF-D), showed no correlation (FIG. 13F, top 2 rows). Interestingly, VEGFA expression was inversely correlated with CCR7 expression and showed a similar trend (though not statistically significant) in CCL21 expression. According to our findings in mouse melanoma, expression of CD8, CD4, CD11c, FoxP3 and CD127 (expressed by naïve T cells), but not CD44 (expressed by activated T cells), correlated with that of VEGFC (FIG. 13F, bottom 3 rows). Interestingly, we observed the same trends in metastatic tumors from the same database (FIG. 20). Taken together, these data show that VEGFC and CCL21 expression are strongly correlated in human melanoma, and are consistent with the notion that VEGF-C/CCL21 upregulation shifts the immune microenvironment to be more highly T cell infiltrated.

E. VEGF-C Correlates with Response to Immunotherapy in Human Metastatic Melanoma Patients Given that we found VEGF-C to be a driver of tumor inflammation in human metastatic melanoma, we wanted to determine whether serum VEGF-C represents a biomarker to predict response to immunotherapy. Using sera stored from an earlier clinical study of 20 patients who underwent Melan-A analog vaccination, we measured circulating VEGF-C levels to compare with the previously described tumor-specific CD8+ T cell responses. Interestingly, we found that all patients with low VEGF-C showed weak responses, measured both in terms of numbers of circulating Melan-A-specific CD8+ T cells (FIG. 14A) as well as their expression of the effector cytokine IFNγ (FIG. 14B), while all responding patients had higher levels of VEGF-C. While the differences in expression of TNFα, IL-2 and CD107 did not reach statistical significance (FIG. 21A-D), Melan-A-specific T cells in patients with higher VEGF-C levels showed higher percentages of polyfunctionality (FIG. 14C).

We next wanted to assess whether serum VEGF-C levels could stratify responders and non-responders in a setting where the therapeutic interventions leads to actual clinical benefit. We thus measured serum VEGF-C levels of 76 patients who underwent combined anti-CTLA-4 (Ipilimumab) and anti-PD-1 (Nivolumab) therapy and correlated it with progression-free survival (PFS). Indeed, PFS of metastatic melanoma patients receiving combinatorial checkpoint blockade could be stratified according to high, medium and low serum VEGF-C, but not F1GF (VEGF-D, the other ligand for VEGFR-3) or VEGF-A levels (FIG. 14D). Taken together, these data demonstrate that serum VEGF-C levels prior to immunotherapy not only predicts the magnitude and quality of immune responses raised by a cancer vaccine, but also stratifies patient responses to combined checkpoint blockade.

F. Lymphangiogenic Potentiation of Immunotherapy is Dependent on CCR7 Signaling During Tumor Development and Independent of T Cells Activated in the Lymph Node.

It has been previously shown that naïve T cells can be recruited and primed within primary tumors, and that adoptive transfer of naïve OT-I cells into B16-OVA tumors can delay primary tumor growth. As such, we asked whether there was a mechanistic link between the increased susceptibility to immunotherapy and the increased accumulation of naïve TILs within lymphangiogenic B16 tumors. We hypothesized that naïve CCR7+ T cells within lymphangiogenic tumors might be locally activated following immunotherapy-induced release of tumor antigen and innate immune activation ("danger signals"). In line with this, we found that three days after ATT, lymphangiogenic B16-OVANC tumors but not the tumor-draining lymph nodes (tdLNs) contained significantly higher numbers of endogenous naïve and effector CD8+ T cells as well as transferred OT-I cells (FIG. 15A-B). To test whether the efficacy of ATT in B16 melanoma indeed relied on VEGF-C-induced recruitment of naïve immune cells, B16-OVA/VC tumor-bearing mice were treated with CCR7 blocking antibodies during tumor development prior to therapy. We found that after the initial response to ATT, B16-OVANC tumors of αCCR7-treated mice progressed similarly to αR3-treated mice, leading to accelerated tumor growth and significantly decreased survival as compared to isotype treated tumors (FIG. 15C). To assess whether naïve T cells might be activated within the primary tumor microenvironment, we next performed ATT while blocking lymphocyte egress from secondary lymphoid organs using the small molecular inhibitor FTY720. Indeed, tumor growth in the progression phase after ATT was only dependent on VEGFR-3 signaling, but independent of lymphocyte egress (FIG. 15D). Accordingly, the blood of FTY720 treated mice was essentially devoid of lymphocytes (FIG. 15E-F), further indicating that for the long-term response, anti-tumor immunity does not rely on circulating lymphocytes, but on intratumoral activation and expansion of TILs. Together, these data demonstrate that lymphangiogenic potentiation of immunotherapy in B16 melanomas depends on CCR7-mediated attraction of naïve T cells to and their subsequent activation and expansion within the primary tumor microenvironment.

G. Mice that Reject Lymphangiogenic B16 Melanomas after Immunotherapy Show Epitope Spreading and Protection to Re-Challenge Immunotherapy can broaden the endogenous anti-tumor immune response to tumor epitopes that were previously not or not sufficiently visible, a process called epitope spreading. Because we found that naïve endogenous T cells are activated and expanded within lymphangiogenic B16 melanomas in response to antigen-specific immunotherapy, we hypothesized that spreading of the anti-tumor immune response to antigens other than OVA could occur in these settings. To determine whether this was the case, we re-challenged mice that completely rejected the primary tumor (as shown in FIG. 11E) with an intravenous injection of B16 WT or B16-OVA/VC cells. Intriguingly, we found that mice that rejected B16-OVA/VC tumors had increased numbers of overall effector CD4$^+$ and CD8$^+$ T cells as well as of OVA-specific CD8$^+$ T cells in blood as compared to mice that had progressing B16-OVA tumors (FIG. 16A). To assess whether the increased numbers of effector T cells were the result of epitope spreading within the tumor microenvironment, we re-challenged mice that were tumor free for at least 10 days with pulmonary metastasis. While control mice that only received OVA+CpG vaccination were only partially protected against B16-OVA but not B16 WT metastasis, mice that previously rejected B16-OVA/VC tumors were completely protected against both B16-OVA and B16 WT metastasis (FIG. 16B-C). Moreover, increased levels of circulating OVA-specific CD8$^+$ T cells were detected in mice resistant to pulmonary metastasis (FIG. 16D). Taken together, these data suggest that antigen-specific immunotherapy of lymphangiogenic B16 tumors induces secondary immune responses against a variety of endogenous tumor antigens, conferring long-term memory and protection against pulmonary metastasis.

This work introduces a new and unexpected role of tumor-associated lymphangiogenesis in enhancing the efficacy of systemic immunotherapy. Although lymphangiogenic tumors are more immunosuppressive before immunotherapy, it was surprisingly found that they turned out to be more sensitive to systemic immunotherapy as compared to those where VEGFR-3 signaling was blocked (FIGS. 11 and 18). It is hypothesized that lymphangiogenic potentiation of immunotherapy depends on CCL21-mediated recruitment of CCR7$^+$ immune cells, particularly naïve T cells and DCs, into primary melanoma tumors (FIGS. 12 and 17). When immunotherapy-induced cytotoxicity occurs, the release of antigens and danger signals induce local T cell activation, thereby leading to a diversification of the endogenous anti-tumor response ('epitope spreading') and long-lasting memory (FIGS. 15 and 16). Importantly, systemic immunotherapy and intratumoral activation of endogenous T cells do not rely on the tumor draining lymph nodes, which have acquired robust mechanisms of immuno suppression. These findings thus point to tumor lymphangiogenesis (inferred from serum VEGF-C levels) as a biomarker for tumor T cell infiltration, which others have shown to correlate with responsiveness to immunotherapy. It is shown here, in two independent clinical immunotherapy settings, peptide vaccination and checkpoint blockade, that VEGF-C levels in the serum positively correlated with the numbers and functionality of circulating tumor-specific CD8$^+$ T cells (FIGS. 14A-C) and progression-free survival, respectively (FIG. 14D).

These findings are surprising because VEGF-C expression in human tumors is strongly correlated with LN metastases and poor prognosis. Here the inventors find that lymphangiogenic melanomas express high levels of CCL21 (FIGS. 12D and 19D), a lymphoid homing chemokine that attracts naïve and memory T cells as well as dendritic cells and show that lymphangiogenic tumors contain increased numbers of naïve TILs that can contribute to increased efficacy of different immunotherapy approaches (FIGS. 11 and 18). It is shown here, for the first time, that CCL21 expression and subsequent naïve T cell infiltration within lymphangiogenic mouse melanomas depends on VEGFR-3 signaling, that intratumoral LECs express CCL21 and that VEGFC but not VEGFA or -D positively correlated with CCL21, CCR7, and with a gene signature of T cell inflammation in a human melanoma TCGA data set (FIGS. 13E, F, and FIG. 20). Taken together, this data show that LECs can actively influence primary tumor inflammation by secreting CCL21, assigning a new biological role of intra- and peri-tumoral lymphatics during tumor progression.

We conclude that tumor expression of VEGF-C is a novel mechanism by which tumor associated lymphatics actively increase naïve immune cell infiltration. Activation of naïve T cells can be induced by immunogenic cell death following immunotherapy, resulting in a broad and long lasting anti-tumor immune response. Considering our pre-clinical results, the immune microenvironment specific to lymphangiogenic melanoma might offer a window of opportunity to jumpstart an immunosuppressed Cancer-Immunity Cycle in the clinic. We therefore propose tumor-associated lymphangiogenesis to be a major determinant of a patients 'cancer immunogram' and speculate that engineering lymphangiogenesis within primary melanoma might improve response rates of patients with non-T cell-inflamed primary melanomas.

H. Materials and Methods

1. Mice

Female wild-type mice, OT-I RAG-1$^{-/-}$ mice, and CD45.1 mice, all on the C57BL/6 background, were purchased from Harlan Laboratories (Gannat, France) and used between 8-12 weeks of age. Tyr:Cre-ER$^+$/LSL-Braf$^{V600E}$/Pten$^{fl/fl}$ genetically engineered mice (BRAF GEM) were a kind gift from Dr. T. Gajewski (University of Chicago). All experiments were performed with approval from the Veterinary Authority of the Canton de Vaud, Switzerland, and IACUC of University of Chicago, #72414.

2. Tumor Cell Lines

B16-F10 melanoma cells (ATCC) were maintained in high glucose DMEM (11995) supplemented with 10% heat-inactivated fetal bovine serum (FBS) (both from Invitrogen, Zug, Switzerland). B16-F10 ovalbumin (OVA) expressing cells (gift of Bertrand Huard, University of Geneva, Geneva, Switzerland) were transfected with control or VEGF-C lentivirus as described previously (B16-OVA and B16-OVA/VC, respectively), and expression of VEGF-C and OVA were confirmed before each experiment by qPCR and ELISA. Cells were split 1:20 or 1:40 every 3-4 days.

3. B16 Tumor Inoculation and Measurements

Before tumor inoculation, mice were anesthetized with isoflurane and their backs were shaved. $2.5 \times 10^5$ B16-OVA or B16-OVA/VEGF-C cells in 30 µl PBS were injected i.d. on the front dorsolateral side above the shoulders. Tumor size was monitored with a caliper, and volume (V) was calculated assuming an ellipsoid shape (V=1/6π×length×width×height). Mice were sacrificed when tumor volume exceeded 500 mm$^3$.

4. BRAF GEM Induction, Treatment and Measurements 8-12-week-old mice were shaved on the back, while under anesthesia. The next day, 5 µl of hydroxytamoxifen (4-OH-tamoxifen, Sigma-Aldrich) at 10 mg/mL in pure ethanol was applied topically on the shaved area. Treatment started two weeks after hydroxytamoxifen application, when tumor was first palpable. Tumor volume was calculated as Volume=Surface*Z, where Surface is generated through ImageJ analysis and Z measured using a digital caliper, as previously described (Ishihara et al., 2017). Mice were euthanized when tumor volume reached 1000 mm$^3$ or when necrosis occurred.

5. Antibody Injections

To inhibit tumor lymphangiogenesis, mice received i.p. injections of 500 µg anti-VEGFR-3 antibody (mF4-31C1; ImClone/Eli Lilly, New York, USA) or isotype rat IgG (14131; Sigma, Buchs, Switzerland) every 3-4 days starting the day of B16 inoculation. For CCR7 blocking studies, mice received i.p. injections of 25 µg anti-CCR7 antibody (16-1971; eBioscience, Vienna, Austria) or isotype rat IgG on day 0, 3, and 6 after tumor inoculation. For the GEM study, mice first received i.p. injections of 500 µg anti-VEGFR-3 antibody or isotype rat IgG every 4 days, starting when the tumor was palpable. Mice then received i.p. injections of 250 µg anti-PD-1 antibody (RMP1-14; BioXCell, West Lebanon, N.H., USA) every 4 days, starting 12 days after start of VEGFR3 blocking treatment.

6. Protein and Peptide Vaccinations

For protein vaccination, mice received 50 µg CpG-B (5'-TCCATGACGTTCCTGACGTT-3'; Microsynth, Balgach, Switzerland) combined with 10 µg OVA grade V (A5503; Sigma) in two i.d. doses 25 µl per hind footpad (targeting non-tumor-draining lymph nodes) on day 4, 7, and 10 after tumor inoculation. Trp-2-peptide-conjugated nanoparticles (NP-Trp2) were produced as described previously, and 2 µg NP-Trp2 combined with 10 µg OVA grade V administered as described for the protein vaccination. For the GEM study, mice received two doses of 20 µg of CpG-B and 2 µg of gp100 peptide (KVPRNQDWL; GenScript, Piscataway, N.J., USA), at day 8 and 12 after start of VEGFR3 blocking treatment.

7. OT-I Ex Vivo Activation and Therapeutic Adoptive Transfer

Spleens and LNs were harvested from OT-I mice. Spleens were placed in a petri dish containing 10 ml IMDM medium (31980-022; Invitrogen) and disrupted with a scalpel before being transferred through a 70 µm filter into a 50 ml conical tube. Cells were then spun down at 2000 rpm for 5 min and resuspended in 1 ml ACK red blood cells lysis buffer (150 mM $NH_4Cl$, 10 mM $KHCO_3$, and 0.1 mM $Na_2EDTA$, pH 7.2). After 5 min incubation, 10 ml IMDM was added, and the cells spun down at 2000 rpm for 5 min. LNs were placed in a well of a twelve well plate containing 2 ml digestion medium (IMDM with 1 mg/ml Collagenase D (11088866600; Roche, Basel, Switzerland)). The lymph node capsules were gently opened with two syringe needles (26G) to allow better digestion, and then incubated for 15 min at 37° C. LN cells were then spun down at 2000 rpm for 5 min and pooled in 10 ml IMDM with the splenocytes for further processing. Dendritic cells (DCs) were first isolated by $CD11c^+$ magnetic cell sorting (130-052-001; Milteny Biotec, Bergisch Gladbach, Germany) before $CD8^+$ T cells were isolated from the remaining cells by negative magnetic cell sorting (130-095-236; Milteny Biotech) according to the manufacturer's protocol. Next, isolated $CD11c^+$ DCs and $CD8^+$ T cells were plated in 96-well plates (10,000 $CD11c^+$ DCs and 100,000 CD8+ T cells per well) in stimulation medium (IMDM with 10% FBS, 1% Pen/Strep, 1 nM SIINFEKL, and 10 U/ml mIL-2 (212-12; PreproTech, London, UK)). Cells were collected after 4 days and injected i.v. into tumor-bearing mice ($10^6$ cells in 200 µl in IMDM).

8. Therapeutic Dendritic Cell Vaccination

BMDCs were generated from the bone marrow of C57BL/6 mice as previously described. At day 8 of BMDC culture, 10 ng/ml LPS was added for 12 h. The activated BMDCs were then washed with 20 ml IMDM with 10% FBS and plated at $3\times10^6$ cells/ml in petri dishes. The cells were then pulsed with 1 µM of SIINFEKL for 1 h. Cells were then collected and washed 3 times with 20 ml PBS. Finally, cells were resuspended in PBS at $10^7$ cells/ml, and 100 µl was injected i.p. per mouse.

9. Lymph Node and Tumor Cell Isolation

Stromal cells ($CD45^-$) and immune cells ($CD45^+$) were recovered from tumors and lymph nodes (LNs) as described. Briefly, LN capsules were opened with syringe needles and digested in 1 mg/ml Collagenase IV (LS004188; Worthington-Biochem, New Jersey, USA) and 40 µg/ml DNAse I (11284932001; Roche) for 30 min at 37° C. with magnetic stirring. Supernatant was then carefully collected and remaining fragments were further digested with 3.3 mg/ml Collagenase D (11088866001; Roche) and 40 µg/ml DNAse I for 15 min (for lymph nodes) or 45 min (for tumors) followed by 500 mM EDTA.

10. Immunohistochemistry

Mouse tumor samples were fixed in Zinc fixation buffer (4.5 mM $CaCl_2$, 51.5 mM $ZnCl_2$, 32 mM $Zn(CF_3CO_2)_2$, and 38.5 mM glycine, pH 6.5), paraffin-embedded and cut into 8 µm sections. Formalin-fixed human tumors were paraffin-embedded and cut into 4-5 µm sections. For immunostaining, paraffin-embedded tissue sections were deparaffinized and rehydrated. Antigen retrieval was done on PFA-fixed samples at 98° C. for 15 min in TRIS/EDTA buffer (pH 9.0). Sections were then stained according to standard immunohistochemistry protocols. Primary antibodies used were: rabbit anti-mouse LYVE-1 (103-PASO; RELIATech, Wolfenbüttel, Germany, 1:200), mouse anti-human D2-40 (SIG-3739; BioLegend, Lucerne, Switzerland), rabbit anti-human CCL21 (HPA051210; Sigma), rabbit anti-human VEGFC (PAS-29772, Invitrogen). Quantification of lymphatic vessels on entire tumor tile images was performed using Fiji. LYVE-$1^+$ cells with Prox$1^-$ nuclei were excluded as macrophages.

11. Flow Cytometry

Antibody staining for surface targets were performed in PBS with 2% FCS, and intracellular staining was performed after fixation and permeabilization according to the manufacturers' protocols. The following anti-mouse antibodies were used for flow cytometry: CD45-APC (17-0451-82; eBioscience) or biotinylated CD45 (13-0451-85; eBioscience), CD4-PacBlue (100531; Biolegend) or CD4-PE-Cy7 (100528; Biolegend), CD8a-PacOrange (MCD0830; Invitrogen), F4/80-PerCPCy5.5 (123128; Biolegend), CD25-FITC (101908; Biolegend), FoxP3-PerCPCy5.5 (45-5773-82; eBioscience), CD62L-PE (12-0621-82; eBioscience), CD44-APCeF780 (47-0441-82; eBioscience), CCR7-PE-Cy7 (25-1971-82; eBioscience) or CCR7-PerCPCy5.5 (45-1971-82; eBioscience), biotinylated CD11b (13-0112-82; eBioscience). Pentamer staining for H-2kb-Trp2-PE (SVYDFFVWL; TC Metrix, Lausanne, Switzerland), H-2Db-gp100-PE (KVPRNQDWL; TC Metrix) and H-2kb-SIINFEKL-PE (F093-2B; ProImmune, Oxford, UK) was performed according to manufacturers' guidelines. Cell viability was determined using live/dead aqua (L34957; Invitrogen) or red (L23102; Invitrogen) dyes. Flow cytometry acquisition was performed on a Cyan flow cytometer (Beckman Coulter) and data analysis was performed with FlowJo (Version 9.7.7.).

12. ELISAs and Protein Array

Protein lysates were generated from excised tumors and lymph node by homogenizing the tissues in 700 µl (tumors) or 400 µl (lymph nodes) T-Per protein extraction buffer (78510; ThermoFisher) containing cOmplete protease inhibitor cocktail (1 tablet per 10 ml, 11836145001; Roche). Tissue lysates were spun down at 2000 g for 2 min, and transferred into new 1.5 ml microcentrifuge tubes. Tissue lysates were then spun at 12,000 g for 10 min to get rid of cell debris, and the supernatant was transferred into new 1.5 ml eppendorf tubes which were stored at −80° C. Lymph node lysates were normalized to 0.025 mg/ml total protein, tumor lysates to 1 mg/ml total protein, and ELISAs (CCL21: DY457, RnD Systems, Abingdon, UK; VEGFC: DVECOO, RnD Systems) were performed according to standard protocols. Cytokine protein arrays (AAM-CYT-2-2; RayBiotech, Norcross Ga., USA) were performed according to manufacturer's specifications.

13. Analysis of TCGA Data Set Containing 469 Skin Cutaneous Melanoma Patients

TCGA level 3 gene expression data were downloaded for skin cutaneous melanoma (SKCM) from the Broad GDAC Firehose database (http://gdac.broadinstitute.org/). The RNAseq data set called "illuminahiseq_rnaseqv2-RSEM_genes_normalized (MD5)" with release date 20151101 contained upper quartile normalized RSEM values summarized at the gene level. The data was log 2 transformed after the addition of one pseudoread. The total of 469 SKCM samples were split into two groups according to whether the tissue biopsy was retrieved from the primary melanoma site (103 samples) or a metastatic site (369 samples) including sentinel lymph nodes and distant organ metastasis. Heat maps were generated using RStudio (RStudio Team (2015). RStudio: Integrated Development for R. RStudio, Inc., Boston, Mass., version 0.99.893).

14. Vaccination Trial in Melanoma Patients

For immunotherapy response correlations, we analyzed serum from Stage III/IV melanoma patients that had been enrolled in a prospective Phase I clinical study evaluating an anti-tumor peptide vaccine (ClinicalTrials.gov Identifier NCT00112229) performed by the Ludwig Institute for Cancer Research (University Hospital, Lausanne, Switzerland). The trial was conducted according to the relevant regulatory standards, upon approval by Swissmedic and the "Commission d'Ethique de la Recherche Clinique de la Faculté de Biologie et de Médecine, Université de Lausanne", which also approved the use of specimens from healthy volunteers. Patients were enrolled upon written informed consent. Briefly, patients had received monthly s.c. injections of a vaccine composed of CpG 7909 (PF-3512676) oligonucleotides and Melan-A/MART-1 peptide, emulsified in Montanide ISA-51. Melan-A-specific $CD8^+$ T cells frequency and function was measured in blood by flow cytometry at the time point of peak response (after a mean of 8 injections). Serum VEGF-C was assessed using a commercial ELISA kit (DVECOO; RnD Systems).

15. Serum Study of Metastatic Melanoma Patients

Serum was collected from treatment-naive patients with unresectable, stage III or stage IV metastatic melanoma in the randomized, placebo controlled, multi-center, two arm, phase II trial, BMS Checkmate-069 (CA209-069, NCT01927419). All patients provided written informed consent within the study for the use of biological material including serum analyzes. The study was approved by all IRBs. The study compared ipilimumab (n=47) at 3 mg/kg, every 3 weeks for four doses to combined (n=95) ipilimumab, 3 mg/kg, every 3 weeks and nivolumab 1 mg/kg, every 3 weeks for 4 cycles, followed by nivolumab alone at 3 mg/kg, every 2 weeks until disease progression or unacceptable toxicity (For details of the study please also refer to NEJM and www.clinicaltrials.gov). 135 pre-treatment serum samples (46 in the ipilimumab arm and 89 in the ipilimumab plus nivolumab arm) were analyzed, one sample per patient. Depending on the volume of available serum, serum was undiluted (n=103) or diluted (n=33) in median 1.16 times (range of dilution factor: 1.02-2). 700 µl per sample was analyzed using the 440 Human Biomarker testing service (RayBiotech, Inc. Parkway Lane, Suite 100, Norcross Ga., 30092). Only the ipilimumab plus nivolumab arm was included for our analysis, from which 13 patients were excluded because they had very short follow-up (<10 days) and/or had no clear evaluation of response/progression at the first data cutoff. Progression free survival was defined according RECIST 1.1 criteria. Patients were grouped according to the serum levels of VEGF-C, -D, and -A into high (concentration>mean+SD/2.5), low (concentration<mean−SD/2.5), and mid (in between high and low).

16. Statistical Analysis

Statistical analysis was done using Prism (v5.0 d, GraphPad). Except mentioned differently, statistically significant differences between two experimental groups were determined by an unpaired student's t-test, and by One-way ANOVA followed by Tukey's post-test when more than two groups were compared. Statistical significance between survival curves assessed with Log-rank (Mantel-Cox) test. TCGA gene data correlations were tested using non-parametric Spearman's test. *$p<0.05$, $p<0.01$, *$p<0.001$, ns: not significant.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bachmann & Jennings, Vaccine delivery: a matter of size, geometry, kinetics and molecular patterns. *Nature reviews. Immunology* 10, 787-796 (2010).

Banchereau & Steinman, Dendritic cells and the control of immunity. *Nature* 392, 245-252 (1998).

Card, Emerging roles of lymphatic endothelium in regulating adaptive immunity. *The Journal of clinical investigation* 124, 943-952 (2014).

Chen & Flies, Molecular mechanisms of T cell co-stimulation and co-inhibition. *Nature reviews. Immunology* 13, 227-242 (2013).

den Haan, et al., Cd8+ but Not Cd8—Dendritic Cells Cross-Prime Cytotoxic T Cells in Vivo. *The Journal of Experimental Medicine* 192, 1685-1696 (2000).

Dörner & Radbruch, Antibodies and B Cell Memory in Viral Immunity. *Immunity* 27, 384-392 (2007).

Dubrot, et al. Lymph node stromal cells acquire peptide-MHCII complexes from dendritic cells and induce antigen-specific CD4+ T cell tolerance. *The Journal of experimental medicine* 211, 1153-1166 (2014).

Fletcher, et al. Lymph node fibroblastic reticular cells directly present peripheral tissue antigen under steady-state and inflammatory conditions. *The Journal of Experimental Medicine* 207, 689-697 (2010).

Gerlach, et al. One naive T cell, multiple fates in CD8+ T cell differentiation. *The Journal of Experimental Medicine* 207, 1235-1246 (2010).

Hirosue & Dubrot, Modes of antigen presentation by lymph node stromal cells and their immunological implications. *Front Immunol* 6 (2015).

Hirosue, et al. Steady-State Antigen Scavenging, Cross-Presentation, and CD8+ T Cell Priming: A New Role for Lymphatic Endothelial Cells. *Journal of immunology* 192, 5002-5011 (2014).

Hubbell, et al., Materials engineering for immunomodulation. *Nature* 462, 449-460 (2009).

Kaech & Wherry, Heterogeneity and Cell-Fate Decisions in Effector and Memory CD8+ T Cell Differentiation during Viral Infection. *Immunity* 27, 393-405 (2007).

Lukacs-Kornek, et al. Regulated release of nitric oxide by nonhematopoietic stroma controls expansion of the activated T cell pool in lymph nodes. *Nature immunology* 12, 1096-1104 (2011).

Lund, et al. VEGF-C Promotes Immune Tolerance in B16 Melanomas and Cross-Presentation of Tumor Antigen by Lymph Node Lymphatics. *Cell Reports* 1, 191-199 (2012).

Lutz, et al. An advanced culture method for generating large quantities of highly pure dendritic cells from mouse bone marrow. *Journal of Immunological Methods* 223, 77-92 (1999).

Maisonneuve, et al., Unleashing the potential of NOD- and Toll-like agonists as vaccine adjuvants. *Proceedings of the National Academy of Sciences* 111, 12294-12299 (2014).

Malhotra, et al. Transcriptional profiling of stroma from inflamed and resting lymph nodes defines immunological hallmarks. *Nature immunology* 13, 499-510 (2012).

Martino, et al. Growth factors engineered for super-affinity to the extracellular matrix enhance tissue healing. *Science* 343, 885-888 (2014).

Martino, et al., Heparin-binding domain of fibrin(ogen) binds growth factors and promotes tissue repair when incorporated within a synthetic matrix. *Proceedings of the National Academy of Sciences of the United States of America* 110, 4563-4568 (2013).

Moon, et al., Engineering nano- and microparticles to tune immunity. *Advanced materials* 24, 3724-3746 (2012).

Sallusto, et al., Two subsets of memory T lymphocytes with distinct homing potentials and effector functions. *Nature* 401, 708-712 (1999).

Schulz & Reis e Sousa, Cross-presentation of cell-associated antigens by CD8α+ dendritic cells is attributable to their ability to internalize dead cells. *Immunology* 107, 183-189 (2002).

Scott, et al. Dendritic cell activation and T cell priming with adjuvant- and antigen-loaded oxidation-sensitive polymersomes. *Biomaterials* 33, 6211-6219 (2012).

Seder, et al., T-cell quality in memory and protection: implications for vaccine design. *Nat Rev Immunol* 8, 247-258 (2008).

Sprent & Surh, Generation and maintenance of memory T cells. *Current Opinion in Immunology* 13, 248-254 (2001).

Tewalt, et al. Lymphatic endothelial cells induce tolerance via PD-L1 and lack of costimulation leading to high-level PD-1 expression on CD8 T cells. *Blood* 120, 4772-4782 (2012).

Wherry, et al. Lineage relationship and protective immunity of memory CD8 T cell subsets. *Nat Immunol* 4, 225-234 (2003).

Zisch, et al., Covalently conjugated VEGF-fibrin matrices for endothelialization. *Journal of Controlled Release* 72, 101-113 (2001).

---

The invention claimed is:

1. A method for treating melanoma, the method comprising administering to the subject one or more lymphangiogenesis inducers comprising vascular endothelial growth factor C (VEGF-C) or vascular endothelial growth factor D (VEGF-D) and an effective amount of a melanoma-specific antigen.

2. The method of claim 1, wherein the one or more lymphangiogenesis inducers further comprise CCL21.

3. The method of claim 1, wherein the subject is also administered an adjuvant.

4. The method of claim 1, wherein the subject is administered an effective amount of a second antigen.

5. The method of claim 1, wherein the lymphangiogenesis inducer is incorporated into a matrix.

6. The method of claim 5, wherein the antigen is bound or incorporated into the matrix and is cleavable.

7. The method of claim 5, wherein the matrix incorporates one or more cleavable chemoattractants or one or more cleavable cytokines.

8. The method of claim 5, wherein the matrix is a hydrogel, and optionally, wherein the hydrogel is a fibrin hydrogel or a fibrin domain modified polyethylene glycol hydrogel.

9. The method of claim 5, wherein the lymphangiogenesis inducer is capable of binding to the matrix or hydrogel and/or wherein the lymphangiogenesis inducer comprises a matrix binding domain.

10. The method of claim 5, wherein the lymphangiogenesis inducer comprises a protease cleavage site, and optionally, wherein the protease cleavage site is a matrix metalloprotease cleavage site.

11. The method of claim 9, wherein the lymphangiogenesis inducer is a modified vascular endothelial growth factor C (VEGF-C) protein comprising a fibrin-binding domain.

12. The method of claim 5, wherein the matrix or hydrogel is implanted into the subject.

* * * * *